United States Patent
Catalano et al.

(10) Patent No.: US 9,765,122 B2
(45) Date of Patent: Sep. 19, 2017

(54) THERAGNOSTIC PARTICLES

(71) Applicant: University of Washington through its Center for Commercialization, Seattle, WA (US)

(72) Inventors: Carlos Enrique Catalano, Seattle, WA (US); Jenny Ren-Jye Chang, Seattle, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 0 days.

(21) Appl. No.: 14/652,645

(22) PCT Filed: Jan. 20, 2014

(86) PCT No.: PCT/US2014/012206
§ 371 (c)(1),
(2) Date: Jun. 16, 2015

(87) PCT Pub. No.: WO2014/113759
PCT Pub. Date: Jul. 24, 2014

(65) Prior Publication Data
US 2015/0337014 A1    Nov. 26, 2015

Related U.S. Application Data

(60) Provisional application No. 61/754,458, filed on Jan. 18, 2013.

(51) Int. Cl.
| | |
|---|---|
| *A61K 38/16* | (2006.01) |
| *C12N 7/00* | (2006.01) |
| *C12N 7/01* | (2006.01) |
| *C12N 15/00* | (2006.01) |
| *C07K 14/005* | (2006.01) |
| *A61K 38/17* | (2006.01) |

(52) U.S. Cl.
CPC .......... *C07K 14/005* (2013.01); *A61K 38/177* (2013.01); *C12N 7/00* (2013.01); *C07K 2319/735* (2013.01); *C12N 2795/10023* (2013.01); *C12N 2795/10042* (2013.01)

(58) Field of Classification Search
None
See application file for complete search history.

(56) References Cited

U.S. PATENT DOCUMENTS

| | | | |
|---|---|---|---|
| 5,211,657 A | 5/1993 | Yamada et al. | |
| 6,740,524 B1 | 5/2004 | Akuta et al. | |
| 8,802,418 B2 | 8/2014 | Rao | |
| 2002/0019369 A1 | 2/2002 | Li et al. | |
| 2008/0305119 A1 | 12/2008 | Dewhurst et al. | |
| 2012/0214867 A1 | 8/2012 | Liu et al. | |

FOREIGN PATENT DOCUMENTS

| | | |
|---|---|---|
| WO | 2004009664 A2 | 1/2004 |
| WO | 2008115296 A2 | 9/2008 |

OTHER PUBLICATIONS

Maluf, et al., "Assembly of bacteriophage lambda terminase into a viral DNA maturation and packaging machine," Biochemistry, vol. 45, No. 51, pp. 15259-15268, 2006.
Maluf, et al., "Self-association properties of the bacteriophage [lambda] terminase holoenzyme: implications for the DNA packaging motor," Journal of Molecular Biology, vol. 347, No. 3, pp. 523-542, 2005.
Maruyama, et al., "Lambda foo: a lambda phage vector for the expression of foreign proteins," Proceedings of the National Academy of Sciences USA, vol. 91, No. 17, pp. 8273-8277, 1994.
Medina, "Growing Pains of Bacteriophage Lambda: Examination of the Maturation of Procapsids into Capsids," Ph.D. Dissertation, University of Washington, 204 pages, 2010.
Roizman, et al., "Multiplication of Viruses: An Overview," Fields Virology, Third edit., pp. 101-111, 1996.
Medina, et al., "Assembly and Maturation of the Bacteriophage Lambda Procapsid: gpC is the Viral Protease," Journal of Molecular Biology, vol. 401, No. 813-830, 2010.
Medina, et al. "The Bacteriophage Lambda gpNu3 Scaffolding Protein is an Intrinsically Disordered and Biologically Functional Procapsid Assembly Catalyst," Journal of Molecular Biology, vol. 412, pp. 723-736, 2011.
Roizman, et al.,"Herpes Simplex Viruses," Fields Virology, Fifth edit., pp. 2501-2602, 2007.
Medina, et al., "Thermodynamic Characterization of Viral Procapsid Expansion into a Functional Capsid Shell," Journal of Molecular Biology, vol. 418, No. 3-4, pp. 167-180, 2012.
Meyer, et al., "The phage lambda terminase enzyme: 1. Reconstitution of the holoenzyme from the individual subunits enhances the thermal stability of the small subunit," International Journal of Biological Macromolecules, vol. 23, No. 1, pp. 27-36, 1998.
Mikawa, et al., "Surface display of proteins on bacteriophage lambda heads," Journal of Molecular Biology, vol. 262, No. 1, pp. 21-30, 1996.
Mittag et al. (Mar.-Apr. 2010) "Protein dynamics and conformational disorder in molecular recognition," Journal of Molecular Recognition, 23(2):105-116, 2010.
Moisant, et al., "Exploring the paths of (virus) assembly," Biophysical Journal, vol. 99, No. 5, pp. 1350-1357, 2010.
Morais, et al., "Cryoelectron-microscopy image reconstruction of symmetry mismatches in bacteriophage phi29," Journal of Structural Biology, vol. 135, No. 1, pp. 38-46, 2001.

(Continued)

*Primary Examiner* — Hasan Ahmed
*Assistant Examiner* — Thea D' Ambrosio
(74) *Attorney, Agent, or Firm* — McDonnell Boehnen Hulbert & Berghoff LLP

(57) ABSTRACT

The present invention provides viral-based nanoparticles for therapeutic and diagnostic use, and methods for making and using the nanoparticles. Specifically, such nanoparticles comprise decoration-competent viral particles shells such as expanded capsids of phages, stabilized with engineered decoration proteins that have been linked to one or more compounds not naturally occurring on a wild type viral capsid.

17 Claims, 14 Drawing Sheets

(56) References Cited

OTHER PUBLICATIONS

Murialdo, "Bacteriophage lambda DNA maturation and packaging," Annuual Reviews of Biochemistry, vol. 60, pp. 125-153, 1991.
Murialdo, et al., "Head Morphogenesis of Complex Double-Stranded Deoxyribonucleic Acid Bacteriophages," Microbiological Reviews, vol. 42, No. 3, pp. 529-576, 1978.
Murialdo, et al., "Model for arrangement of minor structural proteins in head of bacteriophage lambda," Nature, vol. 257, No. 5529, pp. 815-817, 1975.
Murialdo, et al., "The morphogenesis of bacteriophage lambda: IV. Identification of gene products and control of the expression of the morphogenic information," Virology, vol. 48, No. 3, pp. 785-823, 1972.
Murialdo, et al., "The morphogenesis of phage lambda. V. Form-determining function of the genes required for the assembly of the head," Virology, vol. 48, No. 3, pp. 824-835, 1972.
Myers, et al., "Denaturant m values and Heat Capacity Changes: Relation to Changes in Accessible Surface Areas of Protein Unfolding," Protein Science, vol. 4, No. 10, pp. 2138-2148, 1995.
Nash, et al., "Overproduction of *Escherichia coli* integration host factor, a protein with nonidentical subunits," Journal of Bacteriology, vol. 169, No. 9, pp. 4124-4127, 1987.
Newcomb, et al., "Assembly of the Herpes Simplex Virus Capsid: Characterization of Intermediates Observed During Cell-free Capsid Formation," Journal of Molecular Biology, vol. 263, No. 3, pp. 432-446, 1996.
Newcomb, et al., "Assembly of the herpes simplex virus procapsid from purified components and identification of small complexes containing the major capsid and scaffolding proteins," Journal of Virology, vol. 73, No. 5, pp. 4239-4250, 1999.
Nicastro, et al., "Construction and Analysis of a Genetically Tuneable Lytic Phage Display System," Applied Microbiology and Biotechnology, vol. 97, No. 17, pp. 7791-7804, 2013.
Nurmemmedov, et al., "Biophysics of viral infectivity: matching genome length with capsid size," Quarterly Reviews of Biophysics, vol. 40, No. 4, pp. 327-356, 2007.
Nurmemmedov, et al., "Challenging Packaging Limits and Infectivity of Phage Lambda," Journal of Molecular Biology, vol. 415, No. 2, pp. 263-273, 2012.
Ortega, et al., "Bacteriophage lambda gpNu1 and *Escherichia coli* IHF proteins cooperatively bind and bend viral DNA: implications for the assembly of a genome-packaging motor," Biochemistry, vol. 45, No. 16, pp. 5180-5189, 2006.
Ortega, et al., "The DNA maturation domain of gpA, the DNA packaging motor protein of bacteriophage lambda, contains an ATPase site associated with endonuclease activity," Journal of Molecular Biology, vol. 373, No. 4, pp. 851-865, 2007.
Pace, "Conformational stability of globular proteins," Trends in Biochemical Sciences, vol. 15, No. 1, pp. 14-17, 1990.
Pace, "Linear Extrapolation Method of Analyzing Solvent Denaturation Curves," Proteins, vol. 41, Suppl 4, pp. 1-7, 2000.
Pace, et al., "How to measure and predict the molar absorption coefficient of a protein," Protein Science, vol. 4, No. 11, pp. 2411-2423, 1995.
Parent, et al., "A second-site suppressor of a folding defect functions via interactions with a chaperone network to improve folding and assembly in vivo," Molecular Microbiology, vol. 54, No. 4, pp. 1036-1050, 2004.
Parent, et al., "Electrostatic interactions govern both nucleation and elongation during phage P22 procapsid assembly," Virology, vol. 340, No. 1, pp. 33-45, 2005.
Parent, et. al., "Stepwise Molecular Display Utilizing Icosahedral and Helical Complexes of Phage Coat and Decoration Proteins in the Development of Robust Nanoscale Display Vehicles," Biomaterials, vol. 33, No. 22, pp. 5628-5637, 2012.
Parker, et al., "Bacteriophage P22 scaffolding protein forms oligomers in solution," Journal of Molecular Biology, vol. 268, No. 3, pp. 655-665, 1997.
Patel, et al., "Structure and function of hexameric helicases," Annual Review of Biochemistry, vol. 69, pp. 651-697, 2000.
Poh, et al., "Oligomerization of the SPP1 scaffold protein," Journal of Molecular Biology, vol. 378, No. 3, pp. 551-564, 2008.
Prevelige, Jr. et al., "Scaffolding protein regulates the polymerization of P22 coat subunits into icosahedral shells in vitro," Journal of Molecular Biology, vol. 202, No. 4, pp. 743-757, 1988.
Provencher, et al., "Estimation of globular protein secondary structure from circular dichroism," Biochemistry, vol. 20, No. 1, pp. 33-37, 1981.
Rao, et al., "DNA packaging in bacteriophage T4," Viral Genome Packaging Machines: Genetics, Structure and Mechanism, pp. 40-58, 2005.
Rao, et al., "DNA packaging of bacteriophage T4 proheads in vitro. Evidence that prohead expansion is not coupled to DNA packaging," Journal of Molecular Biology, vol. 185, No. 3, pp. 565-578, 1985.
Rao, et al., "The bacteriophage DNA packaging motor," Annual Review of Genetics, vol. 42, pp. 647-681, 2008.
Rawlings, et al., "MEROPS: the Peptidase Database," Nucleic Acids Research, vol. 38, Database issue, pp. D227-D233, 2010.
Rinner, et al., "Identification of cross-linked peptides from large sequence databases," Nature Methods, vol. 5, No. 4, pp. 315-318, 2008.
Rishovd, et al., "Bacteriophage P2 and P4 morphogenesis: identification and characterization of the portal protein," Virology, vol. 200, No. 2, pp. 744-751, 1994.
Salunke, et al., "Polymorphism in the Assembly of Polyomavirus Capsid Protein VP1," Biophysical Journal, vol. 56, No. 5, pp. 887-900, 1989.
Salunke, et al., "Self-assembly of purified polyomavirus capsid protein VP1," Cell, vol. 46, No. 6, pp. 895-904, 1986.
Santoro, et al., "A Test of the Linear Extrapolation of Unfolding Free Energy Changes over an Extended Denaturant Concentration Range," Biochemistry, vol. 31, No. 20, pp. 4901-4907, 1992.
Santoro, et al., "Unfolding Free Energy Changes Determined by the Linear Extrapolation Method. 1. Unfolding of Phenylmethanesulfonyl Alpha-Chymotrypsin Using Different Denaturants," Biochemistry, vol. 27, No. 21, pp. 8063-8068, 1988.
Schellman, "Temperature, Stability, and the Hydrophobic Interaction," Biophysical Journal, vol. 73, No. 6, pp. 2960-2964, 1997.
Schmidt, et al., "Dimerization and activation of the herpes simplex virus type 1 protease," Journal of Biological Chemistry, vol. 272, No. 12, pp. 7732-7735, 1997.
Schuck, "On the analysis of protein self-association by sedimentation velocity analytical ultracentrifugation," Analytical Biochemistry, vol. 320, No. 1, pp. 104-124, 2003.
Schuck, "Size-distribution analysis of macromolecules by sedimentation velocity ultracentrifugation and Lamm equation modeling," Biophysical Journal, vol. 78, No. 3, pp. 1606-1619, 2000.
Serwer, "Models of bacteriophage DNA packaging motors," Journal of Structural Biology, vol. 141, No. 3, pp. 179-188, 2003.
Serwer, "T3/T7 DNA packaging," Viral Genome Packaging Machines: Genetics, Structure and Mechanism, pp. 59-79, 2016.
Shenk, "Adenoviridae: the viruses and their replication," In Fields Virology, vol. 2, pp. 2111-2148, 1996.
Signer, et al., "Recombination in bacteriophage lambda: 1. Mutants deficient in general recombination," Journal of Molecular Biology, vol. 34, No. 2, pp. 261-271, 1968.
Singh, et al., "Characterization of protein cross-links via mass spectrometry and an open-modification search strategy," Analytical Chemistry, vol. 80, No. 22, pp. 8799-8806, 2008.
Smith, et al., "The bacteriophage phi29 portal motor can package DNA against a large internal force," Nature, vol. 413, No. 6857, pp. 748-752, 2001.
Stellwagen, "Gel filtration," Methods in Enzymology, Guide to Protein Purification, vol. 182, pp. 317-328, 1990.
Sternberg, et al., "Display of peptides and proteins on the surface of bacteriophage lambda," Proceedings of the National Academy of Sciences USA, vol. 92, No. 5, pp. 1609-1613, 1995.
Sternberg, et al., "In vitro packaging of a lambda Dam vector containing EcoRI DNA fragments of *Escherichia coli* and phage P1," Gene, vol. 1, No. 3-4, pp. 255-280, 1977.

(56) References Cited

OTHER PUBLICATIONS

Sternberg, et al., "Packaging of Coliphage Lambda DNA: II. The Role of the Gene D Protein," Journal of Molecular Biology, vol. 117, No. 3, pp. 733-759, 1977.

Steven, et al., "Virus Maturation: Dynamics and Mechanism of a Stabilizing Structural Transition that Leads to Infectivity," Current Opinion in Structural Biology, vol. 15, No. 2, pp. 227-236, 2005.

Sun, et al., "Structure of the coat protein-binding domain of the scaffolding protein from a double-stranded DNA virus," Journal of Molecular Biology, vol. 297, No. 5, pp. 1195-1202, 2000.

Sunk et al., "The structure of the ATPase that powers DNA packaging into bacteriophage T4 capsids," Molecular Cell, vol. 25, No. 6, pp. 943-949, 2007.

Taylor, et al., "Large-Scale, pH-Dependent, Quaternary Structure Changes in an RNA Virus Capsid Are Reversible in the Absence of Subunit Autoproteolysis," Journal of Virology, vol. 76, No. 19, pp. 9972-9980, 2002.

Tomizawa, et al., "Replication of phage lambda DNA," Cold Spring Harbor Symposia on Quantitative Biology, vol. 33, pp. 533-551, 1968.

Tomka, et al., "Kinetic characterization of the ATPase activity of the DNA packaging enzyme from bacteriophage lambda," Biochemistry, vol. 32, No. 45, pp. 11992-11997, 1993.

Tomka, et al., "Physical and kinetic characterization of the DNA packaging enzyme from bacteriophage lambda," Journal of Biological Chemistry, vol. 268, No. 5, pp. 3056-3065, 1993.

Tsay, et al., "The Q motif of a viral packaging motor governs its force generation and communicates ATP recognition to DNA interaction," Proceedings of the National Academy of Sciences USA, vol. 106, No. 34, pp. 14355-14360, 2009.

Tuma, et al., "Detection of intermediates and kinetic control during assembly of bacteriophage P22 procapsid," Journal of Molecular Biology, vol. 381, No. 5, pp. 1395-1406, 2008.

Tzlil, et al., "Forces and Pressures in DNA Packaging and Release from Viral Capsids," Biophysical Journal, vol. 84, No. 3, pp. 1616-1627, 2003.

Wang, et al., "Assembly of bacteriophage P2 and P4 procapsids with internal scaffolding protein," Virology, vol. 348, No. 1, pp. 133-140, 2006.

Wang, et al., "*Escherichia coli* signal peptide peptidase A is a serine-lysine protease with a lysine recruited to the nonconserved amino-terminal domain in the S49 protease family," Biochemistry, vol. 47, No. 24, pp. 6361-6369, 2008.

Wendt, et al., "A fragile lattice: replacing bacteriophage's head stability gene D with the shp gene of phage 21 generates the $Mg^{2+}$-dependent virus, λ shp," Virology, vol. 326, No. 1, pp. 41-46, 2004.

Werbeck, et al., "Coupling and dynamics of subunits in the hexameric AAA+ chaperone ClpB," Journal of Molecular Biology, vol. 378, No. 1, pp. 178-190, 2008.

Whitmore, et al., "Dichroweb, an online server for protein secondary structure analyses from circular dichroism spectroscopic data," Nucleic Acids Research, vol. 32, Web Server issue, pp. W668-W673, 2004.

Woods, et al., "Kinetic analysis of the endonuclease activity of phage lambda terminase: assembly of a catalytically-competent nicking complex is rate-limiting," Biochemistry, vol. 36, No. 19, pp. 5777-5785, 1997.

Woods, et al., "Kinetic characterization of the GTPase activity of phage lambda terminase: evidence for communication between the two "NTPase" catalytic sites of the enzyme," Biochemistry, vol. 38, No. 44, pp. 14624-14630, 1999.

Yamagishi, et al., "Visualization of the intracellular development of bacteriophage lambda, with special reference to DNA packaging," Proceedings of the National Academy of Sciences USA, vol. 75, No. 7, pp. 3206-3210, 1978.

Yanagi, et al., "Destabilization of Herpes Simplex Virus Type 1 Virions by Local Anesthetics, Alkaline pH, and Calcium Depletion," Archives of Virology, vol. 108, No. 1, pp. 151-159, 1989.

Yang, et al., "A minimal kinetic mechanism for a viral DNA packaging machine," Biochemistry, vol. 43, No. 2, pp. 289-299, 2004.

Yang, et al., "Biochemical characterization of bacteriophage lambda genome packaging in vitro," Virology, vol. 305, No. 2, pp. 276-287, 2003.

Yang, et al., "Cloning, expression, and characterization of a DNA binding domain of gpNu1, a phage lambda DNA packaging protein," Biochemistry, vol. 38, No. 1, pp. 465-477, 1999.

Yang, et al., "Kinetic Analysis of the Genome Packaging Reaction in Bacteriophage Lambda," Biochemistry, vol. 48, No. 45, pp. 10705-10715, 2009.

Yang, et al., "Novel Fold and Capsid-Binding Properties of the Lambda Phage Display Platform Protein gpD," Nature Structural Biology, vol. 7, No. 3, pp. 230-237, 2000.

Yang, et al., "Packaging of a Unit-Length Viral Genome: The Role of Nucleotides and the gpD Decoration Protein in Stable Nucleocapsid Assembly in Bacteriophage Lambda," Journal of Molecular Biology, vol. 383, No. 5, pp. 1037-1048, 2008.

Zeng et al., "Following Cell-fate in *E. coli* After Infection by Phage Lambda," Journal of Visualized Experiments, vol. 56, e3363, 2011.

Zhang, et al., "A Promiscuous DNA Packaging Machine from Bacteriophage T4," PLoS Biology, vol. 9, No. 2, e1000592, 2011.

Ziegelhoffer, et al., "The purification and properties of the scaffolding protein of bacteriophage lambda," Journal of Biological Chemistry, vol. 267, No. 1, pp. 455-461, 1992.

Zlotnick, "Theoretical aspects of virus capsid assembly," Journal of Molecular Recognition, vol. 18, No. 6, pp. 479-490, 2005.

Zlotnick, et al., "Mechanisms of icosahedral virus assembly," Structural Virology, vol. 21, pp. 182-204. 2011.

Alonso, et al., "Bacteriophage SPP1," In the Bacteriophages, 2nd edit., pp. 331-349, 2006.

Alvarez, et al., "Propagation of Fluorescent Viruses in Growing Plaques," Biotechnology and Bioengineering, vol. 96, No. 3, pp. 615-621, 2007.

Aramayo, et al., "Divalent Ion-Dependent Swelling of Tomato Bushy Stunt Virus: A Multi-Approach Study," Biochimica et Biophysica Acta, vol. 1724, No. 3, pp. 345-354, 2005.

Baines, "Cleavage and Packaging of Herpes Simplex Virus 1 DNA," Viral Genome Packaging Machines: Genetics, Structure, and Mechanism, pp. 135-149. Kluwer Academic/Plenum Publishers. New York, N.Y., 2005.

Baines, et al., "Nucloeocapsid Assembly and Envelopment of Herpes Simplex Virus," Alpha Herpesviruses: Molecular and Cellular Biology, pp. 175-204, 2006.

Baldwin, "Temperature Dependence of the Hydrophobic Interaction in Protein Folding," Proceedings of the National Academy of Sciences USA, vol. 83, No. 21, pp. 8069-8072, 1986.

Barrett, et al., "The Merops database as a protease information system," Journal of Structural Biology, vol. 134, No. 2-3, pp. 95-102, 2001.

Becker, et al., "Bacteriophage lambda DNA: the beginning of the end," Journal of Bacteriology, vol. 172, No. 6, pp. 2819-2824, 1990.

Beghetto, et al., "Lambda Display: A Powerful Tool for Antigen Discovery," Molecules, vol. 16, No. 4, pp. 3089-3105, 2011.

Black, "DNA Packaging in dsDNA Bacteriophages," Annual Review of Microbiology, vol. 43, pp. 267-292, 1989.

Bode, et al., "Distinct Effects of Diamines, Polyamines, and Magnesium ions on the Stability of Lambda Phage Heads," Biochemistry, vol. 12, No. 17, pp. 3193-3196, 1973.

Bolen, et al., "Unfolding free energy changes determined by the linear extrapolation method. 2. Incorporation of delta G degrees N-U values in a thermodynamic cycle," Biochemistry, vol. 27, No. 21, pp. 8069-8074, 1988.

Brady, et al., "Dissociation of Polyoma Virus by the Chelation of Calcium Ions Found Associated with Purified Virions," Journal of Virology, vol. 23, No. 3, pp. 717-724, 1977.

Buisson, et al., "The crystal structure of the Epstein-Barr virus protease shows rearrangement of the processed C terminus," Journal of Molecular Biology, vol. 324, No. 1, pp. 89-103, 2002.

Campbell, "Sensitive mutants of bacteriophage lambda," Virology, vol. 14, No. 1, pp. 22-32, 1961.

(56) References Cited

OTHER PUBLICATIONS

Casjens et al., "Locations and amounts of the major structural proteins in bacteriophage lambda," Journal of Molecular Biology, vol. 88, No. 2, pp. 535-545, 1974.
Caspar, "Movement and self-control in protein assemblies. Quasi-equivalence revisited," Biophysical Journal, vol. 32, No. 1, pp. 103-138, 1980.
Caspar, et al., "Physical principles in the construction of regular viruses," Cold Spring Harbor Symposia on Quantitative Biology, vol. 27, pp. 1-24, 1962.
Catalano, "The terminase enzyme from bacteriophage lambda: a DNA-packaging machine," Cellular and Molecular Life Sciences, vol. 57, No. 1, pp. 128-148, 2000.
Catalano, "Viral Genome Packaging Machines: An Overview," Viral Genome Packaging Machines: Genetics, Structure, and Mechanism, pp. 1-4, 2005.
Cerritelli, et al., "Assembly of T7 capsids from independently expressed and purified head protein and scaffolding protein," Journal of Molecular Biology, vol. 258, No. 2, pp. 286-298, 1996.
Chang, et al., "Functional domains of the bacteriophage P2 scaffolding protein: identification of residues involved in assembly and protease activity," Virology, vol. 384, No. 1, pp. 144-150, 2009.
Chang, et al., "Incorporation of scaffolding protein gpO in bacteriophages P2 and P4," Virology, vol. 370, No. 2, pp. 352-361, 2008.
Cheng, et al., "Double-stranded DNA bacteriophage prohead protease is homologous to herpesvirus protease," Protein Science, vol. 13, No. 8, pp. 2260-2269, 2004.
Cho, et al., "Assessing energetic contributions to binding from a disordered region in a protein-protein interaction," Biochemistry, vol. 49, No. 43, pp. 9256-9268, 2010.
Coffman, et al., "Protein diffusion in porous chromatographic media studied by proton and fluorine PFG-NMR," Journal of Physical Chemistry B, vol. 101, No. 12, pp. 2218-2223, 1997.
Compton, et al., "Analysis of protein circular dichroism spectra for secondary structure using a simple matrix multiplication," Analytical Biochemistry, vol. 155, No. 1, pp. 155-167, 1986.
Conway, et al., "A Thermally Induced Phase Transition in a Viral Capsid Transforms the Hexamers, Leaving the Pentamers Unchanged," Journal of Structural Biology, vol. 158, No. 2, pp. 224-232, 2007.
Conway, et al., "Proteolytic and Conformational Control of Virus Capsid Maturation: The Bacteriophage HK97 System," Journal of Molecular Biology, vol. 253, No. 1, pp. 86-99, 1995.
Cue, et al., "A site required for termination of packaging of the bacteriophage lambda chromosome," Proceedings of the National Academy of Sciences USA, 90(20):9290-9294, 1993.
Cue, et al., "Genetic evidence that recognition of cosQ, the signal for termination of phage lambda DNA packaging, depends on the extent of head filling," Genetics, vol. 147, No. 1, pp. 7-17, 1997.
Cue, et al., "Termination of packaging of the bacteriophage lambda chromosome: cosQ is required for nicking the bottom strand of cosN," Journal of Molecular Biology, vol. 280, No. 1, pp. 11-29, 1998.
Daniels, et al., "Complete annotated lambda sequence," Lambda II, pp. 520-676, 1983.
Darke, et al., "Active human cytomegalovirus protease is a dimer," Journal of Biological Chemistry, vol. 271, No. 13, pp. 7445-7449, 1996.
Database UniProt, "SubName: Full=Head decoration protein," Online, 1 page, 2012.
Davidson, et al., "A novel in vitro DNA packaging system demonstrating a direct role for the bacteriophage lambda Fl gene product," Virology, vol. 161, No. 2, pp. 305-314, 1987.
De La Torre, et al., "Hydrodynamic properties of macromolecular complexes. I. Translation," Biopolymers, vol. 16, No. 8, pp. 1747-1763, 1977.
Demeler, et al., "Identification and interpretation of complexity in sedimentation velocity boundaries," Biophysical Journal, vol. 72, No. 1, pp. 397-407, 1997.
Demeler, et al., "Sedimentation velocity analysis of highly heterogeneous systems," Analytical Biochemistry, vol. 335, No. 2, pp. 279-288, 2004.
Dokland, "Scaffolding Proteins and their Role in Viral Assembly," Cellular and Molecular Life Sciences, vol. 56, No. 7-8, pp. 580-603, 1999.
Dokland, et al., "Structural Transitions During Maturation of Bacteriophage Lambda Capsids," Journal of Molecular Biology, vol. 233, No. 4, pp. 682-694, 1993.
Dubendorff, et al., "Controlling basal expression in an inducible T7 expression system by blocking the target T7 promoter with lac repressor," Journal of Molecular Biology, vol. 219, No. 1, pp. 45-59, 1991.
Duda, et al., "Structural Transitions During Bacteriophage HK97 Head Assembly," Journal of Molecular Biology, vol. 247, No. 4, pp. 618-635, 1995.
Dyson, et al., "Intrinsically unstructured proteins and their functions," Nature Reviews: Molecular Cell Biology, vol. 6, No. 3, pp. 197-208, 2005.
Earnshaw, et al., "DNA packaging by the double-stranded DNA bacteriophages," Cell, vol. 21, No. 2, pp. 319-331, 1980.
Edelhoch, "Spectroscopic determination of tryptophan and tyrosine in proteins," Biochemistry, vol. 6, No. 7, pp. 1948-1954, 1967.
Ekici, et al., "Unconventional serine proteases: variations on the catalytic Ser/His/Asp triad configuration," Protein Science, vol. 17, No. 12, pp. 2023-2037, 2008.
Enemark, et al., "On helicases and other motor proteins," Current Opinion in Structural Biology, vol. 18, No. 2, pp. 243-257, 2008.
Evilevitch, et al., "Osmotic Pressure Inhibition of DNA Ejection from Phage," Proceedings of the National Academy of Sciences USA, vol. 100, No. 16, pp. 9292-9295, 2003.
Fane, et al., "Mechanism of Scaffolding-Assisted Viral Assembly," Advances in Protein Chemistry, vol. 64, pp. 259-299, 2003.
Feiss, et al., "Bacteriophage Lambda Terminase and the Mechanism of Viral DNA Packaging," Viral Genome Packaging Machines: Genetics. Structure, and Mechanism, pp. 5-39, 2005.
Filutowicz, et al., "Purification of the *Escherichia coli* Integration Host Factor (IHF) in One Chromatographic Step," Gene, vol. 147, No. 1, pp. 149-150, 1994.
Frackman, et al., "A functional domain of bacteriophage lambda terminase for prohead binding," Journal of Molecular Biology, vol. 180, No. 2, pp. 283-300, 1984.
Friedman, et al., "Lytic mode of lambda development," Lambda II, pp. 21-52, 1983.
Fu, et al., "Molecular dissection of phi29 scaffold protein function in an in vitro assembly system," Journal of Molecular Biology, vol. 366, No. 4, pp. 1161-1173, 2007.
Fujisawa, et al., "Phage DNA packaging," Genes to Cells, vol. 2, No. 9, pp. 537-545, 1997.
Fuller, et al., "Ionic effects on Viral DNA Packaging and Portal Motor Function in Bacteriophage phi29," Proceedings of the National Academy of Sciences USA, vol. 104, No. 27, pp. 11245-11250, 2007.
Fuller, et al., "Measurements of single DNA molecule packaging dynamics in bacteriophage lambda reveal high forces, high motor processivity, and capsid transformations," Journal of Molecular Biology, vol. 373, No. 5, pp. 1113-1122, 2007.
Fuller, et al., "Single phage T4 DNA packaging motors exhibit large force generation, high velocity, and dynamic variability," Proceedings of the National Academy of Sciences USA, vol. 104, No. 43, pp. 16868-16873, 2007.
Furth, et al., "Lambda DNA replication," Lambda II, pp. 145-174, 1983.
Galisteo, et al., "Conformational Transformations in the Protein Lattice of Phage P22 Procapsids," Biophysical Journal, vol. 65, No. 1, pp. 227-235, 1993.
Gaussier, et al., "Building a virus from scratch: assembly of an infectious virus using purified components in a rigorously defined biochemical assay system," Journal of Molecular Biology, vol. 357, No. 4, pp. 1154-1166, 2006.
Georgopoulos, et al., "Lambdoid Phage Head Assembly," Lambda II, pp. 279-304, 1983.

(56) References Cited

OTHER PUBLICATIONS

Gertsman, et al., "An Unexpected Twist in Viral Capsid Maturation," Nature, vol. 458, No. 7238, pp. 646-650, 2009.
Gertsman, et al., "Critical Salt Bridges Guide Capsid Assembly, Stability, and Maturation Behavior in Bacteriophage HK97," Molecular & Cellular Proteomics, vol. 9, No. 8, pp. 1752-1763, 2010.
Grayson, et al., "The effect of genome length on ejection forces in bacteriophage lambda," Virology, vol. 348, No. 2, pp. 430-436, 2006.
Hamada, et al., "A defined in vitro system for packaging of bacteriophage T3 DNA," Virology, vol. 151, No. 1, pp. 119-123, 1986.
Hang, et al., "ATPase center of bacteriophage lambda terminase involved in post-cleavage stages of DNA packaging: identification of ATP-interactive amino acids," Journal of Molecular Biology, vol. 302, No. 4, pp. 777-795, 2000.
Hang, et al., "Cloning, expression, and biochemical characterization of hexahistidine-tagged terminase proteins," Journal of Biological Chemistry, vol. 274, No. 22, pp. 15305-15314, 1999.
Hendrix, "Bacteriophage HK97: assembly of the capsid and evolutionary connections," Advances in Virus Research, vol. 64, pp. 1-14, 2005.
Hendrix, et al., "Assembly of bacteriophage lambda heads: protein processing and its genetic control in petit lambda assembly," Journal of Molecular Biology, vol. 91, No. 2, pp. 187-199, 1975.
Hendrix, et al., "Bacteriophage Lambda and its Genetic Neighborhood," The Bacteriophages, 2nd edit., pp. 409-447. Oxford University Press, New York, N.Y., 2006.
Hingorani, et al., "Cooperative interactions of nucleotide ligands are linked to oligomerization and DNA binding in bacteriophage T7 gene 4 helicase," Biochemistry, vol. 35, No. 7, pp. 2218-2228, 1996.
Hohn, et al., "Capsid Transformation During Packaging of Bacteriophage Lambda DNA," Philosophical Transactions of the Royal Society of London, Series B, Biological Sciences, vol. 276, No. 943, pp. 51-61, 1976.
Hohn, et al., "Petit lambda, a family of particles from coliphage lambda infected cells," Journal of Molecular Biology, vol. 98, No. 1, pp. 107-120, 1975.
Hohn, et al., "The Capsid Protein of Bacteriophage Lambda and of its Prehead," Journal of Molecular Biology, vol. 105, No. 2, pp. 337-342, 1976.
Hwang, et al., "A defined system for in vitro lambda DNA packaging," Virology, vol. 211, No. 2, pp. 367-376, 1995.
Imber, et al., "Outer Surface Protein of Bacteriophage Lambda," Journal of Molecular Biology, vol. 139, No. 3, pp. 277-295, 1980.
Iwai, et al., "NMR Solution Structure of the Monomeric Form of the Bacteriophage Lambda Capsid Stabilizing Protein gpD," Journal of Biomolecular NMR, vol. 31, No. 4, pp. 351-356, 2005.
Jardine, DNA Packaging in Double-Stranded DNA Phages, The Bacteriophages, 2nd edit., pp. 49-65. Oxford University Press, New York, N.Y., 2006.
Jardine, et al., "Capsid Expansion Follows the Initiation of DNA Packaging in Bacteriophage T4," Journal of Molecular Biology, vol. 284, No. 3, pp. 661-672, 1998.
Johnson, "Virus Particle Maturation: Insights into Elegantly Programmed Nanomachines," Current Opinion in Structural Biology, vol. 20, No. 2, pp. 210-216, 2010.
Johnson, et al., "Quasi-Equivalent Viruses: A Paradigm for Protein Assemblies," Journal of Molecular Biology, vol. 269, No. 5, pp. 665-675, 1997.
Kainov, et al., "Structural basis of mechanochemical coupling in a hexameric molecular motor," Journal of Biological Chemistry, vol. 283, No. 6, pp. 3607-3617, 2008.
Kaiser, et al., "Processing and assembly of the head of bacteriophage lambda," Journal of Supramolecular Structure, vol. 2, No. 2-4, pp. 318-328, 1974.
Kelley, et al., "Protein structure prediction on the Web: a case study using the Phyre server," Nature Protocols, vol. 4, No. 3, pp. 363-371, 2009.
Kemp, et al., "Electron microscopy studies of mutants of lambda bacteriophage. I. General description and quantitation of viral products," Virology, vol. 36, No. 3, pp. 490-502, 1968.
Kim, et al., "Crystal structure of a bacterial signal peptide peptidase," Journal of Molecular Biology, vol. 376, No. 2, pp. 352-366, 2008.
Kochan, et al., "Early Intermediates in Bacteriophage Lambda Prohead Assembly. II. Identification of Biologically Active Intermediates," Virology, vol. 131, No. 1, pp. 100-115, 1983.
Krüse, et al., "Divalent Metal Ion-Dependent Reversible Swelling of Tomato Bushy Stunt Virus and Organization of the Expanded Virion," Journal of Molecular Biology, vol. 162, No. 2, pp. 393-414, 1982.
Künzler, et al., "Stages of Bacteriophage Lambda Head Morphogenesis: Physical Analysis of Particles in Solution," Journal of Molecular Biology, vol. 122, No. 2, pp. 191-215, 1978.
Lander et al., "Bacteriophage Lambda Stabilization by Auxiliary Protein gpD: Timing, Location, and Mechanism of Attachment Determined by Cryo-EM," Structure, vol. 16, No. 9, pp. 1399-1406, 2008.
Lata, et al., "Maturation Dynamics of a Viral Capsid: Visualization of Transitional Intermediate States," Cell, vol. 100, No. 2, pp. 253-263, 2000.
Lee, et al., "Cooperative Reorganization of a 420 Subunit Virus Capsid," Journal of Molecular Biology, vol. 352, No. 3, pp. 723-735, 2005.
Lee et al., "Sequential interactions of structural proteins in phage phi 29 procapsid assembly," Journal of Virology, vol. 69, No. 8, pp. 5024-5032, 1995.
Licht, et al., "Resolving individual steps in the operation of ATP-dependent proteolytic molecular machines: from conformational changes to substrate translocation and processivity," Biochemistry, vol. 47, No. 12, pp. 3595-3605, 2008.
Liljas, "The Structure of Spherical Viruses," Progress in Biophysics and Molecular Biology, vol. 48, No. 1, pp. 1-36, 1986.
Lin, et al., "An efficient method to purify active eukaryotic proteins from the inclusion bodies in *Escherichia coli*," Biotechniques, vol. 11, No. 6, pp. 748, 750, 752-753, 1991.
Liu, et al., "Displacements of prohead protease genes in the late operons of double-stranded DNA bacteriophages," Journal of Bacteriology, vol. 186, No. 13, pp. 4369-4375, 2004.
Makhatadze, et al., "Protein Interactions with Urea and Guanidinium Chloride: A Calorimetric Study," Journal of Molecular Biology, vol. 226, No. 2, pp. 491-505, 1992.
Parent, et al., "Quantitative Analysis of Multi-component spherical virus assembly: scaffolding protein contributes to the Global Stability of Phage P22 Procapsids," J. Mol. Biol. (2006) 359:1097-1106.
Morias, et al., "Bacteriophage 29 scaffolding protein gp7 before and after prohead assembly," Nature Structural Biology (Jul. 2003) 10(7): 572-576.
Perucchetti, et al., "Late Stages in Bacteriophage [gamma] head morphogenesis: In vitro studies on the action of the bacteriophage [gamma] D-gene and W-gene products," Virology (1988) 165: 103-114.
Sussman, et al., "[On a thermosensitive repression system in the *Escherichia coli* lambda bacteriophage]," Comptes Rendus Hebdomadaires des Seances de l'Academie des Sciences, (1962) vol. 254, pp. 1517-1519, (article in French, machine translation of abstract provided at end of document).

A

THERAGNOSTIC PARTICLES

RELATED APPLICATIONS

This application is a U.S. national phase of International Application No. PCT/US2014/012206, filed on Jan. 20, 2014, which claims priority to U.S. Provisional Application No. 61/754,458, filed Jan. 18, 2013, both of which are incorporated by reference herein in their entirety.

FEDERAL FUNDING STATEMENT

This invention was made with U.S. government support under MCB-0648617, awarded by the National Science Foundation. The U.S. Government has certain rights in the invention.

BACKGROUND

Viral-based particle systems can be modified to present a high density of ligands in a defined symmetric pattern; this type of display can increase the avidity of binding to target biomolecules. For example, bacteriophage lambda has been used for phage display applications through peptide fusions with either the major tail protein (gpV) or the gpD decoration protein (Maruyama et al., 1994; Mikawa et al., 1996). Studies have shown that gpD may be modified at either the N- or C-terminus to present peptides at the capsid surface for phage display applications. However, all current phage based display systems are limited by the required construction of decoration or major capsid protein fusion constructs within the context of an infectious viral particle, while the constructs have been constructed in vivo, thus limiting these systems to peptide and protein fusion constructs expressed within infected cells in the context of an infectious virus. As a result, the stoichiometry of the fusion proteins cannot be controlled on the resulting infectious viral particles, the modified constructs are limited to peptide and protein display ligands, and the fusion proteins are limited to fusions at the N- or C-terminus of the decoration protein.

SUMMARY OF THE INVENTION

In one aspect, the present invention provides theragnostic particles, comprising a plurality of engineered decoration proteins bound to an outer surface of decoration competent viral particle shell, wherein the engineered decoration proteins comprise decoration proteins linked to one or more compound not naturally occurring on a wild type viral capsid, and wherein the one or more compounds have at least one feature selected from the group consisting of:

(a) the one or more compounds are non-proteinaceous compounds;

(b) the one or more compounds are present on the theragnostic particle in a defined ratio relative to the engineered decoration protein;

(c) the one or more compounds comprise two or more different compounds, wherein the two or more different compounds are present on the theragnostic particle in a defined ratio relative to each other; and (d) the one or more compounds are linked to the engineered decoration protein at a site on the engineered decoration protein other than the N-terminus or the C-terminus.

In another aspect, the invention provides pharmaceutical composition, comprising the theragnostic particles of the invention and a pharmaceutically acceptable carrier.

In a further aspect, the invention provides an isolated recombinant protein comprising the amino acid sequence of SEQ ID NO: 10 (gpD(S42C)), as well as gpD S42C linked to one or more compounds of interest. The invention also provide isolated nucleic acids encoding the isolated protein, recombinant expression vectors comprising the isolated nucleic acids, and isolated host cells comprising the recombinant expression vectors of the invention.

In another aspect, the invention provides an in vitro method for preparing a theragnostic particle, comprising decorating a decoration competent viral particle shell in vitro with a defined amount of engineered decoration proteins linked to one or more compounds, wherein the engineered decoration proteins stabilize the decoration competent viral particle shell to produce a theragnostic particle.

DETAILED DESCRIPTION OF THE INVENTION

Figure 1:
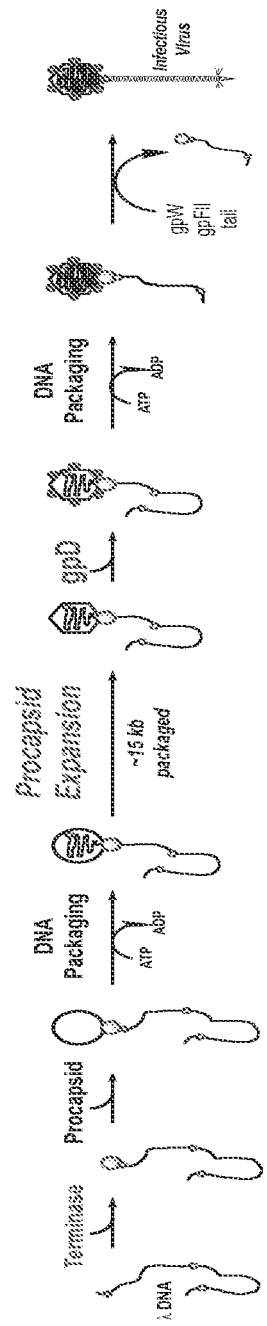
FIG. 1. Phage Lambda Assembly Pathway. A multigenome concatemer is depicted, which serves as the preferred DNA packaging substrate in vivo. Details of the packaging pathway are provided in the Example 1.

It must be noted that, as used in the specification, the singular forms "a," "an" and "the" include plural referents unless the context clearly dictates otherwise.

Any terms not directly defined herein shall be understood to have the meanings commonly associated with them as understood within the art of the present disclosure. Certain terms are discussed herein to provide additional guidance to the practitioner in describing the compositions, devices, methods, and the like, of embodiments of the present disclosure, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the present disclosure herein.

As used herein, "about" means +/−10% of the recited value.

All embodiments disclosed herein can be used in combination, unless the context clearly indicates otherwise. Unless the context clearly requires otherwise, throughout the description and the claims, the words 'comprise', 'comprising', and the like are to be construed in an inclusive sense, as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure. Persons skilled in the relevant art can appreciate that many modifications and variations are possible in light of the embodiment teachings. Accordingly, the disclosure is intended to be illustrative, but not limiting, of the scope of invention.

In a first aspect the present invention provides an in vitro method for preparing a theragnostic particle, comprising decorating a decoration competent viral particle shell in vitro with a defined amount of engineered decoration proteins linked to one or more compounds, wherein the engineered decoration proteins stabilize the decoration competent viral particle shell to produce a theragnostic particle.

The present invention overcomes the shortcomings of viral particle systems in the art, which did not permit capsid decoration with a defined amount of engineered decoration proteins linked to compounds of interest. The methods of the present invention permit construction of theragnostic (i.e.: can be used for therapeutic or diagnostic use) particles decorated with defined amounts of engineered decoration protein, and where the engineered decoration proteins are linked to any compound or multiple compounds of interest including non-proteinaceuous compounds, which can themselves be added in defined amounts to the resulting viral particle. Further, the engineered decoration proteins of the invention can be modified at any suitable position on the protein that does not interfere with binding to the expanded viral particle shell. As such, the theragnostic particles made by the methods of the invention can be used for any suitable therapeutic or diagnostic purpose, as described in more detail herein. In one embodiment, the expanded viral particle shells are decorated with a stoichiometric ratio of engineered decoration proteins.

As used herein, the "viral particle" is a protein shell of a virus (capsid) or virus-like particle. For use in the present invention, the viral particles are based on capsids of double stranded DNA viruses that normally package their genome into preassembled procapsid shells. Packaging in these viruses triggers a major re-orientation and expansion of the proteins assembled into the procapsid shells, yielding the mature capsid shell that is subsequently stabilized with the addition of decoration proteins. Exemplary such double stranded DNA viruses include, but are not limited to bacteriophages lambda, T4, 21, L, P4, herpesvirus and adenoviruses.

The viral particle can be an isolated capsid or may be produced by any suitable means, such as recombinant expression of the structural proteins and subsequent viral particle assembly using the recombinantly expressed structural proteins in vitro; in the latter case the particles are known as virus-like particles (VLP). In one embodiment, described in more detail in the examples that follow, vectors can be designed to express all proteins required to assemble a functional capsid in a host cell, such as *E. coli*, and the particle can then be purified. The viral particle may comprise or consist of wild type or mutated capsid structural proteins, so long as the mutated structural proteins can form the engineered viral particle (e.g., functional mutant structural proteins). The viral particles may be isolated and stored or preassembled and stored, or may be isolated or assembled at the time of carrying out the methods of the invention. Assembly or isolation can be carried out by any suitable means, which are well within the level of skill in the art based on the disclosure herein. Exemplary isolation and assembly techniques are provided in the examples that follow.

In one embodiment, a virus-like particle is produced by in vitro assembly of isolated capsid structural proteins. The capsid structural proteins to be used will depend on the virus that the viral particle is based on. Capsid structural proteins for each of bacteriophages lambda, T4, L, P22, 21, and P4 and for the eukaryotic adenovirus and herpesviruses are well known to those of skill in the art, as are methods for their recombinant production or isolation. In one non-limiting embodiment, a lambda phage viral particle is used. In this embodiment, the structural proteins may be portal protein gpB (SEQ ID: 1) and major capsid protein gpE (SEQ ID: 2), and the minor capsid protein gpC (SEQ ID: 3), or the scaffolding protein contained therein (SEQ ID NO: 36; residues 309 to 439 of SEQ ID NO:3), or functional mutants thereof.

In another embodiment, a bacteriophage T4 viral particle is used; in this embodiment, the structural proteins are the T4 structural proteins, or functional mutants thereof. In a further embodiment, a bacteriophage L viral particle is used; in this embodiment, the structural proteins are the bacteriophage L structural proteins, or functional mutants thereof. In another embodiment, a bacteriophage P22 viral particle is used; in this embodiment, the structural proteins are the bacteriophage p22 structural proteins, or functional mutants thereof. In another embodiment, a bacteriophage 21 viral particle is used; in this embodiment, the structural proteins are the bacteriophage 21 structural proteins, or functional mutants thereof. In a further embodiment, a bacteriophage P4 viral particle is used; in this embodiment, the structural proteins are the bacteriophage P4 structural proteins, or functional mutants thereof. The structural proteins and their amino acid sequences for each of these viral structural proteins known to those of skill in the art.

The viral particle is "decoration competent" in that the particle is either (a) prepared or isolated in a form that can add decoration protein to the shell without further manipulation, (b) contacted with an expansion agent in vitro under conditions and for a time suitable to produce an expanded viral particle shell. that will be stabilized in the expanded state by decoration with the decoration protein, or (c) contacted with an agent in vitro under conditions and for a time suitable to produce a shell that has undergone a conformational change such that it will be stabilized in that conformation state by decoration with the decoration protein. Packaging in phages lambda, T4, 21, P22, and L, DNA triggers major conformational changes that alter the shell morphology and cause shell expansion. The herpesvirses similarly undergo major conformational changes with DNA packaging that alter the shell morphology but they are not typically described as expanding. Purification affords a mixture of pre-change and post-change species in most cases.

Thus, in one embodiment, the viral particle shell has under extensive conformational change that renders the shell competent for decoration with the decoration protein. All procapsids undergo a major structural re-organization of the shell as a result of DNA packaging during the viral particle maturation process. Decoration of the shell with the decoration protein stabilizes this embodiment of a decoration competent viral particle shell.

In another embodiment, the methods involve expanding the viral particle by contacting it with an expansion agent in vitro under conditions and for a time suitable to produce an expanded viral particle shell. Any suitable expansion agent that can expand a specific viral particle can be used, including but not limited to chaotropic agents (including but not limited to urea), pH changes, heating, etc. The methods do not require any specific amount of expansion of the viral particle; the expansion may be similar to the expansion seen upon genome packaging during the normal viral life cycle. Any suitable expansion agent can be used, as deemed most appropriate in light of the specific of the engineered viral particle and all other relevant factors. In one embodiment, a chaotropic agent such as urea is used. In one non-limiting example, when bacteriophage lambda viral particles are used, urea can be used as the chaotropic agent; in this embodiment, the resulting viral particle shell can optionally be contracted and expanded repeatedly if desired. In a further embodiment using bacteriophage lambda viral particles, expansion of the cell is done at about 4° C. In other embodiments, the expansion agent can be heat (range of 4° C. to 50° C.), pH (pH range of 3-9), or other expansion agent. Based on the teachings herein and the specific viral particle being used, those of skill in the art will be able to determine the most appropriate expansion agent for a given use. Similarly, conditions and times suitable to produce the expanded virus shell can be determined by those of skill in the art based on the teachings herein and in light of the specific viral particle being used.

In another embodiment, the methods, agents, and techniques described for particle expansion are applied to driving the conformational change of the shell required to afford a decoration competent particle shell, in those viral capsids that do not undergo particle expansion.

The methods comprise decorating the decoration competent viral particle shells in vitro with engineered decoration proteins. As used herein "decorating" means binding a plurality of decoration proteins to the viral particle shells, such that the decoration proteins stabilize the decoration competent viral particle shell. Since the methods are carried out in vitro, the decoration proteins can be added stochiometrically, in any desired amount to the decoration competent viral particle shells. As is known by those of skill in the art, a variety of double stranded DNA viruses possess decoration proteins that stabilize procapsid shells to produce the mature capsid shell. Non-limiting examples of such decoration proteins include, but are not limited to, the lambda gpD decoration protein, T4 head outer capsid (Hoc) protein, T4 small outer capsid (Soc) protein, Shp protein of phage 21, the Dec protein of phage L, and the Psu protein of phage P4, and protein IX of adenoviruses. The plurality of decoration proteins that are added depend on the viral particle used, the modifications made to the decoration protein, and the intended use of the viral particles, but include enough decoration proteins to bind to at least 80% of the binding sites for the decoration protein that are present on the expanded viral particle shell (e.g.: on the structural proteins defining the shells. In various further embodiments, the engineered decoration proteins bind to at least 85%, 90%, 92%, 94%, 95%, 96%, 97%, 98%, 99% or to all binding sites for the decoration protein that are present on the expanded viral particle shell.

As will be understood by those of skill in the art, the choice of decoration protein will depend on the viral particle/structural proteins being used. Thus, if the viral particle is lambda phage based, lambda phage structural proteins (or functional mutants thereof) and the engineered lambda decoration protein (engineered gpD protein) will be used. The wild type gpD amino acid sequence is shown in SEQ ID: 4. Similarly, if the viral particle is bacteriophage T4 then T4 structural proteins (or functional mutants thereof) and the engineered T4 decoration protein (engineered Hoc or Soc protein) will be used. The wild type Hoc amino acid sequence is shown in SEQ ID:5; The wild type Soc amino acid sequence is shown in SEQ ID:6. If the viral particle is bacteriophage 21, then bacteriophage 21 structural proteins (or functional mutants thereof) and the engineered bacteriophage 21 decoration protein (Shp protein) will be used. The wild type Shp amino acid sequence is shown in SEQ ID:7. If the viral particle is bacteriophage L, then bacteriophage L structural proteins (or functional mutants thereof) and the engineered bacteriophage L decoration protein (Dec protein) will be used. The wild type Dec amino acid sequence is shown in SEQ ID:8. If the viral particle is bacteriophage P22, then bacteriophage P22 structural proteins (or functional mutants thereof) and the engineered bacteriophage L decoration protein (Dec protein) will be used, since P22 does not make a decoration protein in vivo, but can be decorated with Dec from phage L in vitro. If the viral particle is bacteriophage P4, then bacteriophage P4 structural proteins (or functional mutants thereof) and the engineered bacteriophage P4 decoration protein (Psu protein) will be used. The wild type Psu amino acid sequence is shown in SEQ ID:9.

The decoration proteins for use in the methods of the invention are "engineered" in that they are not the wild type proteins, but have been modified and are linked to one or more compounds of interest. Since the methods of the present invention can be carried out in vitro, the decoration proteins can be modified in any desirable way, providing a unprecedented increase in the functionality that can be displayed on the surface of the resulting particles compared to prior art methods. In one embodiment, the decoration proteins have an altered amino acid sequence from wild type, such as an insertion, deletion, one or more substitutions, etc. Non-natural amino acid residues can be incorporated into the engineered decoration proteins as suitable for a given purpose. Any suitable modifications can be made to the decoration proteins so long as the resulting engineered decoration protein can bind to the viral particle shell and stabilize it.

In one non-limiting embodiment, any solvent accessible residue on a shell bound decoration protein can be modified as desired, such as to facilitate linkage to one or more compounds of interest. For example, residues in the shell-bound gpD trimer spike that are exposed to solvent include, but are not limited to Thr1, Ser2, Lys3, Glu4, Thr5, Phe6, Thr7, His8, Tyr9, Gln10, Pro11, Gln12, Gly13, Asn14, Ser15; Gly25, Gly26, Leu27, Ser28, Ala29, Lys30, Ala31; Asp40, Thr41. Ser42, Ser43Arg44, Lys45; Asp49, Gly50, Thr51, Thr52, Asp53; Asp66, Gln67, Thr68, Ser69, Thr70, Thr71; Arg81, Tyr82, Glu83, Asp84; Glu89, Ala90, Ala91, Ser92, Asp93, Glu94, Thr95, Lys96, Lys97, Arg98, Thr99; the N- and C-terminal residues of the protein. In one non-limiting embodiment, one or more residue may be substituted with a Cys residue (including but not limited to an S42C substitution), to facilitate binding of other compounds to the decoration proteins. In another embodiment, a non-natural amino acid, including but not limited to azidohomoalanine (Aha) can be incorporated using genetic manipulation of the gene to allow alternate means for chemical modification of the decoration protein, including "click" chemistry.

Note that the N-terminal methionine shown for gpD in SEQ ID NO 4 is generally excluded from the mature protein by cell degradation. For purposes of this application, the numbering for gpD excludes the (optional) N-terminal methionine. Thus, for example, Ser42 represents the 42 amino acid in the mature gpD sequence (deleted for the N-terminal methionine), but is the 43$^{rd}$ amino acid in the sequence if the N-terminal methionine is counted. The numbering system follows that reported in the crystal structure of gpD (Yang et al, (2000) Nat. Struct. Biol. vol 7, pp. 230) which does not included the N-terminal methionine encoded by the gene sequence.

The engineered decoration proteins comprise engineered decoration proteins linked to one or more compound. In another embodiment, the engineered decoration proteins comprise engineered decoration proteins linked to one or more compound selected from the group consisting of nucleic acids, lipids, carbohydrates, polypeptides, polymers, organic molecules, inorganic molecules, or combinations thereof. In a further embodiment, the engineered decoration proteins comprise engineered decoration proteins linked to one or more non-proteinaceous compound, such as nucleic acids, lipids, carbohydrates, polymers, organic molecules, inorganic molecules (e.g. magnetic beads and quantum dots, among others), or combinations thereof. In all of these embodiments, the linkage can be at any suitable position on the decoration protein, which is not possible using previously known methods (which are limited to engineered fusion proteins, such that linkage is at the N- of C-terminus of the decoration protein). In various embodiments, the linkage can be at the N- or C-terminus of the decoration protein, or at any suitable internal residue of the decoration protein (e.g., other than the N-terminal or C-terminal residue of the decoration protein). Any suitable techniques can be used to link the one or more compounds to the decoration proteins; such techniques are well within the level of those of skill in the art based on the teachings herein. As will be understood by those of skill in the art, any suitable combination of decoration proteins can be used, as appropriate for a given expanded viral particle.

In further embodiments, the one or more compounds may be any suitable compound for the theragnostic particles of the invention, including but not limited to therapeutic compounds, diagnostic compounds, adjuvants, antigens, antibodies, etc.

The decorating comprises contacting the decoration competent viral particle shells in vitro with the engineered decoration proteins for a time and under conditions suitable to bind the decoration proteins to the viral particle shells. The range of viral particle decoration is limited by the initial concentrations of the engineered decoration proteins thereby allowing tunability and precise decorating of the viral particle shell with desired amounts and ratios of the one or more compounds that is not possible using prior methods. Specific conditions will depend on the viral particle-decoration protein used, the nature of the modification to the engineered decoration protein, and all other relevant factors. It is well within the level of those of skill in the art to determine appropriate incubation conditions, based on the teachings herein. Exemplary conditions are provided in the examples that follow. In one exemplary and non-limiting embodiment in which lambda phage viral particles are used with engineered gpD decoration proteins, the contacting is carried out at about room temperature to 37° C.

In all of these embodiments, the one or more compounds linked to the decoration proteins may comprise two or more different compounds. In this further embodiment the two or more different compounds can be present on the decoration competent particle shell in a defined ratio relative to each other. For example, the decoration proteins may comprise two sets of decoration proteins, a first set linked to compound 1 and a second set linked to compound 2. Since the methods of the invention are carried out in vitro, the decorating can comprise contacting the expanded viral particles with a ratio of the first and second sets of decoration proteins that affords the desired stoichiometric ratio of the two different compounds on the theragnostic particle.

In one non-limiting embodiment, the decoration proteins are bacteriophage lambda gpD proteins, or functional mutants thereof. The lambda gpD decoration protein is a monomer in solution but adds to expanded viral particles as a trimer spike to each of the 140 icosahedral three-fold axes (formed by the structural proteins) on the expanded viral particle surface. The N-terminus of each gpD protein interacts with the capsid shell to provide stabilizing contacts required for shell integrity, while the C-termini exit the gpD trimer spike proximate to the shell surface. Thus, prior art methods that are limited to linking compounds in vivo to the N- or C-termini of gpD may hinder gpD trimer assembly and interfere with its ability to stabilize the capsid. Further, prior work has been limited to N-terminal or C-terminal peptide and protein fusion proteins that are used to decorate infectious phage in vivo. In one embodiment, the engineered gpD proteins comprise a S42C substitution_(SEQ ID NO: 10), which can be the sole decoration protein or can be combined with wild type gpD decoration proteins, or other gpD functional mutants.

The resulting theragnostic particles can be devoid of any packaged material ("empty') within the particle, or may include any desired cargo material packaged on the interior of the particle. For example, DNA is efficiently packaged into the decorated capsids and can be modified to carry specific genes of interest.

In a second aspect, the present invention provides theragnostic particles, comprising a plurality of engineered decoration proteins bound to an outer surface of a decoration competent viral particle shell, wherein the engineered decoration proteins comprise decoration proteins linked to one or more compound not naturally occurring on a wild type viral capsid, and wherein the one or more compounds have at least one feature selected from the group consisting of:

(a) the one or more compounds are non-proteinaceous compounds;

(b) the one or more compounds are present on the theragnostic particle in a defined ratio relative to the engineered decoration protein;

(c) the one or more compounds comprise two or more different compounds, wherein the two or more different compounds are present on the theragnostic particle in a defined ratio relative to each other; and (d) the one or more compounds are linked to the engineered decoration protein at a site on the engineered decoration protein other than the N-terminus or the C-terminus.

All terms used in the first aspect of the invention have the same meaning when referred to in other aspects of the invention. Thus, the decoration competent viral particle shell may be either an expanded viral particle that is stabilized in the expanded state by the decoration proteins, or (b) a viral particle shell that has under extensive conformational change that allows decoration by the decoration protein.

The compositions of the invention overcome the shortcomings of viral particle systems in the art. The theragnostic particles of the invention comprise stoichiometric amounts of engineered decoration protein, and the engineered decoration proteins can be linked to any compound or multiple compounds of interest including non-proteinaceuous compounds, which can themselves be added stochiometrically. Further, the engineered decoration proteins can be modified at any suitable position on the protein that does not interfere with binding to the viral particle shell. As such, the theragnostic particles can be used for any suitable therapeutic or diagnostic purpose, as described in more detail herein. The ability to decorate viral particles with engineered decoration proteins provides an attractive approach to develop "designer" nanoparticles of defined composition and multipartite, symmetric presentation.

In one embodiment, the theragnostic particle comprises a lambda phage expanded viral particle shell is used. In this embodiment, the structural proteins may be protease gpC/scaffolding protein gpNu3 (SEQ ID NO: 3) or the scaffolding protein (SEQ ID NO: 36), portal protein gpB (SEQ ID NO: 1) and major capsid protein gpE (SEQ ID NO: 2), or functional mutants thereof.

In one non-limiting embodiment, a lambda phage viral particle is used. In this embodiment, the structural proteins may be portal protein gpB (SEQ ID: 1) and major capsid protein gpE (SEQ ID: 2), and the minor capsid protein gpC (SEQ ID: 3), or the scaffolding protein contained therein (SEQ ID NO: 36), or functional mutants thereof.

In another embodiment, a bacteriophage T4 viral particle is used; in this embodiment, the structural proteins are the T4 structural proteins, or functional mutants thereof. In a further embodiment, a bacteriophage L viral particle is used; in this embodiment, the structural proteins are the bacteriophage L structural proteins, or functional mutants thereof. In another embodiment, a bacteriophage 21 viral particle is used; in this embodiment, the structural proteins are the bacteriophage 21 structural proteins, or functional mutants thereof. In another embodiment, a bacteriophage 22 viral particle is used; in this embodiment, the structural proteins are the bacteriophage 22 structural proteins functional mutants thereof. In a further embodiment, a bacteriophage P4 viral particle is used; in this embodiment, the structural proteins are the bacteriophage P4 structural proteins, or functional mutants thereof. The structural proteins and their amino acid sequences for each of these viral structural proteins are known to those of skill in the art.

Non-limiting examples of decoration proteins include, but are not limited to, the lambda gpD decoration protein (SEQ ID NO:4), T4 head outer capsid (Hoc) protein (SEQ ID NO:5). T4 small outer capsid (Soc) protein (SEQ ID NO:6), Shp protein of phage 21 (SEQ ID NO:7), the Dec protein of phage L (SEQ ID NO:8), and the Psu protein of phage P4 (SEQ ID NO:9).

The plurality of decoration proteins present on the particle will depend on the viral particle used, the modifications made to the decoration protein, and the intended use of the viral particles, but include enough decoration proteins to bind to at least 80% of the binding sites for the decoration protein that are present on the expanded viral particle shell (e.g.: on the structural proteins defining the shells). In various further embodiments, the engineered decoration proteins bind to at least 85%, 90%, 92%, 94%, 95%, 96%, 97%, 98%, 99% or to all binding sites for the decoration protein that are present on the expanded viral particle shell.

As will be understood by those of skill in the art, the choice of decoration proteins will depend on the viral particle shell/structural proteins being used. Thus, if the viral particle is lambda phage-based, lambda phage structural proteins (or functional mutants thereof) and the engineered lambda decoration protein (engineered gpD protein) will be used. Similarly, if the viral particle is bacteriophage T4 then T4 structural proteins (or functional mutants thereof) and the engineered T4 decoration protein (engineered Hoc or Soc protein) will be used. If the viral particle is bacteriophage 21, then bacteriophage 21 structural proteins (or functional mutants thereof) and the engineered bacteriophage 21 decoration protein (shp protein) will be used. If the viral particle is bacteriophage P22, then bacteriophage 22 structural proteins (or functional mutants thereof) and the engineered bacteriophage L decoration protein (dec protein) will be used. If the viral particle is bacteriophage P4, then bacteriophage P4 structural proteins (or functional mutants thereof) and the engineered bacteriophage P4 decoration protein (psu protein) will be used.

The decoration proteins for use in the methods of the invention are "engineered" in that they are not the wild type proteins, but have been linked to one or more compound not naturally occurring on a wild type viral capsid to provide added functionality. The modifications comprise one or more of (a) the one or more compounds being non-proteinaceous compounds;

(b) the one or more compounds are present on the theragnostic particle in a defined ratio relative to the engineered decoration protein;

(c) the one or more compounds comprise two or more different compounds, wherein the two or more different compounds are present on the theragnostic particle in a defined ratio relative to each other; and (d) the one or more compounds are linked to the engineered decoration protein at a site on the engineered decoration protein other than the N-terminus or the C-terminus The decoration proteins can be modified in any desirable way as disclosed herein, providing a unprecedented increase in the functionality that can be displayed on the surface of the resulting particles compared to prior art methods. In one embodiment, the decoration proteins have an altered amino acid sequence from wild type, such as an insertion, deletion, one or more substitutions, etc. Any suitable modifications can be made to the decoration proteins so long as the resulting engineered decoration protein can bind to the viral particle shell and stabilize it. In one non-limiting embodiment, any solvent accessible residue on a shell bound decoration protein can be modified as desired, such as to facilitate linkage to one or more compounds of interest.

The engineered decoration proteins comprise engineered decoration proteins linked to one or more compound of interest. In one embodiment, the one or more compounds are selected from the group consisting of nucleic acids, lipids, carbohydrates, polypeptides, polymers, organic molecules, inorganic molecules, or combinations thereof. In a further embodiment, the engineered decoration proteins comprise engineered decoration proteins linked to one or more non-proteinaceous compound, such as nucleic acids, lipids, carbohydrates, polymers, organic molecules, inorganic molecules (e.g. magnetic beads and quantum dots, among others), or combinations thereof. In all of these embodiments, the linkage can be at any suitable position on the decoration protein, which is not possible using previously known methods (which are limited to engineered fusion proteins, such that linkage is at the N- of C-terminus of the decoration protein). In various embodiments, the linkage can be at the N- or C-terminus of the decoration protein, or at any suitable internal residue of the decoration protein (e.g., other than the N-terminal or C-terminal residue of the decoration protein). The one or more compounds can be linked to the decoration proteins using any suitable linkage;

determining an appropriate linkage based on the specifics of the one or more compounds and the decoration protein are well within the level of skill in the art based on the teachings herein. As will be understood by those of skill in the art, any suitable combination of decoration proteins can be used, as appropriate for a given expanded viral particle.

In further embodiments, the one or more compounds may be any suitable compound for the theragnostic particles of the invention, including but not limited to therapeutic compounds, diagnostic compounds, adjuvants, antigens, antibodies, etc.

The one or more compounds linked to the decoration proteins may comprise two or more different compounds. In this embodiment the two or more different compounds can be present on the viral particle shell in a defined ratio relative to each other. For example, the decoration proteins may comprise two sets of decoration proteins, a first set linked to compound 1 and a second set linked to compound 2. Since the methods of the invention are carried out in vitro, the decorating can comprise contacting the decoration competent viral particles with a ratio of the first and second sets of decoration proteins that reflects the desired stoichiometric ratio of the two different compounds on the theragnostic particle.

In one non-limiting embodiment, the engineered decoration proteins comprise bacteriophage lambda gpD proteins, or functional mutants thereof. The lambda gpD decoration protein is a monomer in solution but adds to the expanded viral particle as a trimer spike to each of the 140 icosahedral three-fold axes (formed by the structural proteins) on the expanded viral particle surface. In one embodiment, the engineered gpD proteins comprise a S42C substitution (SEQ ID NO: 10), which can be the sole decoration protein on the particle, or can be combined with wild type gpD decoration proteins, or other gpD functional mutants, each comprising the one or more linked compounds (which may be the same or different between the same or different gpD forms). For example, residues in the shell-bound gpD trimer spike that are exposed to solvent include, but are not limited to Thr1, Ser2, Lys3, Glu4, Thr5, Phe6, Thr7, His8, Tyr9, Gln10, Pro11, Gln12, Gly13, Asn14, Ser15; Gly25. Gly26, Leu27, Ser28, Ala29, Lys30, Ala31; Asp40. Thr41, Ser42, Ser43Arg44, Lys45; Asp49, Gly50, Thr51, Thr52, Asp53; Asp66, Gln67, Thr68, Ser69, Thr70, Thr71; Arg81, Tyr82. Glu83, Asp84; Glu89, Ala90, Ala91, Ser92, Asp93, Glu94. Thr95, Lys96, Lys97, Arg98, Thr99, and the N- and C-terminal residues of the protein. In one non-limiting embodiment, one or more residue may be substituted with a Cys residue (including but not limited to an S42C substitution), to facilitate binding of other compounds to the decoration proteins. In another non-limiting embodiment, a non-natural amino acid, including but not limited to azidohomoalanine (Aha) can be incorporated using genetic manipulation of the gene to allow alternate means for chemical modification of the decoration protein, including "click" chemistry.

The resulting theragnostic particles can be devoid of any packaged material ("empty') within the particle, or may include any desired cargo material packaged on the interior of the particle. For example, DNA is efficiently packaged into the decorated capsids and can modified to carry specific genes of interest.

The theragnostic particles of the present invention can be used for any suitable purpose. In one embodiment, the engineered decoration proteins are linked to one or more therapeutic moieties (including but not limited to small molecule drugs, therapeutic antibodies, glycoproteins, carbohydrate polymers, therapeutic nucleic acids (siRNA, antisense RNA, shRNA, gene therapy constructs, etc.), antigens (for use in vaccines), adjuvants (to stimulate an immune response), etc., and the particles can be administered as a therapeutic to a subject in need of treatment. In another embodiment, synthetic polymers including PEG can be used to provide "stealth" characteristics for immune evasion or pH sensitive polymers for escape from cellular endosome compartments.

In various embodiments, the therapeutic is selected from the group consisting of alkylating agents, angiogenesis inhibitors, antibodies, antimetabolites, antimitotics, antiproliferatives, aurora kinase inhibitors, apoptosis promoters (for example, Bcl-xL, Bcl-w and Bfl-1) inhibitors, activators of death receptor pathway. Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, growth factor inhibitors, heat shock protein (HSP)-90 inhibitors, demethylating agents, histone deacetylase (HDAC) inhibitors, hormonal therapies, immunologicals, inhibitors of apoptosis proteins (IAPs) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors and the like.

In another embodiment, the engineered decoration protein comprises one or more diagnostic, localization, and/or imaging moieties (including but not limited to fluorophores, radioactive tracers, dyes, diagnostic antibodies or other ligands, ligands for surface proteins on cells being targeted, etc.), and can be administered to a subject for diagnostic or imaging purposes. For example, the one or more compound may comprise a diagnostic or imaging agent. Many such imaging agents are known to those of skill in the art. Examples of imaging agents suitable for use in the disclosed particles are radioactive isotopes, fluorescent molecules (including fluorescent proteins such as green fluorescent protein, red fluorescent protein, blue fluorescent protein, etc.), magnetic particles (including nanoparticles), metal particles (including nanoparticles), phosphorescent molecules, enzymes, antibodies, ligands, and combinations thereof, while diagnostic agents may comprise a compound that is a diagnostic marker for a particular disorder bound to such an imaging agent. Methods for detecting and measuring signals generated by imaging agents are also known to those of skill in the art. For example, radioactive isotopes can be detected by scintillation counting or direct visualization; fluorescent molecules can be detected with fluorescent spectrophotometers, phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody.

In a further embodiment, the imaging agents can comprise a fluorescent imaging agent, while diagnostic agents may comprise a compound that is a diagnostic marker for a particular disorder bound to the fluorescent imaging agent. A fluorescent imaging agent is any chemical moiety that has a detectable fluorescence signal. This imaging agent can be used alone or in combination with other imaging agents.

Examples of suitable fluorescent agents that can be used in the compositions and methods disclosed herein include, but are not limited to, quantum dots, fluorescein (FITC), 5-carboxyfluorescein-N-hydroxysuccinimide ester, 5,6-carboxymethyl fluorescein, nitrobenz-2-oxa-1,3-diazol-4-yl (NBD), fluorescamine, OPA, NDA, indocyanine green dye, the cyanine dyes (e.g., Cy3, Cy3.5, Cy5, Cy5.5 and Cy7), 4-acetamido-4'-isothiocyanatostilbene-2,2'disulfonic acid, acridine, acridine isothiocyanate, 5-(2'-aminoethyl)aminonaphthalene-1-sulfonic acid (EDANS), 4-amino-N-[3-vinylsulfonyl)phenylinaphthalimide-3,5 disulfonate, N-(4-anilino-1-naphthyl) maleimide, anthranilamide, BODIPY, Brilliant Yellow, coumarin, 7-amino-4-methylcoumarin (AMC, Coumarin 120), 7-amino-4-trifluoromethylcoumarin (Coumaran 151), cyanosine, 4',6-diaminidino-2-phenylindole (DAPI). 5',5''-dibromopyrogallol-sulfonaphthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbenc-2,2'-disulfonic acid, 5-[dimethylamino]naphthalene-1-sulfonyl chloride (DNS, dansylchloride), 4-(4'-dimethylaminophenylazo)benzoic acid (DABCYL), 4-dimethylaminophenylazophenyl-4'-isothiocyanate (DABITC), eosin, eosin isothiocyanate, erythrosin B, erythrosine, isothiocyanate, ethidium bromide, ethidium, 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein isothiocyanate, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron[R] Brilliant Red 3B-A), 6-carboxy-X-rhodamine (ROX), 6-carboxyrhodamine (R6G), lissamine rhodamine B sulfonyl chloride rhodamine (Rhod), 5,6-tetramethyl rhodamine, rhodamine B, rhodamine 123, rhodamine X isothiocyanate, sulforhodamine B, sulforhodamine 101, sulfonyl chloride derivative of sulforhodamine 101 (Texas Red). N,N,N',N'-tetramethyl-6-carboxyrhodamine (TAMRA), tetramethyl rhodamine, tetramethyl rhodamine isothiocyanate (TRITC), riboflavin, rosolic acid, coumarin-6, and the like, including combinations thereof. These fluorescent imaging moieties can be obtained from a variety of commercial sources, including Molecular Probes, Eugene, Oreg. and Research Organics, Cleveland, Ohio, or can be synthesized by those of ordinary skill in the art.

In another example, the imaging agents can comprise a Magnetic Resonance Imaging (MRI) agent, while diagnostic agents may comprise a compound that is a diagnostic marker for a particular disorder bound to the MRI agent. A MRI agent is any chemical moiety that has a detectable magnetic resonance signal or that can influence (e.g., increase or shift) the magnetic resonance signal of another agent. This type of imaging agent can be used alone or in combination with other imaging agent. By combining an MRI imaging agent and, for example, a fluorescent imaging agent, the resulting agent can be detected, imaged, and followed in real-time via MRI. Other imaging agents include PET agents that can be prepared by incorporating an 18F or a chelator for 64Cu or 68Ga. Also, addition of a radionuclide can be used to facilitate SPECT imaging or delivery of a radiation dose, while diagnostic agents may comprise a compound that is a diagnostic marker for a particular disorder bound to the PET agent.

In some embodiments, the diagnostic agent is a diagnostic imaging agent, including but not limited to position emission tomography (PET) agents, computerized tomography (CT) agents, magnetic resonance imaging (MRI) agents, nuclear magnetic imaging agents (NMI), fluoroscopy agents and ultrasound contrast agents. Such diagnostic agents include radioisotopes of such elements as iodine (I), including $^{123}$I, $^{125}$I, $^{131}$I etc., barium (Ba), gadolinium (Gd), technetium (Tc), including $^{99}$Tc, phosphorus (P), including $^{31}$P, iron (Fe), manganese (Mn), thallium (TI), chromium (Cr), including $^{51}$Cr, carbon (C), including $^{14}$C, or the like, fluorescently labeled compounds, or their complexes, chelates, adducts and conjugates. Any suitable PET agents can be used, including but not limited to carbon-11, nitrogen-13, oxygen-15, fluorine-18,11C-metomidate, and glucose analogues thereof, including but not limited to fludeoxyglucose (a glucose analog labeled with fluorine-18.

The particles can also be used in viral research, such as to identify protein components required for viral assembly and mechanistic interrogation of the assembly process.

In a further embodiment, the invention provides pharmaceutical compositions, comprising the theragnostic particles of any embodiment or combination of embodiments of the invention and a pharmaceutically acceptable carrier. The pharmaceutically acceptable carrier is non-toxic, biocompatible and is selected so as not to detrimentally affect the biological activity of the multimers (and any other therapeutic agents combined therewith). Exemplary pharmaceutically acceptable carriers for peptides are described in U.S. Pat. No. 5,211,657 to Yamada. The compositions may be formulated into preparations in solid, semi-solid, gel, liquid or gaseous forms such as tablets, capsules, powders, granules, ointments, solutions, suppositories, inhalants, and injections, allowing for oral, parenteral, or surgical administration. Suitable carriers for parenteral delivery via injectable, infusion, or irrigation and topical delivery include distilled water, physiological phosphate-buffered saline, normal or lactated Ringer's solutions, dextrose solution. Hank's solution, or propanediol. In addition, sterile, fixed oils may be employed as a solvent or suspending medium. For this purpose any biocompatible oil may be employed including synthetic mono- or diglyceridcs. In addition, fatty acids, such as oleic acid, find use in the preparation of injectables. The carrier and agent may be compounded as a liquid, suspension, polymerizable or non-polymerizable gel, paste or salve. The carrier may also comprise a delivery vehicle to sustain (i.e., extend, delay, or regulate) the delivery of the agent(s) or to enhance the delivery, uptake, stability, or pharmacokinetics of the therapeutic agent(s). Such a delivery vehicle may include, by way of non-limiting example, microparticles, microspheres, nanospheres, or nanoparticles composed of proteins, liposomes, carbohydrates, synthetic organic compounds, inorganic compounds, polymeric or copolymeric hydrogels, and polymeric micelles. Suitable hydrogel and micelle delivery systems include the PEO:PHB:PEO copolymers and copolymer/cyclodextrin complexes disclosed in International Publication No. WO 2004/009664 A2, and the PEO and PEO/cyclodextrin complexes disclosed in U.S. Publication No. 2002/0019369 A1. Such hydrogels may be injected locally at the site of intended action, or subcutaneously or intramuscularly to form a sustained release depot.

For intrathecal (IT) or intracerebroventricular (ICV) delivery, appropriately sterile delivery systems (e.g., liquids; gels, suspensions, etc.) can be used to administer the compositions. For oral administration of non-peptidergic agents, the compositions may be carried in an inert filler or diluent such as sucrose, cornstarch, or cellulose.

The compositions of the present invention may also include biocompatible excipients, such as dispersing or wetting agents, suspending agents, diluents, buffers, penetration enhancers, emulsifiers, binders, thickeners, flavoring agents (for oral administration). Exemplary formulations can be parenterally administered as injectable dosages of a solution or suspension of the multimer in a physiologically acceptable diluent with a pharmaceutical carrier that can be a sterile liquid such as water, oils, saline, glycerol, or ethanol. Additionally, auxiliary substances such as wetting or emulsifying agents, surfactants, pH buffering substances and the like can be present in compositions comprising modified polypeptides. Additional components of pharmaceutical compositions include petroleum (such as of animal, vegetable, or synthetic origin), for example, soybean oil and mineral oil. In general, glycols such as propylene glycol or polyethylene glycol are preferred liquid carriers for injectable solutions.

The pharmaceutical composition can also be administered in the form of a depot injection or implant preparation that can be formulated in such a manner as to permit a sustained or pulsatile release of the multimers and other therapeutic (if present).

The pharmaceutical composition may further comprise (a) a lyoprotectant; (b) a surfactant; (c) a bulking agent; (d) a tonicity adjusting agent; (e) a stabilizer, (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant. e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol. chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride. The pharmaceutical composition can be packaged in any suitable manner.

Figure 8:
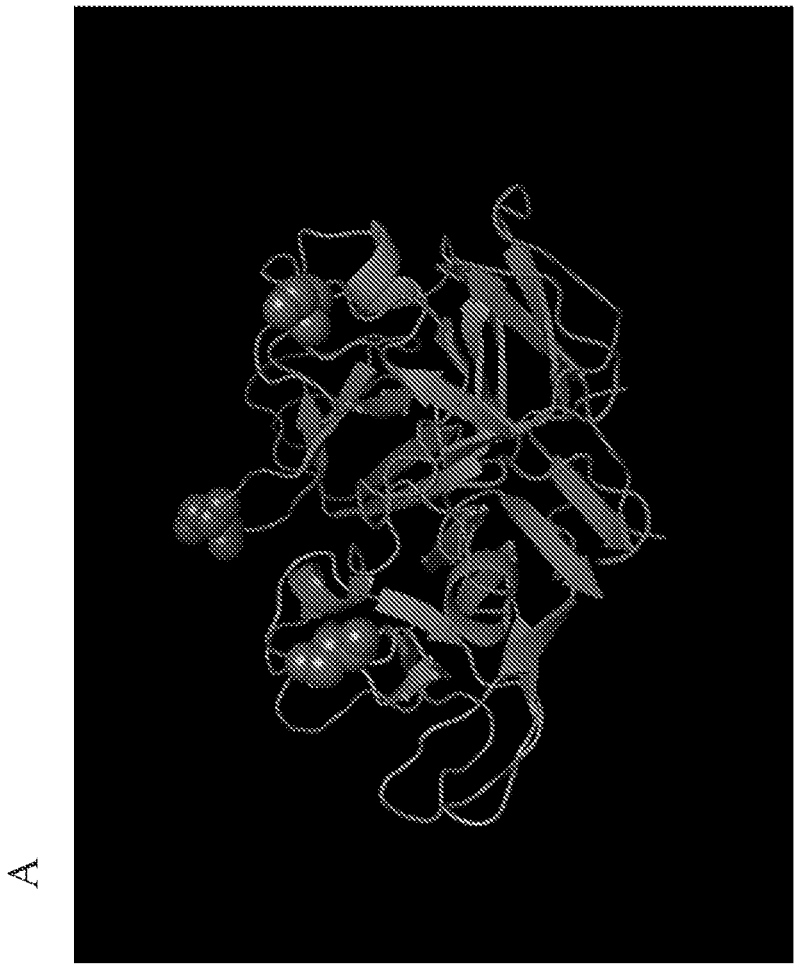
FIG. 8. The gpD Trimer Spike and gpD Constructs Used in this Study. Panel A. Side view of the gpD-WT trimer. The gpD trimer is shown in cartoon representation with each subunit colored a different shade of blue and with serine 42 depicted as red spheres. Panel B. The gpD constructs used in this study.
Figure 8:
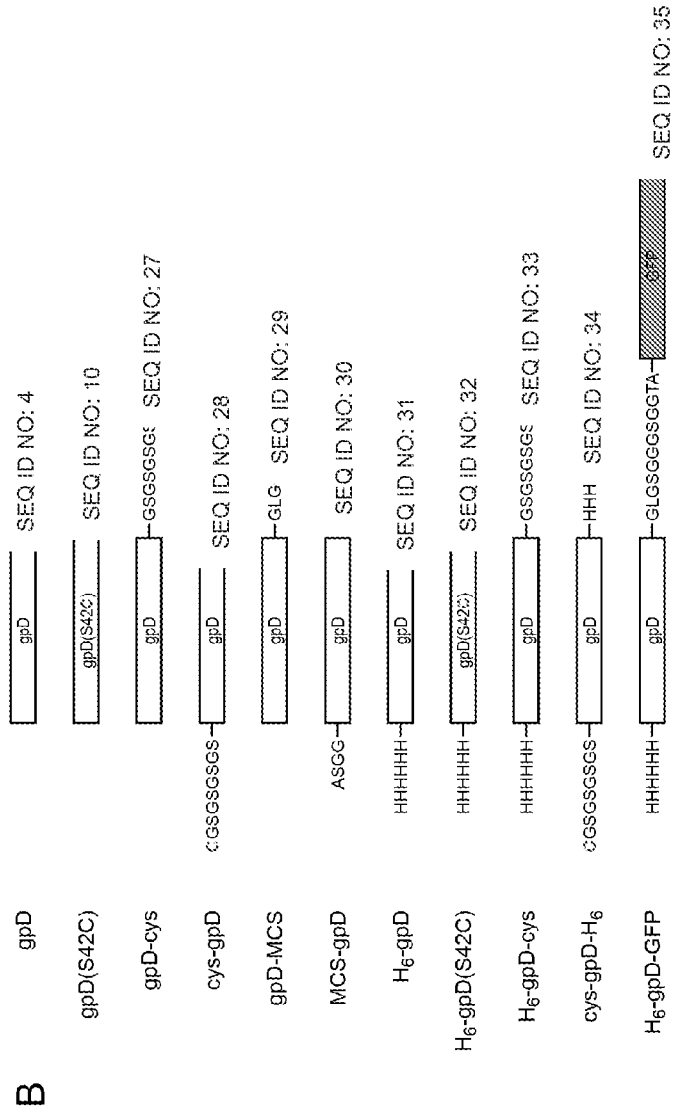

In a third aspect, the present invention provides isolated recombinant protein comprising or consisting of the amino acid sequence of gpD(S42C) (SEQ ID NO: 10). As demonstrated in the examples that follow, gpD(S42C) is a particularly useful decoration protein. The crystal structure of the gpD trimer spike reveals that Ser42 is positioned at the apex of the spike in all three subunits (FIG. 8A). Modification of this residue thus places any linked compound projecting away from the capsid surface and into solution for optimal display, and with minimal insult to gpD spike assembly and shell integrity. There are no other cysteine residues in the native protein, and thus the functional gpD mutant provides a unique site for chemical linkage via any suitable means, such as using maleimide-based tags. The use of these and other linking chemistries to link two compounds to each other is well known in the art, and examples are provided below.

In another embodiment, the invention provides isolated recombinant protein comprising or consisting of the amino acid sequence of gpD as modified by an amino acid substitution at one or more residues selected from the group consisting of Thr1, Ser2, Lys3, Glu4, Thr5, Phe6, Thr7, His8, Tyr9, Gln10, Pro11, Gln12, Gly13, Asn14, Ser15; Gly25, Gly26, Leu27, Ser28, Ala29, Lys30, Ala31; Asp40. Thr41, Ser42. Ser43Arg44, Lys45; Asp49, Gly50, Thr51, Thr52, Asp53; Asp66, Gln67, Thr68, Ser69, Thr70, Thr71; Arg81, Tyr82, Glu83, Asp84; Glu89, Ala90, Ala91, Ser92, Asp93. Glu94, Thr95. Lys96, Lys97, Arg98, and Thr99. In one embodiment, the one or more wild type amino acids are substituted with a Cys residue and/or an azidohomoalanine (Aha) residue.

In a further embodiment, a composition is provided comprising (a) isolated recombinant protein comprising or consisting of the amino acid sequence of SEQ ID NO: 10 (gpD(S42C)); and (b) one or more compounds linked to the recombinant protein via the cysteine at position 42. The compositions according to this embodiment are particularly useful for constructing theragnostic particles according to the present invention. The compound may be any suitable compound, including but not limited to compounds selected from the group consisting of nucleic acids, lipids, carbohydrates, polypeptides, polymers, organic molecules, or inorganic molecules, or combinations thereof. In a further embodiment, the compound is a non-proteinaceous compound, such as nucleic acids, lipids, carbohydrates, polymers, organic molecules, inorganic molecules (e.g. magnetic beads and quantum dots, among others), or combinations thereof. In a further embodiment, the composition comprises a plurality of such recombinant proteins with linked compounds, wherein the linked compounds may be the same or different from one recombinant protein to the next in the plurality.

In a further aspect, the invention provides isolated nucleic acids encoding the recombinant gpD(S42C) protein of the invention. The nucleic acids may comprise RNA or DNA, and can be prepared and isolated using standard molecular biological techniques, based on the teachings herein. The nucleic acids may comprise additional domains useful for promoting expression and/or purification of the encoded protein, including but not limited to polyA sequences, modified Kozak sequences, and sequences encoding epitope tags, export signals, and secretory signals, nuclear localization signals, and plasma membrane localization signals.

In a further aspect, the present invention provides recombinant expression vectors comprising the nucleic acid encoding the recombinant gpD(S42C) protein operatively linked to a promoter. "Recombinant expression vector" includes vectors that operatively link a nucleic acid coding region or gene to any promoter capable of effecting expression of the gene product. The promoter sequence used to drive expression of the disclosed nucleic acids in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; Gene Transfer and Expression Protocols, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA, and may comprise any other components as deemed appropriate for a given use, including but not limited to selection markers such as an antibiotic-resistance gene.

In a still further aspect, the present invention provides host cells comprising the recombinant expression vectors disclosed herein, and progeny thereof, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2$^{nd}$ Ed. (R. I. Freshney. 1987. Liss, Inc. New York, N.Y.). Techniques utilizing cultured cells transfected with expression vectors to produce quantities of polypeptides are well known in the art.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure. Accordingly, the disclosure is not limited.

EXAMPLE 1

The assembly of "complex" DNA viruses such as the herpesviruses and many tailed bacteriophages includes a DNA packaging step where the viral genome is inserted into a pre-formed procapsid shell. Packaging triggers a remarkable capsid expansion transition that results in thinning of the shell and an increase in capsid volume to accept the full-length genome. This transition is considered irreversible; however, here we demonstrate that the phage λ procapsid can be expanded with urea in vitro and that the transition is fully reversible. This provides an unprecedented opportunity to evaluate the thermodynamic features of this fascinating and essential step in virus assembly. We show that urea-triggered expansion is highly cooperative and strongly temperature dependent. Thermodynamic analysis indicates that the free energy of expansion is influenced by magnesium concentration (3-13 kcal/mol in the presence of 0.2-10 mM $Mg^{2+}$) and that significant hydrophobic surface area is exposed in the expanded shell. Conversely, $Mg^{2+}$ drives the expanded shell back to the procapsid conformation in a highly cooperative transition that is also temperature dependent and strongly influenced by urea. We demonstrate that the gpD decoration protein adds to the urea-expanded capsid, presumably at hydrophobic patches exposed at the three-fold axes of the expanded capsid lattice. The decorated capsid is biologically active and sponsors packaging of the viral genome in vitro. The roles of divalent metal and hydrophobic interactions in controlling packaging-triggered expansion of the procapsid shell are discussed in relation to a general mechanism for DNA-triggered procapsid expansion in the complex dsDNA viruses.

Introduction

The pathways for the assembly of an infectious virus from macromolecular precursors are remarkably similar in all of the complex double stranded DNA (dsDNA) viruses both eukaryotic and prokaryotic[1; 2]. In particular, the DNA replication, procapsid assembly, and genome packaging pathways are strongly conserved in the herpesvirus groups and in many bacteriophages[3; 4; 5; 6; 7]. In these cases, a terminase enzyme specifically recognizes viral DNA and the terminase motor translocates the duplex into the interior of a pre-formed procapsid[3; 4; 5; 6]. DNA packaging triggers a major reorganization of the proteins assembled into the procapsid shell, which typically results in expansion of the shell into a thinner, more angularized icocahedral structure[8; 9; 10]. Bacteriophage lambda (λ) has been extensively characterized genetically, biochemically, and structurally and provides an ideal system in which to define the molecular details of genome packaging[7; 11; 12].

Assembly of the λ procapsid follows an ordered pathway that is generally conserved from phage to the herpesviruses. Briefly, assembly initiates with self-association of the portal protein (gpB) into a dodecameric ring structure[12; 13; 14; 15]. This nucleates polymerization of the major capsid protein (gpE) into an icosahedral shell, chaperoned by co-polymerization with the scaffolding protein (gpNu3)[16; 17; 18; 19]. A limited number of viral protease proteins (gpC) are also incorporated into the nascent procapsid interior, which auto digests, degrades the scaffold protein, and removes 20 residues from the N-terminus of roughly half of the portal proteins[13; 14]. The proteolysis products exit the structure to afford the mature procapsid composed of a portal ring situated at a unique vertex of the icosahedral shell; this portal vertex provides a hole through which viral DNA can enter during packaging and exit during infection.

Genome packaging represents the intersection of the DNA replication and procapsid assembly pathways[3; 7]. The terminase enzyme specifically recognizes viral DNA and then binds to the portal vertex of an empty procapsid (FIG. 1). This activates the terminase motor, which translocates DNA into the procapsid interior, fueled by ATP hydrolysis. Upon packaging ~15 kb DNA the procapsid undergoes an expansion process, which involves a significant reorganization of the capsid proteins assembled into the shell (FIG. 1; discussed further below)[7; 11; 20; 21; 22; 23]. Conventional wisdom dictates that procapsid expansion represents "a major irreversible change in the assembled capsid proteins of the procapsid shell"[22; 24; 25].

In a number of viral systems, this irreversible transition can be artificially triggered in vitro using temperature, pH, or denaturants[26; 27; 28; 29; 30; 31]. In this study we examine urea-triggered expansion of the λ procapsid and report the surprising observation that the transition is fully reversible. The equilibrium is strongly affected by urea concentration, magnesium concentration, salt, and temperature. We present physical, biochemical, and structural studies that characterize this transition and confirm that the urea-expanded structures faithfully recapitulate those generated by DNA packaging in vivo. The relevance of these studies with respect to a general mechanism for DNA-triggered procapsid expansion in the complex dsDNA viruses is discussed.

Results

Figure 2:
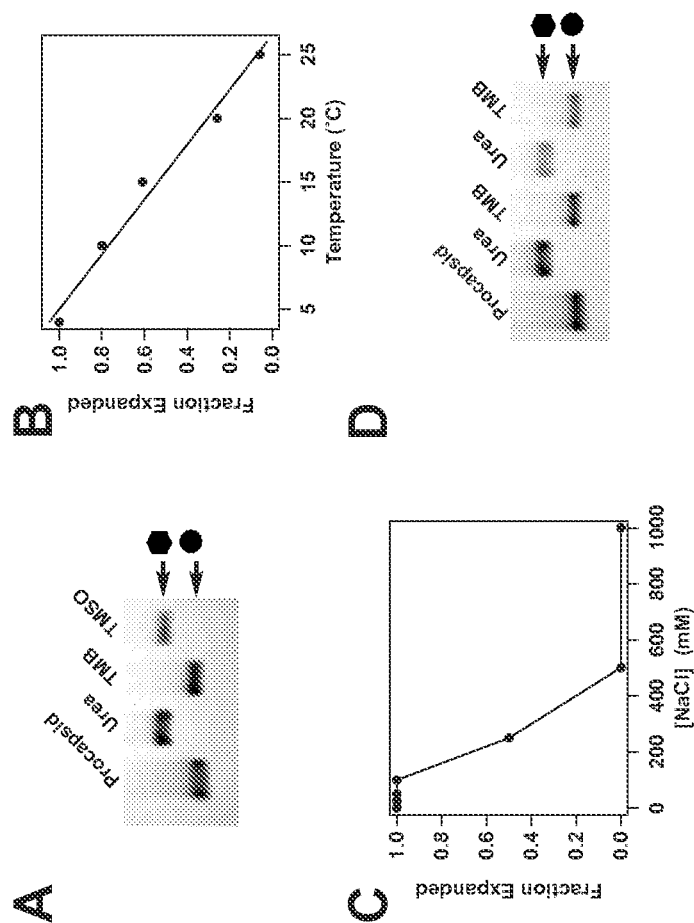
FIG. 2. Expansion of the Lambda Procapsid in Vitro. Panel A. Magnesium and Urea Stabilize the Procapsid and Expanded Capsid Shells, Respectively. Procapsids were expanded in 2.5 molar urea, which affords the expanded capsid shell (Urea). The expanded shells were then buffer exchanged into either high magnesium (15 mM, TMB) or low magnesium (1 mM, TMSO) buffer, as indicated. The migration of the procapsid (●) and expanded capsid (●) in the agarose gel is indicated at right of the gel. Panel B. Urea-Triggered Expansion is Strongly Temperature Dependent. Procapsids were incubated in 2.5 molar urea for 15 minutes at the indicated temperature and then analyzed by 0.8% agarose gel. Panel C. Urea-Triggered Expansion is Inhibited by Salt. Procapsids were expanded as described in Materials and Methods except that NaCl was added to the reaction mixture as indicated. Panel D. Procapsid Expansion is Fully Reversible. Procapsids were expanded in 2.5 molar urea for 15 minutes at 4° C. (Urea) and then buffer-exchanged into TMB buffer. The identical sample was again expanded and buffer exchanged as indicated.

Urea Triggers Expansion of the Lambda Procapsid. Expansion of the λ procapsid in vivo is triggered upon packaging of ~15 kb duplex DNA (FIG. 1)[20; 21; 23]. We examined a variety of approaches to artificially expand procapsids to study this transition in vitro. In contrast to other viral systems, neither pH in the range of 3-9 nor heat in the range of 4° C. to 50° C. are effective in promoting expansion. Prior work has demonstrated that the λ procapsid can be artificially expanded by incubation with four molar urea for 30 minutes on ice[28]. Here we recapitulate this result and demonstrate that incubation of our purified procapsids in 2.5 molar urea on ice for 15 minutes triggers procapsid expansion (FIG. 2A). Due to the time required for analysis by agarose gel, an accurate quantitation of the reaction rate is not possible using this assay. We note, however, that procapsid expansion is relatively rapid and essentially complete in ~1 minute by gel assay (data not shown). Interestingly, urea-triggered procapsid expansion is strongly temperature dependent. While procapsids expand rapidly and completely on ice, the transition is strongly inhibited by elevated temperature (FIG. 2B). We considered that this might reflect a kinetic effect; however, urea-triggered expansion was not observed even after 24 hours at 25° C. Urea-triggered expansion is also inhibited by NaCl in a concentration dependent manner (FIG. 2C). Salt inhibition is likely responsible for the observation that the λ procapsid does not expand in the presence of 4 molar guanidinium hydrochloride. For the remainder of this work we will use the term "procapsid" to describe the contracted shell (●) and the term "capsid" to describe the expanded, angularized structure (✹; see FIG. 2A).

Expansion of the Lambda Procapsid is Reversible. Previous studies reported that dialysis of urea from the reaction mixture affords a preparation of λ capsids that remain in the expanded state[28]. In contrast, we observe that the structures contract back to the procapsid state when urea is removed by buffer exchange into TMB buffer (FIG. 2A). Close inspection of the published data reveals that the primary difference between our studies and previous work is the buffer used to remove urea from the sample. This was investigated and we show that the capsids remain in the expanded state when exchanged into the TMSO buffer used in the prior studies (10 mM Tris buffer, pH 8, containing 1 mM MgSO₄ and 10 mM NaN₃). In contrast, the expanded shells contract back to the procapsid conformation when exchanged into our standard TMB buffer (50 mM Tris buffer, pH 8, containing 15 mM MgCl₂ and 7 mM β-ME) (FIG. 2A). It is generally accepted that procapsid expansion is an irreversible process in virus development and this surprising observation was more fully explored.

Each of the components in the two buffers was individually examined, which reveals that the increased concentration of $Mg^{2+}$ in our TMB buffer is responsible for driving the expanded structure back to the procapsid state; none of the other components has any effect. We next evaluated other metals and the data presented in Table 1 demonstrate that capsid contraction is driven by all of the divalent metals examined. In contrast, none of the monovalent salts have any effect at similar concentrations. Finally, we examined the extent to which the transition is reversible. Procapsids that had been previously expanded with urea and then contracted by buffer exchange into TMB buffer (15 mM $Mg^{2+}$) were again expanded in urea and again buffer exchanged into TMB buffer. The data presented in FIG. 2D demonstrate that the λ procapsid can be repeatedly expanded and contracted in solution by urea and $Mg^{2+}$, respectively.

TABLE 1

Di-Valent Metals Drive Contraction to the Procapsid Conformation. Procapsids were expanded in 2.5M urea on ice for 15 minutes and then exchanged into buffer containing 1 mM MgCl₂ and the indicated salt at 15 mM, unless otherwise indicated. In all cases, the preparations contained either exclusively expanded capsid or contracted procapsid structures, as indicated.

| Salt (15 mM) | Capsid State |
| --- | --- |
| MgCl₂ | Contracted |
| MgSO₄ | Contracted |
| CaCl₂ | Contracted |
| BaCl₂ | Contracted |
| MnCl₂ | Contracted |
| Ni(NO₃)₂ | Contracted |
| ZnCl₂ | Contracted |
| NaCl | Expanded |
| Na phosphate | Expanded |
| KCl | Expanded |
| K glutamate | Expanded |
| 100 mM NaCl | Expanded |
| 500 mM NaCl | Contracted |

Figure 3:
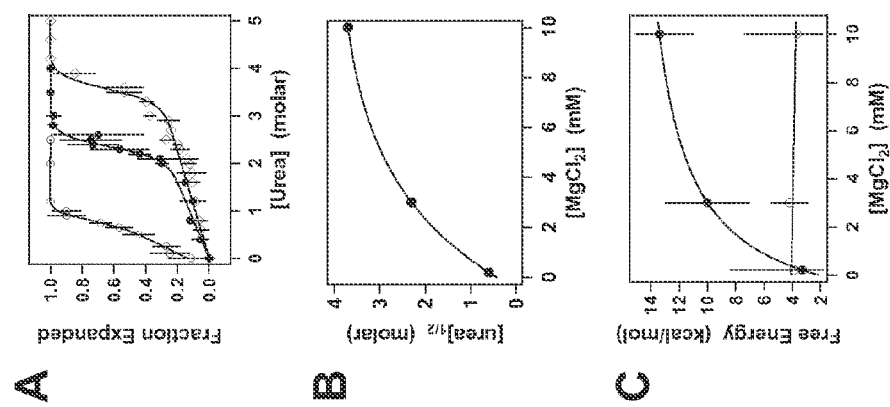
FIG. 3. Thermodynamic Characterization of Urea-Triggered Procapsid Expansion. Panel A. Procapsids in the absence (○) or in the presence of 3 mM (●) or 10 mM (◇) $MgCl_2$ were incubated on ice in the presence of increasing concentrations of urea, as indicated, and the fraction of expanded capsids was quantified by gel assay. Each data point represents the average of at least three separate measurements with standard deviations indicated with bars. The solid line represents the best fit of the data to equation 1. Panel B. The data presented in Panel A was analyzed according to equation 2 to afford the concentration of urea required to expand half of the procapsid shells ($[urea]_{1/2}$). Panel C. The free energy of capsid expansion (●) and the denaturant m values (○) derived from Panel A are plotted as a function of $MgCl_2$.

Thermodynamic Analysis of Urea-Triggered Procapsid Expansion. The data presented above demonstrate that urea-triggered expansion of the λ procapsid is reversible. Moreover, close inspection of the gels fails to reveal any evidence of intermediate states between the contracted procapsid and expanded capsid conformations (see FIG. 2). These observations suggest that the expansion reaction may be modeled as a reversible, two-state transition and we adapted analytical tools developed to characterize two-state protein unfolding reactions[32]. Procapsids were expanded as described in Materials and Methods except that the concentration of MgCl₂ and urea was varied as indicated. In the presence of 0.2 mM MgCl₂, procapsid expansion is urea-concentration dependent and strongly cooperative (FIG. 3A). Analysis of the data according to a reversible, two-state transition (Equation 1)[32] affords a free energy of expansion, $\Delta G(H_2O)$~3 kcal/mol. We note that the expansion transition under these conditions is extremely facile and occurs with essentially no pre-transition baseline. The error associated with this analysis is thus rather large; $\Delta G(H_2O)=3.3\pm4.4$ kcal/mol).

As described above, $Mg^{2+}$ drives the expanded shell back to the contracted procapsid conformation. We interpreted the data to indicate that urea and $Mg^{2+}$ have antagonistic effects on the conformation of the λ capsid and we directly tested this hypothesis. The above urea-expansion study was repeated except that MgCl₂ was included in the reaction mixture at 3 mM or 10 mM. The data clearly indicate that $Mg^{2+}$ antagonizes urea-triggered procapsid expansion in a concentration-dependent manner (FIG. 3A) and that the concentration of urea required to expand half of the procapsids ($[urea]_{1/2}$) is strongly affected by $Mg^{2+}$ (FIG. 3B). Analysis of the expansion data according to Equation 1 affords a ΔG(H₂O) of 10.0±3.0 kcal/mol and 13.4±2.4 kcal/mol in the presence of 3 mM and 10 mM Mg²⁺, respectively (FIG. 3C). For comparison, "typical" protein unfolding reactions report [urea]$_{1/2}$ between 3-6 molar and a ΔG(H₂O) that ranges between 5-15 kcal/mol[32; 33; 34; 35]. Finally, we note that the denaturant "m" value for the transition is relatively large and insensitive to the concentration of Mg²⁺ in the reaction mixture (FIG. 3C). This is discussed further below.

Figure 4:
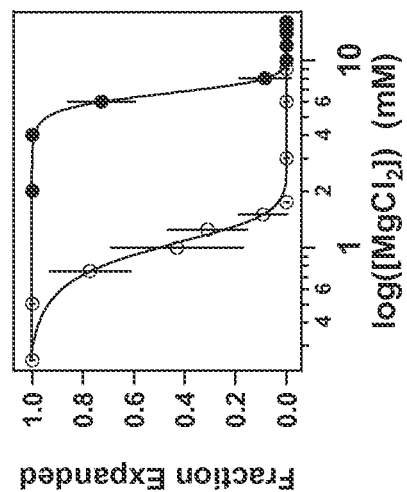
FIG. 4. Magnesium Drives Contraction of the Expanded Capsid to the Procapsid State. $MgCl_2$ at the indicated concentration was added to expanded capsids in the absence (○) or presence (●) of 2.5 molar urea as described in Materials and Methods. The fraction of contracted capsids was quantified by agarose gel assay. Each data point represents the average of at least three separate measurements with standard deviations indicated with bars. The solid lines represent the best fit of the data according to Equation 3.

Mg²⁺ Driven Capsid Contraction. To further explore the antagonist effects of urea and Mg²⁺, a preparation of expanded capsids in buffer lacking both urea and Mg²⁺ was prepared by buffer exchange. The expanded capsids were then incubated in the presence of increasing concentrations of MgCl₂ and the fraction of structures that had contracted back to the procapsid state was quantified by gel assay. The data presented in FIG. 4 demonstrate that Mg²⁺ drives the expanded shell back to the procapsid conformation in a concentration dependent and strongly cooperative manner; analysis of the data according to Equation 3 affords a [Mg²⁺]$_{1/2}$=1.1±0.1 mM. We next repeated the experiment as described above except that 2.5 molar urea was included in the reaction buffer. While Mg²⁺ can still drive the contraction transition, significantly higher concentrations of divalent metal are required; [Mg²⁺]$_{1/2}$=6.5±0.4 mM (FIG. 4).

Biological Activity of the Expanded λ Capsids. We have demonstrated that the λ procapsid can be reversibly expanded and contracted in vitro, which has allowed a rigorous thermodynamic characterization of the transition (vide supra). Evaluation of these data with specific reference to virus assembly requires that urea-triggered expansion mimic the natural pathway that is triggered by DNA packaging in vivo. The three most essential functions required of procapsids during DNA packaging are (i) the ability to bind the terminase motor and sponsor DNA packaging, (ii) the ability to bind the gpD decoration protein to the expanded capsid lattice, and (iii) the capacity of the decorated shell to physically withstand the internal forces generated by the packaged λ genome.

Figure 5:
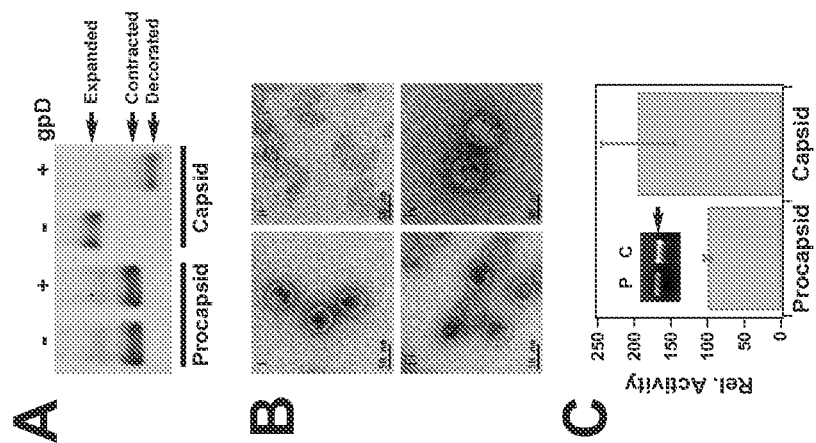
FIG. 5. Urea-Expanded Capsids are Biologically Functional Panel A. Expanded Capsids Bind the gpD Decoration Protein. Procapsids and expanded capsids (in the absence of urea) were incubated with gpD as described in Materials and Methods and the products were analyzed by 0.8% agarose gel. Note that the gpD-decorated shell migrates faster than both the procapsid and the expanded capsid shells. Panel B. The gpD Protein Stabilizes the Expanded Capsid Shell. Micrographs of negatively stained procapsids (i), expanded capsids (ii), expanded capsids that have been re-contracted with 15 mM $MgCl_2$ (iii), and gpD-decorated expanded shells (iv). Note that the expanded shells are fragile and deteriorate during preparation for EM analysis. Expanded capsids that have been re-contracted with magnesium or stabilized with gpD are structurally sound. Panel C. Expanded Capsids are Biologically Active. Procapsids and GpD-decorated expanded procapsids (Capsids) were used in an in vitro DNA packaging assay. The data represent the average of three separate experiments with standard deviations indicated with bars. Inset. DNAase resistant (packaged) viral DNA was analyzed by gel assay. Note that only full-length genomic DNA (48.5 kb, arrow) is rendered DNAase resistant. This indicates that both capsid preparations package DNA in a processive manner.

Our lab has developed an in vitro DNA packaging assay where viral DNA is packaged into purified procapsids in a defined biochemical assay system[36; 37]. These studies have demonstrated that the packaging reaction is magnesium-dependent and that the optimal MgCl₂ concentration is ~5 mM. This presents a problem when trying to package into the expanded capsids since they contract in the presence of >1 mM Mg²⁺ (FIG. 4). Therefore, as a first step towards demonstrating the biological activity of the urea-expanded capsids, we examined gpD binding to the capsid shell. An expanded capsid preparation in 1 mM Mg²⁺ (no urea) was prepared and purified gpD was added to the mixture. FIG. 5A clearly shows that the gpD decoration protein efficiently adds to the expanded capsid lattice. Several features of this interaction are noteworthy. First, while gpD binds to the expanded capsid, no interaction is observed with unexpanded procapsid shell (FIG. 5A); this feature is similarly observed in vivo[7; 38]. Second, the gpD-decorated shell migrates faster in the gel than does the expanded capsid alone. This indicates that gpD addition affords a more negatively charged capsid shell. Third, gpD stabilizes the expanded shell and the decorated capsids no longer contract in the presence of elevated Mg²⁺ concentrations (Medina, Kruse, and Catalano, unpublished;[39]). Finally, electron micrographs demonstrate that the gpD decorated structures show thinning of the capsid shell and increased angularization of the icosahedral structure (FIG. 5B), as observed in vivo[23]. We note that the expanded shells are fragile and easily damaged during preparation for EM analysis (see FIG. 5B). In contrast, the gpD-decorated shells are robust and intact structures are evident in the micrographs.

To further demonstrate biological activity, we examined the genome packaging activity of the gpD-decorated capsids. Terminase-mediated packaging of the λ genome into a capsid renders the duplex resistant to DNase and the packaging products are visualized on an agarose gel[36]. Our standard DNA packaging assay was modified by pre-incubating the expanded capsids with gpD and then adding the other reaction components required for genome packaging. The data presented in FIG. 5C demonstrate that the expanded, gpD coated capsids are fully competent for DNA packaging. Importantly, the only packaging product is the full-length λ genome (inset). This indicates that packaging into the urea-expanded capsids is highly processive and that DNA-filled particles can withstand the tremendous internal forces generated by the tightly packaged, highly pressurized DNA genome[20; 40; 41]. These features mirror the observations with bone fide λ capsids both in vitro[20; 40] and in vivo[7; 14; 38].

Discussion

The packaging of a viral genome into a pre-formed procapsid structure is an essential step in the assembly of complex dsDNA viruses. A universal feature is that DNA packaging triggers maturation of the procapsid, often resulting in expansion and thinning of the shell to afford a larger, more angularized structure. Dogma contends that this step is irreversible so that unidirectional assembly of the viral particle is ensured. This presumption is consistent with a number of in vitro studies where procapsid expansion has been artificially triggered by using pH, heat, or denaturants[26; 27; 28; 30; 42; 43; 44]; however, there has been some indication that strict irreversibility may not necessarily be the case. For instance, pH-induced expansion of the HK97 procapsid proceeds through a number of intermediates and there is evidence that at least one transition may be partially (10%) reversible[45]. That said, the fully expanded capsid structure is stable and does not contract back to the procapsid conformation. Thus, our demonstration that urea-triggered expansion of the λ procapsid is fully reversible and that the expansion-contraction transition can be repeated for multiple cycles is unexpected and quite remarkable.

Energetic Features of Procapsid Expansion. We have demonstrated that Mg²⁺ and urea stabilize the contracted and the expanded conformations of the λ capsid, respectively. We have further shown that inter-conversion between the two structures is highly cooperative and fully reversible. These features allow a rigorous thermodynamic characterization of the expansion reaction, which has not been possible in any other system. Our data indicate that the free energy of urea-triggered procapsid expansion, ΔG(H₂O), is ~13 kcal/mol in the presence of 10 mM MgCl₂. This translates directly to ~90 picoNewtons·nanometer (pN·nm) work done to expand an individual capsid. It is generally presumed that packaging DNA into the procapsid interior generates pressure that ultimately provides the energy, at least in part, required to trigger expansion[6; 7; 8; 20]. Previous single-molecule studies suggest that expansion is triggered when the terminase motor inserts ~15 kb duplex DNA into the procapsid (a magnesium concentration of 10 mM was used in the laser tweezer studies) (see FIG. 1)[20]. The motor generates ~5 pN force at this point[46; 47], which reflects the energy required to condense the DNA into the confines of the procapsid interior. To the first approximation, this force will generate a pressure of 0.06 N/cm² on the inside of the shell. Expansion increases the diameter of the particle from 50 nm to 60 nm[23; 41], which results in a volume increase of $4.5 \times 10^{-20}$ liters. This means that the mechanical work performed by the motor at the point of procapsid expansion is ~70 pN·nm per capsid (work=PΔV), which to the first approximation corresponds quite well to the work required to expand the structure with urea in vitro (~90 pN·nm, above). While admittedly qualitative in nature, these simple calculations indicate that the free energy of procapsid expansion by urea is commensurate with the work performed by the motor at the point of expansion during DNA packaging. This is discussed further below.

Magnesium Stabilization of the Procapsid–Possible Biological Role? Divalent metals play an essential role in the assembly of many viruses. For example, $Ca^{2+}$ plays an important role in the assembly and stabilization of polyoma virus[48; 49; 50] and herpes virus[51] particles. Similarly, early studies demonstrated an important role for $Mg^{2+}$ in the assembly and stability of an infectious λ virus[52; 53]. Chelation of $Mg^{2+}$ with EDTA destroys λ infectivity and it has been proposed that $Mg^{2+}$ serves as a counter-ion to maintain DNA in the condensed state within the nucleocapsid[54]. Stabilization of the procapsid conformation by divalent metals as demonstrated here indicates that there is a metal-capsid interaction in addition to the metal-DNA interaction. Indeed, recent structural studies have identified putative metal-binding sites localized at the 3-fold axes on the interior surface of the HK97 procapsid[55]. We suggest that this feature is recapitulated in λ and that this metal-capsid interaction is responsible, at least in part, for stabilizing the procapsid conformation. This model has some interesting predictions.

In addition to the pressure generated by the packaged DNA (vide supra), it is presumed that duplex interactions with the inner surface of the procapsid shell trigger the expansion transition; however, mechanistic details of these putative interactions remain obscure. We suggest the following. Condensation of DNA within the capsid interior is energetically unfavorable due, in part, to significant charge-repulsion by the closely packed phosphodiester backbone. Charge neutralization by polyamines and divalent metals is required to ensure efficient condensation and packaging of the genome[54; 56; 57]. The terminase motor translocates over 600 base pairs/second into the capsid interior[20; 58] and it is tempting to speculate that the rapidly packaged duplex effectively strips the $Mg^{2+}$ bound at the interior capsid surface. This would serve to decrease the free energy requirement for expansion of the shell, perhaps as much as 10 kcal/mol (FIG. 3), and to promote the transition. As shown here, expansion is accompanied by addition of gpD to the capsid surface, which stabilizes the expanded shell and prevents contraction back to the procapsid state. In this situation, divalent metals are free to bind to and stabilize the condensed DNA. Work currently underway in our lab seeks to directly measure the duplex length requirement for procapsid expansion in the presence of various divalent metals to directly test this hypothesis.

Procapsid Expansion Exposes Hydrophobic Surface Area. We propose that the procapsid conformation is stabilized not only by divalent metal, but also by hydrophobic interactions between the capsid proteins in the contacted shell (see FIG. 6). The expansion transition requires disruption of these interactions and exposure of hydrophobic patches on the expanded capsid surface. This hypothesis is based in part on the observation that urea triggers procapsid expansion; while the mechanism remains controversial, it is generally accepted that urea disrupts hydrophobic interactions and effectively "solvates" hydrophobic residues in water[34; 59; 60].

Thus, in analogy to protein unfolding, urea stabilizes the expanded capsid conformation and shifts the equilibrium towards the expanded state. The model is also consistent with the observation that procapsid expansion is strongly inhibited by salt and increased temperature, both of which increase the strength of hydrophobic interactions. For instance, expansion occurs efficiently at 4° C. but not at 25° C., a temperature range in which the strength of hydrophobic interactions increase to a maximum at ~20° C.[59; 61]. In sum, our data are consistent with a transition that requires overcoming hydrophobic interactions.

Figure 6:
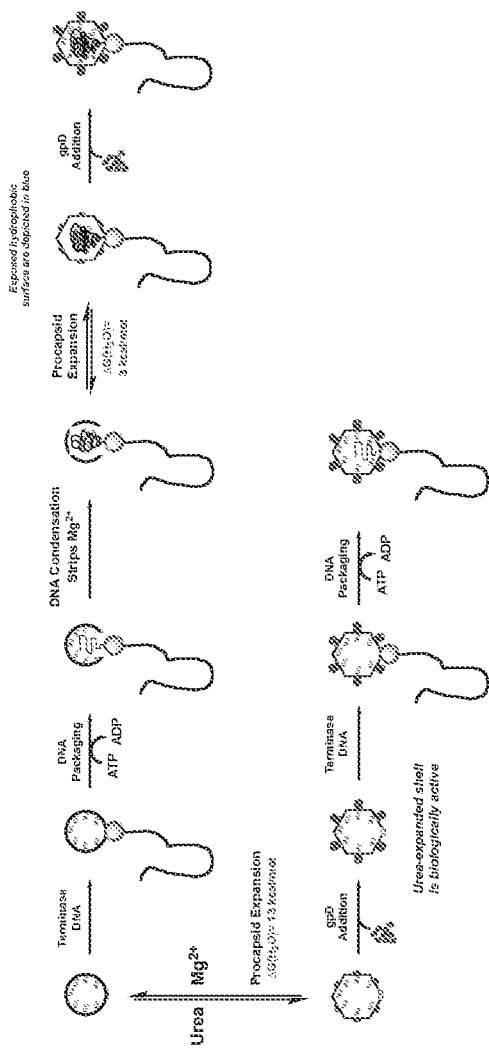
FIG. 6. Model for Reversible Procapsid Expansion and gpD Addition. Upper Pathway. Procapsid expansion is triggered by DNA packaging in vivo. $Mg^{2+}$ strongly stabilizes the procapsid conformation. Packaged DNA binds $Mg^{2+}$ at the interior procapsid surface, lowering the free energy required for the expansion transition. GpD trimer spikes assemble at hydrophobic patches exposed at the icosahedral three-fold axes of the expanded shell lattice and stabilize the particle. Lower Pathway. Procapsid expansion is triggered by urea in vitro. $Mg^{2+}$ strongly stabilizes the procapsid conformation and higher concentrations of urea are required to trigger the transition. GpD trimer spikes assemble at hydrophobic patches exposed at the icosahedral three-fold axes of the expanded shell lattice. The decorated particles are structurally robust and biologically active.

The model proposed in FIG. 6 is further consistent with the large denaturant "m" value obtained in our thermodynamic analysis of urea-triggered expansion. This value reflects the dependence of ΔG on denaturant concentration, which is related to the heat capacity change (ΔCp). This in turn is related to the change in hydrophobic surface area; the larger the m, the greater hydrophobic surface area is exposed in the transition[33]. The m value obtained here (>4 kcal/mol·molar) is relatively large compared to most protein unfolding reactions (typically 1-3 kcal/mol·molar[32; 34; 35; 62]). This indicates that a large hydrophobic surface area is exposed upon capsid expansion. Importantly, while the $\Delta G(H_2O)$ for expansion increases with increasing magnesium concentration, the denaturant m value remains relatively constant. This indicates that while magnesium stabilizes the procapsid state, it does not affect the change in hydrophobic surface area exposed upon transition to the expanded conformation. In other words, the conformation of the expanded state is the same regardless of the $Mg^{2+}$ concentration, as would be expected of a simple two-state transition.

Mechanism for Addition of gpD to the Expanded Capsid Lattice. The terminase motor packages DNA to liquid crystalline density within the capsid, which generates over 20 atmospheres of internal pressure[20; 63; 64; 65]. Viral decoration proteins add to the surface of the expanded capsid structure to stabilize the shell against the tremendous internal forces generated by the tightly packed DNA[20; 40; 41]. Specifically, the λ gpD protein assembles as a trimeric spike at the three-fold axes of the expanded capsid lattice[23; 41]. While gpD is dispensable for packaging of duplexes up to ~40 kb, packaging of larger duplexes requires gpD to maintain capsid integrity[40].

Structural studies indicate that the base of the gpD trimer is hydrophobic and it has been proposed that the spike interacts with hydrophobic patches on the capsid surface[41; 66; 67]; however, biochemical evidence for this model is lacking. Our data indicate that procapsid expansion is associated with exposure of hydrophobic patches on the capsid surface. We propose that these patches, which are buried in the procapsid conformation, are exposed at the icosahedral three-fold axes of the expanded shell and provide a nucleation site for assembly of the gpD trimer. Importantly, gpD adds to the surface of the expanded capsid efficiently at room temperature but only poorly at 4° C. (data not shown; see[39]); this temperature dependence is consistent with an increase in hydrophobic binding energy within this temperature range (vide supra)[59; 61].

Although our data show that expansion of the λ procapsid is fully reversible, gpD addition effectively locks the capsid shell into the expanded state. Indeed, large-scale conformational changes accompany DNA packaging in all of the complex dsDNA viruses and this is intrinsically irreversible. In vivo, these transitions are further made irreversible by proteolytic cleavage events, capsid protein cross-linking events, or the addition of decoration proteins as is observed in λ. Subsequently, "finishing" proteins add in an ordered, step-wise sequence, interactions that are nucleated by addition of the previous protein. In this manner, the particle progresses to the next step of assembly to minimize "off-pathway" intermediates and ensures fidelity in the assembly process.

Why do Procapsids Expand? Procapsid expansion is a common feature in the packaging of viral DNA but it is not clear why this is necessary. One possibility is that the assembly of a procapsid shell provides a mechanism for the terminase packaging motor to select only packaging competent shells. This presumes that pre-expanded capsids represent defective, off pathway intermediates that may result from aborted packaging events; however, our data demonstrate that the expanded λ capsid is catalytically competent and packages DNA quite efficiently. Indeed, this has similarly been demonstrated in the bacteriophage T4 system[68; 69]. Thus, while DNA packaging triggers the transition in vivo, expansion per se does not influence the capacity of the shell to accept the viral genome.

This begs the question as to why viruses utilize a procapsid structure at all. One possibility proposed by Johnson and co-workers is that the extensive interactions between the protein subunits assembled into the mature capsid shell are unlikely to form in a single assembly step[55]. This model suggests that the procapsid represents a metastable intermediate that is required for fidelity in shell assembly and that expansion is a consequence of the transition to the stable mature shell. Such a transition implies irreversibility; however, our data show that this need not be the case.

Conclusions. We have demonstrated that magnesium and urea stabilize the contracted and expanded conformations of the λ capsid shell, respectively. The λ system is unique in that expansion is fully reversible, which has allowed thermodynamic characterization of the transition. Expansion of the shell is associated with exposed hydrophobic surface area to which the gpD decoration protein adds. This stabilizes the expanded capsid lattice, abrogates contraction, and provides structural integrity so that the genome can be tightly packaged into the capsid interior. This work further provides mechanistic insight into how DNA packaging triggers shell expansion that is generalizable to the complex dsDNA viruses, both prokaryotic and eukaryotic.

Materials And Methods For Example 1

Materials and Methods. Tryptone, yeast extract, and agar were purchased from DIFCO. Molecular biology enzymes and mature λ DNA were purchased from New England Biolabs. Chromatography media was purchased from GE Healthcare and urea was purchased from Fisher Scientific. All other materials were of the highest quality available. Unless otherwise stated, Tris buffers were adjusted to the indicated pH at a temperature of 4° C. Bacterial cultures were grown in shaker flasks utilizing an Innova 4430 incubator-shaker. All protein purifications utilized the Amersham Biosciences ÄKTApurifier™ core 10 System from GE Healthcare. UV-VIS absorbance spectra were recorded on a Hewlett-Packard HP8452A spectrophotometer. Sucrose density gradients were prepared using a Biocomp Model 107 Gradient Master® and gradient centrifugation utilized a Beckman L-90K ultracentrifuge with a SW 28 rotor.

Protein Purification. λ terminase and the *Escherichia coli* Integration Host Factor (IHF) were purified as previously described[70; 71]. The gpD decoration protein was purified by our published protocol[36], with modification. Briefly, gpD was expressed from the pT7Cap vector and ammonium sulfate was added to the cell lysis supernatant to 50% saturation. The mixture was gently stirred on ice for 50 minutes and insoluble protein was removed by centrifugation (9 K×g, 20 minutes). The supernatant was adjusted to 90% ammonium sulfate, stirred on ice for 50 minutes and insoluble protein was harvested by centrifugation (30 K×g, 30 minutes). The pellet was resuspended in 20 mM Tris buffer, pH 8, containing 1 mM EDTA and 15 mM NaCl and the sample was applied to a DEAE column equilibrated with the same buffer. The column flow-through fraction, which contained gpD, was applied to a S-300 gel filtration column equilibrated and developed with 20 mM Tris buffer, pH 8, containing 1 mM EDTA, and 100 mM NaCl. The gpD containing fractions were pooled, dialyzed into 20 mM Tris buffer, pH 8, containing 1 mM EDTA and concentrated to ~500 µM using an Amicon® centrifugal filter unit. All of our purified protein preparations were homogenous as determined by SDS-PAGE (not shown).

Procapsid Purification. λ procapsids were purified as described previously[36], but the purified preparations contained variable amounts of pre-expanded procapsids. To obtain a homogenous preparation of unexpanded procapsids, the sample was fractionated on a 0.8% agarose gel, which readily separates expanded capsids from unexpanded procapsids (see FIG. 2). The lower band was excised with a sterile razor blade and the unexpanded procapsids were eluted from the gel slice into Buffer A (25 mM Tris base, 192 mM glycine, and 1 mM MgCl$_2$) using a Bio-Rad Model 422 Electro-eluter (100 V for 1 hour). The sample was dialyzed into TMB buffer (50 mM Tris buffer, pH 8, containing 15 mM MgCl$_2$ and 7 mM β-ME) and concentrated using an Amicon® centrifugal filter unit.

Procapsid Expansion and Buffer Exchange Protocol. A freshly prepared stock solution of 8 molar urea in water was used for all of the expansion experiments. Unless otherwise specified, equal volumes of purified procapsids and 8 molar urea were mixed to afford a reaction mixture (20 µl) containing 30 nM procapsids in 10 mM Tris buffer, pH 8, containing 2.5 molar urea and 3 mM MgCl$_2$. Subsequent modification of the expansion reaction composition was accomplished by a buffer exchange protocol. Briefly, a sufficient volume of buffer was added to adjust the magnesium and urea concentrations as indicated in each experiment and the mixture was then concentrated to its original volume using an Amicon® centrifugal filter unit. The expansion reaction mixtures were incubated on ice for 15 minutes and procapsid expansion analyzed by agarose gel assay, as described below.

Analysis of Capsid Expansion and Contraction. The samples were applied to a 0.8% agarose gel and electrophoresis was performed at 110 v for 100 minutes. The contracted procapsid (lower) and expanded capsid (upper) bands were visualized by staining with Coomassie brilliant blue. Video images of the de-stained gels were captured using an EpiChemi[3] darkroom system with a Hammamatsu camera (UVP Bioimaging Systems) and the video images were quantified using either the LabWorks 4.6 (UVP Bioimaging Systems) or the ImageQuant (Molecular Dynamics) software packages.

Thermodynamic Analysis of Urea-Triggered Procapsid Expansion. Procapsid expansion in urea is a two-state, reversible transition and we adapted analytical tools developed to characterize reversible protein unfolding transitions to analyze the data, as follows. The fraction of procapsids in the expanded state was quantified by agarose gel assay (above). The data were fit by nonlinear, least-squares analysis using the linear extrapolation method as outlined by Santoro and Bolen[32] according to equation 1:

$$F_E = \frac{(m_P \cdot [U] + b_P) + (M_E \cdot [U] + b_E) *}{1 + \exp\left[-\left(\frac{\Delta G_{H_2O}}{RT} + \frac{m_G * [U]}{RT}\right)\right]} \quad (1)$$

where $F_E$ is the fraction of capsids in the expanded state as a function of the urea concentration ([U]). The values $m_P$ and $m_E$ represent the slopes and $b_P$ and $b_E$ represent the y-intercepts of the pre- and post-transition baselines, respectively. R is the ideal gas constant and T is the temperature (kelvin). The free energy of procapsid expansion ($\Delta G_{H_2O}$; kcal/mol) and the denaturant m value ($m_G$; kcal/mol·molar) represent the intercept and slope, respectively, of the linear dependence of the expansion transition energy as a function of denaturant concentration. Each data set was fit to equation 1 with $m_P$, $b_P$, $m_E$, $b_E$, $\Delta G_{H_2O}$, and $m_G$ as parameters using the IGOR® graphics/analysis package (WaveMetrics, Lake Oswego, Oreg.).

The urea-expansion data were also fit according to equation 2:

$$F_E = \text{Base} + \left[\frac{\text{Max}}{1 + \exp\left(\frac{[\text{urea}]_{1/2} - [\text{urea}]}{m_T}\right)}\right] \quad (2)$$

where $F_E$ is the fraction of capsids in the expanded state as a function of the urea concentration ([urea]). Base and Max represent the pre- and post-transition baselines, $m_T$ is the transition slope, and $[\text{urea}]_{1/2}$ is the concentration of urea required to expand half of the procapsids to the expanded state. Each data set was fit to equation 2 with Base, Max, $C_{1/2}$ and $m_T$ as parameters using the IGOR® graphics/analysis package (WaveMetrics, Lake Oswego, Oreg.).

Analysis of $Mg^{2+}$-Triggered Capsid Contraction. Expanded capsids were prepared as described above in the absence and presence of urea at the indicated concentration. The samples were incubated in the presence of the indicated concentration of $MgCl_2$ at room temperature for five minutes and the fraction of expanded capsid structures quantified by agarose gel and video densitometry as described above. The data were fit by nonlinear, least-squares analysis according to equation 3:

$$F_E = \text{Base} + \left[\frac{\text{Max}}{1 + \exp\left(\frac{[\text{Mg}]_{1/2} - [\text{Mg}]}{m_T}\right)}\right] \quad (2)$$

where $F_E$ is the fraction of capsids in the expanded state as a function of the $Mg^{2+}$ concentration, [Mg]. Base and Max represent the pre- and post-transition baselines, $m_T$ is the transition slope, and $[\text{Mg}]_{1/2}$ is the concentration of $Mg^{2+}$ required to contract half of the expanded shells to the procapsid state. Each data set was fit to equation 2 with Base, Max, $[\text{Mg}]_{1/2}$ and $m_T$ as parameters using the IGOR® graphics/analysis package (WaveMetrics, Lake Oswego, Oreg.).

DNA Packaging into Expanded Capsids. The in vitro DNA packaging reaction was performed as described previously[36], with modification. Briefly, purified procapsids (40 nM capsid; 16.6 μM gpE capsid protein) were expanded as described above and then buffer exchanged into 10 mM Tris buffer, pH 8. Purified gpD was then added to a final concentration of 15 μM and the mixture was incubated for 30 minutes at room temperature. The gpD-coated, expanded capsids were added to a reaction mixture containing 50 mM Tris buffer, pH 7.4, containing 9 mM NaCl, 5 mM $MgCl_2$, 2 mM spermidine, 1.3 mM β-ME, 1 mM ATP, 100 nM IHF, and 2 nM mature λ DNA. The packaging reaction (20 μl) was initiated with the addition of terminase holoenzyme to a final concentration of 100 nM and allowed to proceed for 30 minutes at room temperature. DNase (10 μg/ml) was then added to the reaction mixture and incubated at room temperature for five minutes. The DNase reaction was stopped with the addition of phenol:chloroform (21 μl) and the aqueous layer was removed and loaded onto a 0.8% agarose gel. Packaged (DNase resistant) DNA was quantified by video densitometry as previously described[36].

REFERENCES FOR EXAMPLE 1

1. Calendar, R. & Abedon, S. T. (2006). *The Bacteriophages*, Oxford University Press, New York, N.Y.
2. Roizman, B. & Palese, P. (1996). Multiplication of Viruses: An Overview. In *Fields Virology* Third edit. (Fields, B. N., Knipe, D. M. & Howley, P. M., eds.), pp. 101-11. Lippincott-Raven, New York, N.Y.
3. Rao, V. B. & Feiss, M. (2008). The bacteriophage DNA packaging motor. *Annu Rev Genet* 42, 647-81.
4. Roizman, B., Knipe, D. M. & Whitley, R. J. (2007). Herpes Simplex Viruses. In *Fields Virology* Fifth edit. (Knipe, D. M. & Howley, P. M., eds.), pp. 2501-2602. Lippincott. Williams and Wilkins, Philiedphia, Pa.
5. Catalano, C. E. (2005). Viral Genome Packaging Machines: An Overview. In *Viral Genome Packaging Machines: Genetics, Structure, and Mechanism* (Catalano. C. E., ed.), pp. 1-4. Kluwer Academic/Plenum Publishers. New York, N.Y.
6. Baines. J. D. & Weller, S. K. (2005). Cleavage and Packaging of Herpes Simplex Virus 1 DNA. In *Viral Genome Packaging Machines: Genetics, Structure, and Mechanism* (Catalano. C. E., ed.), pp. 135-149. Kluwer Academic/Plenum Publishers. New York, N.Y.
7. Feiss, M. & Catalano, C. E. (2005). Bacteriophage Lambda Terminase and the Mechanism of Viral DNA Packaging. In *Viral Genome Packaging Machines: Genetics. Structure, and Mechanism* (Catalano, C. E., ed.), pp. 5-39. Kluwer Academic/Plenum Publishers, New York, N.Y.
8. Jardine, P. J. & Anderson, D. L. (2006). DNA Packaging in Double-Stranded DNA Phages. In *The Bacteriophages* 2nd edit. (Calendar, R. & Abedon, S. T., eds.), pp. 49-65. Oxford University Press, New York, N.Y.
9. Baines, J. D. & Duffy. C. (2006). Nucloeocapsid Assembly and Envelopment of Herpes Simplex Virus. In *Alpha Herpesviruses: Molecular and Cellular Biology* (Sandri-Goldin, R. M., ed.), pp. 175-204. Caister Academic Press, Norfolk, Va.
10. Alonso. J. C., Tavares, P., Lurz, R. & Trautner, T. A. (2006). Bacteriophage SPPI. In *The Bacteriophages* 2nd edit. (Calendar, R. & Abedon, S. T., eds.), pp. 331-349. Oxford University PRess, New York, N.Y.
11. Hendrix, R. W. & Casjens. S. (2006). Bacteriophage Lambda and its Genetic Neighborhood. In *The Bacteriophages* 2nd edit. (Calendar, R. & Abedon, S. T., eds.), pp. 409-447. Oxford University Press, New York, N.Y.
12. Hendrix, R. W., Roberts, J. W., Stahl. F. W. & Weisberg, R. A. (1983). *Lamba II*, Cold Spring Harbor Laboratory, Cold Spring Harbor, N.Y.

13. Medina. E., Wieczorek, D. J., Medina, E. M., Yang. Q., Feiss, M. & Catalano, C. E. (2010). Assembly and Maturation of the Bacteriophage Lambda Procapsid: gpC Is the Viral Protease. *J. Mol. Biol.* 401, 813-830.
14. Georgopoulos, C., Tilly, K. & Casjens, S. (1983). Lambdoid Phage Head Assembly. In *Lambda II* (Hendrix, R. W., Roberts, J. W., Stahl, F. W. & Weisberg, R. A., eds.), pp. 279-304. Cold Spring Harbor Laboratory, Cold Spring Harbor, N.Y.
15. Kochan, J. & Murialdo, H. (1983). Early Intermediates in Bacteriophage Lambda Prohead Assembly. II. Identification of Biologically Active Intermediates. *Virology* 131, 100-115.
16. Medina. E. M., Andrews, B. T., Nakatani, E. & Catalano, C. E. (2011). The Bacteriophage Lambda gpNu3 Scaffolding Protein is an Intrinsically Disordered and Biologically Functional Procapsid Assembly Catalyst. *Journal of Molecular Biology* 412, 723-736.
17. Johnson, J. E. (2010). Virus Particle Maturation: Insights into Elegantly Programmed Nanomachines. *Current Opinion in Structural Biology* 20, 210-216.
18. Fane, B. A. & Prevelige, P. E. (2003). Mechanism of Scaffolding-Assisted Viral Assembly. In *Virus Structure* (Wah, C. & John, E. J., eds.), Vol. Volume 64, pp. 259-299. Academic Press, Oxford, UK.
19. Dokland, T. (1999). Scaffolding Proteins and their Role in Viral Assembly. *Cellular and Molecular Life Sciences* 56, 580-603.
20. Fuller, D. N., Raymer, D. M., Rickgauer, J. P., Robertson, R. M., Catalano, C. E., Anderson, D. L., Grimes, S. & Smith, D. E. (2007). Measurements of single DNA molecule packaging dynamics in bacteriophage lambda reveal high forces, high motor processivity, and capsid transformations. *J Mol Biol* 373, 1113-22.
21. Hohn, T., Wurtz, M. & Hohn, B. (1976). Capsid Transformation During Packaging of Bacteriophage Lambda DNA. *Phil. Trans. R. Soc. Lond.* 276, 51-61.
22. Hohn, T., Morimasa, T. & Tsugita, A. (1976). The Capsid Protein of Bacteriophage Lambda and of its Prehead. *Journal of Molecular Biology* 105, 337-342.
23. Dokland, T. & Murialdo, H. (1993). Structural Transitions During Maturation of Bacteriophage Lambda Capsids. *J. Mol. Biol.* 233, 682-694.
24. Steven, A. C., Heymann, J. B., Cheng, N., Trus, B. L. & Conway, J. F. (2005). Virus Maturation: Dynamics and Mechanism of a Stabilizing Structural Transition that Leads to Infectivity. *Current Opinion in Structural Biology* 15, 227-236.
25. Black, L. W. (1989). DNA Packaging in dsDNA Bacteriophages. *Annual Review of Microbiology* 43, 267-292.
26. Duda, R. L., Hempel, J., Michel, H., Shabanowitz, J., Hunt, D. & Hendrix, R. W. (1995). Structural Transitions During Bacteriophage HK97 Head Assembly. *Journal of Molecular Biology* 247, 618-635.
27. Galisteo, M. L. & King, J. (1993). Conformational Transformations in the Protein Lattice of Phage P22 Procapsids. *Biophysical Journal* 65, 227-235.
28. Kunzler. P. & Hohn, T. (1978). Stages of Bacteriophage Lambda Head Morphogenesis: Physical Analysis of Particles in Solution. *Journal of Molecular Biology* 122, 191-211.
29. Imber, R., Tsugita, A., Wurtz, M. & Hohn, T. (1980). Outer Surface Protein of Bacteriophage Lambda. *Journal of Molecular Biology* 139, 277-295.
30. Newcomb, W. W., Homa, F. L., Thomsen, D. R. Booy, F. P., Trus, B. L., Steven, A. C., Spencer. J. V. & Brown, J. C. (1996). Assembly of the Herpes Simplex Virus Capsid: Characterization of Intermediates Observed During Cell-free Capsid Formation. *Journal of Molecular Biology* 263, 432-446.
31. Conway, J. F., Duda, R. L., Cheng, N., Hendrix, R. W. & Steven, A. C. (1995). Proteolytic and Conformational Control of Virus Capsid Maturation: The Bacteriophage HK97 System. *Journal of Molecular Biology* 253, 86-99.
32. Santoro, M. M. & Bolen. D. W. (1988). Unfolding Free Energy Changes Determined by the Linear Extrapolation Method. 1. Unfolding of Phenylmethanesulfonyl Alpha-Chymotrypsin Using Different Denaturants. *Biochemistry* 18, 8063-8068.
33. Pace, C. N. & Shaw, K. L. (2000). Linear Extrapolation Method of Analyzing Solvent Denaturation Curves. *Proteins* Suppl. 4, 1-7.
34. Santoro, M. M. & Bolen, D. W. (1992). A Test of the Linear Extrapolation of Unfolding Free Energy Changes over an Extended Denaturant Concentration Range. *Biochemistry* 31, 4901-4907.
35. Bolen, D. W. & Santoro. M. M. (1988). Unfolding free energy changes determined by the linear extrapolation method. 2. Incorporation of delta G degrees N-U values in a thermodynamic cycle. *Biochemistry* 18, 8069-8074.
36. Yang, Q. & Catalano, C. E. (2003). Biochemical characterization of bacteriophage lambda genome packaging in vitro. *Virology* 305, 276-87.
37. Gaussier, H., Yang. Q. & Catalano, C. E. (2006). Building a virus from scratch: assembly of an infectious virus using purified components in a rigorously defined biochemical assay system. *J Mol Biol* 357, 1154-66.
38. Murialdo, H. & Becker, A. (1978). Head Morphogenesis of Complex Double-Stranded Deoxyribonucleic Acid Bacteriophages. *Microbiological Reviews* 42, 529-576.
39. Medina, E. (2010). Growing Pains of Bacteriophage Lambda: Examination of the Maturation of Procapsids into Capsids. Ph.D., University of Washington.
40. Yang, Q., Maluf, N. K. & Catalano. C. E. (2008). Packaging of a Unit-Length Viral Genome: The Role of Nucleotides and the gpD Decoration Protein in Stable Nucleocapsid Assembly in Bacteriophage Lambda. *Journal of Molecular Biology* 383, 1037-1048.
41. Lander, G. C., Evilevitch, A., Jeembaeva, M., Potter, C. S., Carragher, B. & Johnson, J. E. (2008). Bacteriophage Lambda Stabilization by Auxiliary Protein gpD: Timing, Location, and Mechanism of Attachment Determined by Cryo-EM. *Structure* 16, 1399-1406.
42. Conway, J. F., Cheng, N., Ross, P. D., Hendrix, R. W., Duda, R. L. & Steven, A. C. (2007). A Thermally Induced Phase Transition in a Viral Capsid Transforms the Hexamers, Leaving the Pentamers Unchanged. *Journal of Structural Biology* 158, 224-232.
43. Jardine, P. J. & Coombs, D. H. (1998). Capsid Expansion Follows the Initiation of DNA Packaging in Bacteriophage T4. *Journal of Molecular Biology* 284, 661-672.
44. Lee, K. K., Tsuruta, H., Hendrix, R. W., Duda. R. L. & Johnson, J. E. (2005). Cooperative Reorganization of a 420 Subunit Virus Capsid. *Journal of Molecular Biology* 352, 723-735.
45. Lata, R., Conway, J. F., Cheng, N., Duda, R. L., Hendrix, R. W., Wikoff, W. R., Johnson, J. E., Tsuruta, H. & Steven, A. C. (2000). Maturation Dynamics of a Viral Capsid: Visualization of Transitional Intermediate States. *Cell* 100, 253-263.
46. Fuller. D. N., Raymer, D. M., Kottadiel, V. I., Rao, V. B. & Smith, D. E. (2007). Single phage T4 DNA packaging motors exhibit large force generation, high velocity, and dynamic variability. *Proc Natl Acad Sci USA* 104, 16868-73.
47. Tsay. J. M., Sippy, J., Feiss, M. & Smith, D. E. (2009). The Q motif of a viral packaging motor governs its force generation and communicates ATP recognition to DNA interaction. *Proc Natl Acad Sci USA* 106, 14355-60.
48. Salunke, D. M., Caspar. D. L. & Garcea, R. L. (1989). Polymorphism in the Assembly of Polyomavirus Capsid Protein VP1. *Biophysical Journal* 56, 887-900.
49. Salunke, D. M., Caspar, D. L. D. & Garcea, R. L. (1986). Self-assembly of purified polyomavirus capsid protein VP1. *Cell* 46, 895-904.
50. Brady. J. N., Winston, V. D. & Consigli. R. A. (1977). Dissociation of Polyoma Virus by the Chelation of Calcium Ions Found Associated with Purified Virions. *The Journal of Virology* 23, 717-724.
51. Yanagi. K. & Harada. S. (1989). Destabilization of Herpes Simplex Virus Type 1 Virions by Local Anesthetics, Alkaline pH, and Calcium Depletion. *Archives Virology* 108, 151-159.
52. Sternberg, N. & Weisberg, R. (1977). Packaging of Coliphage Lambda DNA: II. The Role of the Gene D Protein. *Journal of Molecular Biology* 117, 733-759.
53. Sternberg, N. & Hoess, R. H. (1995). Display of peptides and proteins on the surface of bacteriophage lambda. *Proceedings of the National Academy of Sciences* 92, 1609-1613.
54. Bode, V. C. & Harrison, D. P. (1973). Distinct Effects of Diamines, Polyamines, and Magnesium ions on the Stability of Lambda Phage Heads. *Biochemistry* 12, 3193-3196.
55. Gertsman, I., Gan, L., Guttman. M., Lee, K., Speir, J. A., Duda. R. L., Hendrix. R. W., Komives, E. A. & Johnson, J. E. (2009). An Unexpected Twist in Viral Capsid Maturation. *Nature* 458, 646-650.
56. Nurmemmedov, E., Castelnovo, M., Medina, E., Catalano, C. E. & Evilevitch, A. (2012). Challenging Packaging Limits and Infectivity of Phage Lambda. *Journal of Molecular Biology* 415, 263-273.
57. Fuller, D. N., Rickgauer, J. P., Jardine, P. J., Grimes, S., Anderson. D. L. & Smith, D. E. (2007). Ionic effects on Viral DNA Packaging and Portal Motor Function in Bacteriophage phi29. *Proceedings of the National Academy of Sciences* 104, 11245-11250.
58. Yang, Q. Catalano, C. E. & Maluf, N. K. (2009). Kinetic Analysis of the Genome Packaging Reaction in Bacteriophage Lambda. *Biochemistry* 48, 10705-10715.
59. Baldwin, R. L. (1986). Temperature Dependence of the Hydrophobic Interaction in Protein Folding. *Proc Natl Acad Sci USA* 83, 8069-8072.
60. Makhatadze, G. I. & Privalov, P. L. (1992). Protein Interactions with Urea and Guanidinium Chloride: A Calorimetric Study. *Journal of Molecular Biology* 226, 491-505.
61. Schellman, J. A. (1997). Temperature, Stability, and the Hydrophobic Intereaction. *Biophysical J.* 73, 2960-2964.
62. Myers, J. K., Pace, C. N. & Scholtz, J. M. (1995). Denaturant m values and Heat Capacity Changes: Relation to Changes in Accessible Surface Areas of Protein Unfolding. *Protein Science* 4, 2138-2148.
63. Tzlil, S., Kindt, J. T., Gelbart. W. M. & Ben-Shaul, A. (2003). Forces and Pressures in DNA Packaging and Release from Viral Capsids. *Biophysical Journal* 84, 1616-1627.
64. Evilevitch, A., Lavelle. L., Knobler. C. M., Raspaud, E. & Gelbart. W. M. (2003). Osmotic Pressure Inhibition of DNA Ejection from Phage. *Proceedings of the National Academy of Sciences* 100, 9292-9295.
65. Nurmemmedov, E., Castelnovo, M., Catalano, C. E. & Evilevitch, A. (2007). Biophysics of viral infectivity: matching genome length with capsid size. *Q Rev Biophys* 40, 327-56.
66. Yang, F., Forrer, P., Dauter, Z., Conway, J. F., Cheng, N., Cerritelli, M. E., Steven, A. C., Pluckthun, A. & Wlodawer, A. (2000). Novel Fold and Capsid-Binding Properties of the Lambda Phage Display Platform Protein gpD. *Nature Structural Biology* 7, 230-237.
67. Iwai, H., Forrer, P., Pluckthun, A. & Guntert, P. (2005). NMR Solution Structure of the Monomeric Form of the Bacteriophage Lambda Capsid Stabilizing Protein gpD. *Journal of Biomolecular NMR* 31, 351-356.
68. Rao, V. B. & Black, L. W. (1985). DNA packaging of bacteriophage T4 proheads in vitro. Evidence that prohead expansion is not coupled to DNA packaging. *J Mol Biol* 185, 565-78.
69. Zhang. Z., Kottadiel, V. I., Vafabakhsh, R., Dai, L., Chemla, Y. R., Ha, T. & Rao, V. B. (2011). A Promiscuous DNA Packaging Machine from Bacteriophage T4. *PLoS Biol* 9, e1000592.
70. Tomka, M. A. & Catalano, C. E. (1993). Physical and kinetic characterization of the DNA packaging enzyme from bacteriophage lambda. *J Biol Chem* 268, 3056-65.
71. Filutowicz, M., Grimek, H. & Appekt, K. (1996). Purification of the *Escherichia coli* Integration Host Factor (IHF) in One Chromatographic Step. *Gene* 147, 149-150.

EXAMPLE 2

With the development of phage display as a platform for vaccines, viral nanoparticles are transitioning from research tools to therapeutic delivery systems. The popularity of lambda in phage display applications has been due in part to the ease in fusing functional peptides and proteins to the capsid decoration protein gpD. The full potential of the lambda capsid as a therapeutic nanoparticle has yet to be exploited and we are developing bacteriophage lambda for use as a theragnostic nanoparticle system.

To date, all gpD fusion constructs that have been used for phage display applications have been constructed in vivo. These systems have thus been limited to peptide and protein fusion constructs expressed within *Escherichia coli* cells in the context of an infectious virus. For instance, a gpD-yellow fluorescence protein fusion construct (gpD-EYFP) expressed from a lambda lysogen in vivo affords infectious virus particles decorated with EYFP {Alvarez, 2007 #680}. We have previously demonstrated that purified gpD can be efficiently added to expanded lambda capsids in a defined biochemical reaction mixture in vitro. Here we demonstrate that purified gpD-GFP can similarly be used to decorate the lambda capsid in vitro. We have further constructed several single-cysteine gpD proteins that allow site-specific modification of the decoration protein with non-proteinaceous ligands. We show that one such construct, gpD(S42C), can be selectively modified with mannose. The resulting synthetic gpD "glycoprotein" is functional in the capsid decoration reaction. Finally, we demonstrate that capsids can be modified with gpD-wild type, gpD-GFP, and gpD-mannose decoration proteins in a defined and tunable surface density. Importantly, the poly-display shell is competent in the DNA packaging reaction in vitro, indicating that the capsid can be filled with functional genes as desired. This work sets the stage for the construction of "designer" nanoparticles that can be manufactured to display peptides, proteins, carbohydrates, synthetic polymers, and small molecules in a defined composition, symmetrically displayed on the shell surface, and that can carry specific genes for targeted delivery.

We have developed a hybrid theragnostic nanoparticle assembly that harnesses the bacteriophage lambda system for the targeted delivery of drugs and molecular probes. This invention is based on the assembly of engineered viral capsid shells in vitro using purified scaffold and major capsid proteins. For delivery applications. DNA is efficiently packaged into the decorated capsids and can modified to carry specific genes of interest. In addition, the surface of the particle is symmetrically decorated with an external capsid protein that assembles as trimer spikes at the 140 three-fold icosahedral axes. The decoration protein can be specifically conjugated with protein and/or synthetic moieties in defined ratios to enhance cellular targeting/uptake of the particle, to avoid immune surveillance, or alternatively, to enhance immune response to the capsid as a defined antigenic particle. These engineered viral nanoparticles can be tailored in specific ways to afford a delivery vehicle with defined surface characteristics for both diagnostic and therapeutic applications.

Introduction

A brief background of lambda replication relevant to developing a lambda nanoparticle is presented in FIG. 7A. The capsid assembly pathway in vivo initiates with the assembly of the viral portal protein (gpB) into a dodecameric ring-like structure. The gpNu3 scaffolding protein mediates ring assembly and then chaparones self-assembly of the the major capsid protein (gpE) into an icoshahedrial shell. This "immature procapsid" contains 420 copies of gpE, a single portal ring situated at a unique vertex, and ~200 copies of gpNu3 inside the shell. A viral protease (gpC) is also incorporated into the immature capsid, which trims 12 residues from the N-terminus of gpB, digests gpNu3 and auto-proteolyzes so that the internal proteins can exit the shell. This affords the "mature procapsid" into which viral DNA is packaged.

Genome packaging is catalyzed by a terminase enzyme. Upon packaging ca. 15 kb duplex DNA, the shell undergoes a remarkable expansion process which results in thinning and increased angularization of the shell and a 2-fold increase in capsid volume. The gpD "decoration" protein is expressed in high-concentration in the phage-infected cell and is a monomer in solution: however, the protein self-assembles as trimer spikes at the 140 three-fold icosahedral axes of the expanded shell (420 copies per shell). GpD stabilizes the shell such that it can withstand the tremendous force generated upon packaging the 48.5 kb genome (>25 atmospheres). Subsequent addition of finishing proteins and a viral tail afford an infectious lambda particle (FIG. 7A).

The in vitro assembly system described in Example 1 provides an opportunity to decorate the lambda capsid with gpD-modified constructs under defined reaction conditions. Here we describe procedures that allow the assembly of hybrid theragnostic nanoparticles that harnesses the bacteriophage lambda system.

Lambda capsid assembly in vivo initiates with the formation of the portal complex, a dodecameric ring through which DNA enters the capsid during packaging and exits during infection of the host. Co-polymerization of the scaffolding protein (gpNu3) and the major capsid protein (gpE) nucleates at the portal, forming an immature procapsid shell composed of 415 copies of gpE (FIG. 7A). Within the procapsid interior are ~70-200 copies of gpNu3 and 10 copies of the protease (gpC). Residing at one of the 5-fold vertices of the icosahedral shell is the portal. The immature icoahedral shell is rounded in appearance with a diameter of 50-55 nm. Proteolysis by gpC causes maturation of the procapsid with the removal of gpC and gpNu3 from procapsid interior. Partial cleavage of the portal structure where approximately half of the portal proteins (gpB) is degraded to B* with the cleavage of the 20 N-terminal residues also occurs during procapsid maturation. The terminase complex packages lamdba DNA into the capsid interior, triggering expansion of the procapsid to the more angular capsid when approximately 30% is packaged. During expansion gpE undergoes conformational changes, which forms openings in the icosahedral capsid at its 3-fold vertices through which DNA can escape. To stabilize the expanded capsid, 420 copies of the head protein (gpD) add as trimers to the 3-fold vertices of the icosahedral capsid.

Lambda capsid expansion is strictly required for gpD addition. In vivo expansion is triggered during DNA packaging. In vitro expansion can be triggered by DNA packaging; however, it can also be artifically triggered by the denaturant urea, as described in example 1. The expanded capsids are then decorated with gpD in vitro, rendering them stable and biologically functional. Furthermore, tails can be attached to mature capsids forming biologically viable lambda viruses.

Phage display exploits gpD two-fold: its symmetric display and high copy number, at the surface of the icosahedral capsid. However, it is currently limited to proteinaceous ligands decorating an infectious virus since N- and C-terminal gpD fusion proteins are expressed from lysogens in vivo. Because gpD was be expressed and purified at high concentration and purity for structural determination, we constructed gpD expression vectors to show that gpD can be modified in vivo and in vitro and that the modified gpD can decorate the capsid surface in combination at defined ratios.

Materials and Methods

Materials. Terrific broth (Difco), tryptone, yeast extract, ampicillin, urea, and ThermoScientific "Halt"® EDTA-free protease inhibitor cocktail (100×) were purchased from Fisher Scientific. Mature λ DNA (cI857ind 1 Sam 7) was purchased from Invitrogen. Restriction enzymes were purchased from New England BioLabs. Chromatography media was purchased from GE Healthcare Life Sciences. All other materials were of the highest quality available. Unless otherwise stated, the pH of all buffers was adjusted at 4° C., Cell lysis utilized a Thermo Scientific IEC "French" laboratory press. All protein purifications utilized the Amersham Biosciences ÄKTApurifier™ core 10 System from GE Healthcare and sucrose gradients were prepared on a Bio-Comp 107ip Gradient Master. Protein concentrations were determined spectrally using a ThermoScientific NanoDrop 2000c spectrophotometer.

Construction of pT$_7$Cap Dam7am43. The plasmid pT$_7$capDam7am43 expresses the lambda major capsid protein (gpE), the scaffolding protein (gpNu3), the portal protein (gpB) and the capsid protease (gpC), which spontaneously assemble functional procapsids that can be purified in high yield {Yang, 2003 #16}. This vector was constructed by modification of pT$_7$cap {Yang, 2003 #16} to obviate the expression of gpD; codons 7 (UUU) and 43 (UCC) were mutated to amber stop codons (UAG) using the QuikChange II site-directed mutagenesis kit (Agilent) according to the manufacturers instructions.

Expression and Purification of Lambda Procapsids. Expression of procapsid proteins from pT$_7$capDam7am43 was performed as previously described for pT$_7$cap {Yang. 2003 #16} except that Terrific broth was used in place of 2×YT media. Procapsid were purified as described, with minor modification, and unless otherwise indicated all procedures were conducted at 4° C. and with ice-cold buffers. Briefly, the cell pellet was resuspended in 50 ml Buffer A (50 mM Tris, pH 8, containing 10 mM MgCl$_2$, 100 mM NaCl) containing 2 μg/ml DNase I and the cells were lysed by French press (2-3 passages, 650 psi). The lysate was clarified by centrifugation (7,650×g×25 minutes) and the procapsids were then harvested by centrifugation (131,453×g×3 hours). The procapsids were resuspended by overlaying 5 mL Buffer A onto the pellet overnight at 4° C. The supernatant was aspirated and then diluted with 15 mL TM buffer (50 mM Tris, pH 8, containing 20 mM MgCl$_2$), loaded onto a HiTrap Q (5 mL) column equilibrated with TM Buffer, and then eluted with a linear gradient to 1 molar NaCl. The procapsid containing fractions (eluting at ~100 mM NaCl) were pooled, dialyzed against Buffer A, concentrated in Amicon Ultra-15 Filters (Millipore), applied to a 10-40% sucrose gradient in the same buffer, and centrifuged for 3 hours at 27,000 rpm (SW28 rotor). The procapsid band was visualized in ambient light, harvested by aspiration, and dialyzed against Buffer A. The dialyzed procapsids were then concentrated in Amicon Ultra-15 Filters between 100 and 300 nM prior to storage at 4° C.

Construction of Variant gpD Expression Plasmids. A summary of the proteins described in this work is presented in FIG. 2B, each of which was expressed from plasmids constructed as follows. First, vectors that express wild-type gpD protein, without and with a N-terminal hexaHistidine tag (gpD-WT and H6-gpD-WT, respectively) were constructed by PCR amplification of the D gene using genomic λ DNA as the template. The primers are described in Table 2 and the plasmids in Table 3. The expected PCR products were purified using the Wizard SV Gel and PCR Clean-up System (Promega), digested with NdeI and BamHI, and cloned into similarly digested pET21a (Novagen) to afford plasmids p(D) and p(H6D), both of which served as templates for mutagenesis of serine 42 to cysteine 42 via the QuikChange II site-directed mutagenesis kit (Agilent). The subsequent plasmids expressed mutated gpD proteins (gpD (S42C) and H6-gpD(S42C); FIG. 8B).

To generate gpD proteins containing N- and C-terminal linkers terminating with a unique cysteine residue (cys-gpD-H6 and H6-gpD-cys, respectively; FIG. 8B), the D gene was amplified by PCR using genomic λ DNA as a template and the primers presented in Table 2. The plasmids were constructed in the same manner as those described above.

To construct the plasmid expressing the N-terminal 6-histidine-tagged gpD, the D gene with a linker region encoded following its 3'-end was inserted in-frame into the vector pRSET_EmGFP (Invitrogen) between the restriction sites NdeI and NcoI. The PCR primers are described in Table 2. The plasmid was constructed in a similar manner as those described above.

Multiple cloning sites were added to the 5'- and 3'-end of the D gene separately to generate plasmids that will express proteins of choice fused to gpD via linkers at the N- and C-termini, respectively. The plasmid was constructed in a similar manner as those described above. The PCR primers are described in Table 2.

TABLE 2

Oligonucleotide primers. Original DNA sequences are underlined. Restriction sites are indicated by italics. Stop codons are in bold.

| Primer | Sequence |
|---|---|
| Mutagenesis | |
| Dam7 mut for | 5'-CGAGCAAAGAAACCTGAACCCATTACC-3' (SEQ ID NO: 11) |
| Dam7 mut rev | 3'-GGTAATGGGTTCAGGTTTCTTTGCTCG-5' (SEQ ID NO: 12) |
| Dam43 mut for | 5'-GCTGATGCTGGACACCTGAAGCCGTAAGCTGGTTGC-3' (SEQ ID NO: 13) |
| Dam43 mut rev | 3'-GCAACCAGCTTACGGCTTCAGGTGTCCAGCATCAGC-5' (SEQ ID NO: 14) |
| D(S42C) mut for | 5'-CCGCTGATGCTGGACACCTGCAGCCGTAAGCTGGTTGC-3' (SEQ ID NO: 15) |
| D(S42C) mut rev | 3'-GCAACCAGCTTACGGCTGCAGGTGTCCAGCATCAGCGG-5' (SEQ ID NO: 16) |
| Recombination | |
| D forward | 5'-GTGTAAGGGATGC*ATATG*ACGAGC-3' (SEQ ID NO: 17) |
| D-NdeI-BamHI for | 5'-CACACCAGTGTAAC*ATATG*GGA*TCC*ACGAGCAAAGAAACC-3' (SEQ ID NO: 18) |
| D rev | 3'-GTGATGAAGGG*GATCC*TTAACGATGC-5' (SEQ ID NO: 19) |
| H6-D for | 5'-CGATTTGCTGAAC*CATATG*CACCATCACCACCATCAC·ACGAGCAAAGAAACC-3' (SEQ ID NO: 20) |
| D-H6 rev | 3'-GCCGCACAGGG*GATCC*TTTTTAGTGATGATGGTGATGATGAACGATGCTG-5' (SEQ ID NO: 21) |
| cys-D for | 5'-GCCGTTAACGAT*CATATG*TGCGGATCAGGGTCAGGGAGTGGTAGCACGAGCAAAGAAACC-3' (SEQ ID NO: 22) |
| D-cys rev | 3'-CCCGTAAAAAAAGCCT*CGAG*TTAGCAACTTCCTGATCCAGAGCCAGATCCAACGATGCTGATTGC-5' (SEQ ID NO: 23) |
| MCS-D for | 5'-GCTGAACACACCAG*CTAGC*GGGGGGACT*GC*GACGAGCAAAGAAACC-3' (SEQ ID NO: 24) |

TABLE 2-continued

Oligonucleotide primers. Original DNA sequences are underlined. Restriction
sites are indicated by italics. Stop codons are in bold.

| Primer | Sequence |
| --- | --- |
| D-MCS rev | 3'-GGCGGCCTTTAGGCTAGCACCTCCAAGTCCAACGATGCTGATTGC-5' (SEQ ID NO: 25) |
| D-GFP rev | 3'-CCCGTAAAAACCATGGCAGTGCCGCCGCTTCCTCCTCCAGAGCCAAGTCCAACGATGCTGATTGCC-5' (SEQ ID NO: 26) |

TABLE 3

| Plasmid | Parental vector | Forward primer | Reverse primer |
| --- | --- | --- | --- |
| For gpD expression | | | |
| pD | pET21a | D for | D rev |
| pD(S42C) | pET21a | D(S42C) mut for | D(S42C) mut rev |
| pcys-D | pET21a | cys-D forw | D rev |
| pD-cys | pET21a | D-NdeI-BamHI forw | D-cys rev |
| pMCS-D | pET21a | MCS-D forw | D rev |
| pD-MCS | pET21a | D forw | D-MCS rev |
| pH6-gpD | pET21a | H6-D forw | D rev |
| pH6-gpD(S42C) | pET21a | D(S42C) mut forw | D(S42C) mut rev |
| pcys-gpD-H6 | pET21a | cys-D forw | D-H6 rev |
| pH6-gpD-cys | pET21a | H6-D forw | D-cys rev |
| pH6-gpD-DGFP | pRSET_EmGFP | H6-D forw | D-GFP rev |
| For procapsid expression | | | |
| pT7capDam7 | pKKT7E | Dam7 mut forw | Dam7 mut rev |
| pT7capDam7am43 | pKKT7E | Dam43 mut forw | Dam43 mut rev |

Purification of the Modified gpD Proteins. Expression of the gpD protein constructs was performed as described for procapsid expression above. For all constructs except gpD-GFP (see below), the induced cells were harvested by centrifugation (6,430×g×30 minutes) and the cell pellet was resuspended in Buffer B (20 mM Tris, pH 8, 20 mM NaCl, 0.1 mM EDTA, 1 mM DTT) containing 2 µg DNase I. The cells were lysed by French press (2-3 passages, 650 psi) and the lysate was clarified by centrifugation (7,650×g×25 minutes). The supernatant was heated to 50° C. for 15 minutes and immediately chilled on ice for 15 minutes; insoluble protein was removed by centrifugation (10,000×g×45 minutes). The supernatant was dialyzed against Buffer B at 4° C. overnight, clarified by centrifugation (10,000×g×10 min) and then loaded onto a HiTrap Q HP (5 mL) column equilibrated with Buffer B; gpD is not retained by the column, and the flow-through was collected and concentrated using Amicon Ultra-15 Filters. The concentrated protein was dialyzed overnight against Buffer B, clarified by centrifugation (10,000×g×10 min), and then loaded onto a Superose 6 10/300 (24 mL) column equilibrated with Buffer B. The gpD-containing fractions were collected, dialyzed overnight against Buffer B, and then stored at 4° C. until use.

Storage of gpD(S42C) in buffer containing β-ME resulted in adduction of the reducing agent to the cysteine residue to afford a mixed disulfide that precluded chemical modification with maleimide reagents (data not shown). Therefore, gpD(S42C)-containing fractions eluting from the Superose 6 column above were pooled, dialyzed against Buffer B in the absence of any reducing agent, and TCEP was added to a final concentration of 1 mM prior to storage at 4° C.

Finally, $H_6$-gpD-GFP was expressed as described above, except that 20 mM glucose was added to the growth media. The cell pellet was resuspended in Buffer H (20 mM Tris, pH 8, 150 mM NaCl, 0.1 mM EDTA, 7 mM β-ME, 25 mM imidazole) and the cells were disrupted by sonication (two 10 sec bursts separated by a 10-sec break). DNase 1 (2 µg/ml) and Thermo Scientific "Halt" EDTA-free protease inhibitor cocktail (1×) was added, and the resuspension was incubated on ice for 30 minutes. The mixture was again sonicated (10×10 sec pulses separated by 10 sec breaks in-between), and insoluble material was removed by centrifugation (8,000×g×10 minutes). The clarified lysate was loaded onto a HisTrap FF (5 mL) column equilibrated with Buffer H, and the proteins were eluted with a 10-column volume gradient to 500 mM imidazole. The $H_6$-gpD-GFP-containing fractions (bright green in color) were dialyzed overnight against Buffer H (minus imidazole), concentrated using an Amicon Ultra-0.5 filter and stored at 4° C. until use.

Synthesis of 6'-Maleimidohexanamido-polyethyleneglycol mannoside. A solution of 2-(2-(2-(Amido)ethyoxy-ethoxy)ethyl-O-α-D-mannoside (20 mg, $6.4 \times 10^2$ mmol) in methanol (1 ml) was added to a solution of 6-maleimidohexanoic acid N-hydroxysuccinimide ester (25 mg, $7.7 \times 10^{-2}$ mmol) in methanol (0.5 ml). The reaction mixture was stirred at RT for 2 hrs. The desired product was obtained after removal of solvent under reduced pressure following purification by silica column chromatography. The identity of product was confirmed by mass spectrometry and by 1H and 13C NMR.

Conjugation and Purification of Mannose-Conjugated gpD(S42C). The H6-gpD(S42C) stock solution was dialyzed into PBS buffer (1 ml) to which a solution of maleimide-activated mannose in 50 mM PBS buffer, pH 6.6 (800 µL), was added. The reaction mixture was stirred at RT for 48 hours and then loaded onto a HiTrap Con A (1 ml) column equilibrated with 20 mM Tris buffer, pH 7.4 (4° C.), containing 0.5 M NaCl, 1 mM $MnCl_2$, 1 mM $CaCl_2$. The protein was eluted over a 0-100% gradient to Buffer X (20 mM Tris buffer, pH 6.4 (4° C.), containing 0.2 M methyl-α-D-mannopyranoside and 0.5 M NaCl). The gpD(S42C::sMannose)-containing fractions were pooled and dialyzed against 50 mM Tris buffer, pH 8, containing 150 mM NaCl, concentrated using an Amicon Ultra-0.5 filter and stored at 4° C. until further use. The expected product was confirmed by mass spectrometry.

Procapsid Expansion. Expanded capsid shells were prepared as previously described in example 1, with modification. Briefly, purified procapsids and a freshly prepared stock of 6 M urea were mixed to afford a reaction mixture (20 µL) containing 40 nM procapsids in 10 mM Tris buffer, pH 8, containing 2.5 M urea and 1 mM $MgCl_2$. The reaction was allowed to proceed for 60 min on ice, and the expanded capsids were then buffer exchanged into TMN buffer (10 mM Tris buffer, pH 8, 1 mM $MgCl_2$) using an Amicon Ultra-0.5 Filter (Millipore).

Decoration of Expanded Capsids with gpD Proteins. Unless otherwise indicated, purified decoration proteins were added to expanded capsids to afford a reaction mixture containing 40 nM capsids and 50 μM decoration protein in TMN buffer. The reaction mixture was incubated at room temperature for 60 min and the capsids analyzed by agarose gel assay (below). When required, unincorporated decoration proteins were removed prior to analysis either by Superose 6 column chromatography or by buffer exchange using an Amicon Ultra 0-0.5 Filter (Millipore). Capsid Decoration Assay. Reaction mixtures were applied to a 1.2% agarose gel, and the capsids fractionated by electrophoresis at 100 V for 180 minutes. The expanded capsid and gpD-decorated capsid bands were visualized by Coomassie brilliant blue stain. Video images of the destained gels were captured using an EpiChemi darkroom system with a Hamamatsu camera (UVP Bioimaging Systems), and quantitation of the bands was performed using the ImageQuant® data analysis package (Molecular Dynamics)

Electron Microscopy. Samples were applied to 300 mesh carbon coated copper grids (Electron Microscopy Sciences) treated by negative glow discharge prior to sample application. Staining was achieved using Nano-W (Nanoprobes) according to manufacturer protocols. Bright field transmission electron microscopy was performed at the NanoTech User Facility at the University of Washington on a FEI Tecnai G2 F20 S-Twin TEM.

Genome Packaging Assay. The genome packaging assay was performed as described in example 1, with modification. Briefly, decorated and expanded capsids at a final concentration of 15 nM were added to a reaction mixture composed of 50 mM Tris buffer, pH 8, containing 1.5 mM NaCl, 10 mM $MgCl_2$, 2 mM spermidine, 0.42 mM β-ME, 1 mM ATP, 50 nM IHF, and 2 mM full-length λ DNA. The packaging reaction (20 μL) was initiated with the addition of terminase to a final concentration of 100 nM and allowed to incubate for 30 minutes at room temperature. DNase I was then added to a final concentration of 10 μg/mL and incubated for 5 minutes before the reaction was stopped with the addition of phenol:chloroform (21 μL). The aqueous layer was removed and loaded onto a 0.8% agarose gel. The DNase-resistant (packaged) DNA was quantified using video densitometry and ImageQuant (Molecular Dynamics) software package.

Agglutination Assay. Decorated capsids (1 μM gpD equivalent) were added to 10 mM HEPES buffered saline solution containing 150 mM NaCl, 1 mM $CaCl_2$ and 1 mM $MgCl_2$. Concanavalin A (ConA, 1 μM) was then added to initiate the reaction and agglutination was detected by monitoring the increase in absorbance (350 nm) at 1-minute intervals. α-D-mannose was added to a final concentration of 5 mM after 20-minutes incubation time to competitively displace the sMannose.

Results

The ability to decorate lambda capsids with modified gpD constructs provides an attractive approach to develop "designer" nanoparticles of defined composition and multipartite, symmetric presentation. Towards this end, we first constructed a plasmid that expresses a HIS-tagged protein composed of an N-terminal gpD domain fused to a C-terminal green fluorescent protein domain (gpD-GFP; FIG. 8B). This protein is analogous to the previously described gpD-EYFP fusion protein used to decorate phage particles in vivo (Alvarez et al., 2006). GpD-GFP can be purified to homogeneity and in high yield.

Figure 9:
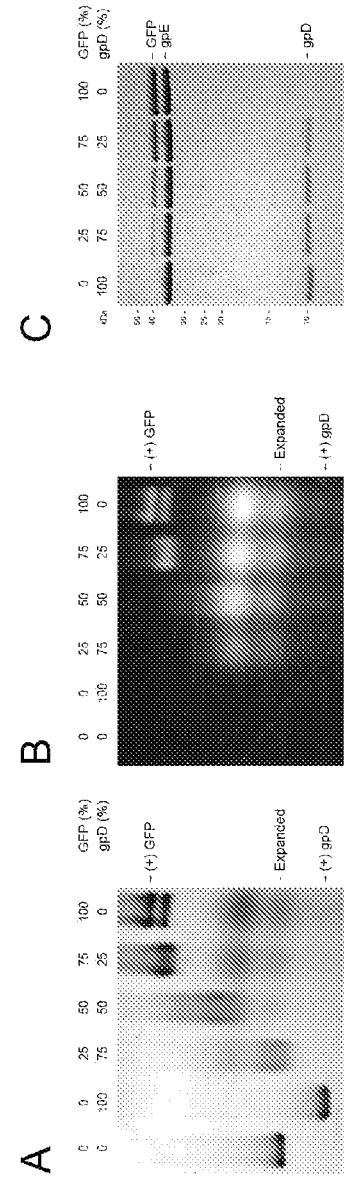
FIG. 9. GFP-Tagged gpD Adds to the Lambda Capsid in Vitro. Expanded capsids were incubated with an increasing ratio of gpD-wt:gpD-GFP as indicated. The decoration mixture was fractionated by agarose gel electrophoresis and the gel was stained with either Coomassie blue (Panel A) or visualized with UV light (Panel B) as described in Materials and Methods. Note that unincorporated H6-gpD-GFP also appears on the agarose gel. Panel C. Unreacted gpD-WT and gpD-GFP was removed from the decoration reaction mixture using Amicon Ultra-0.5 centrifugation filters and the decorated capsids were analyzed by SDS-PAGE.

Decoration of Lambda Capsids with gpD-Green Fluorescent Protein In Vitro. The decoration of expanded lambda capsids with wild-type gpD (gpD-WT) can be conveniently monitored in vitro using an agarose gel assay as described in example 1. Here we utilize this assay to determine whether gpD-GFP can similarly be added to the expanded shell in vitro. In this case, the decorated capsids are visualized in two ways; first by Coomassie blue staining for total protein content (FIG. 9A) and second by fluorescence imaging for the presence of GFP (FIG. 9B). As previously demonstrated, capsids decorated with gpD-WT migrate as a distinct, higher mobility band in the agarose gel. In the presence of increasing amounts of gpD-GFP, progressively slower migrating species appear, consistent with decoration with increasing density of gpD-GFP (FIGS. 9A, 9B). At maximal gpD-GFP densities, two distinct bands are apparent in the gel indicating that two populations are present. Exactly what these two species represent is unclear, but we presume that the upper and lower bands are partially vs. completely decorated capsid shells, respectively.

Figure 7:
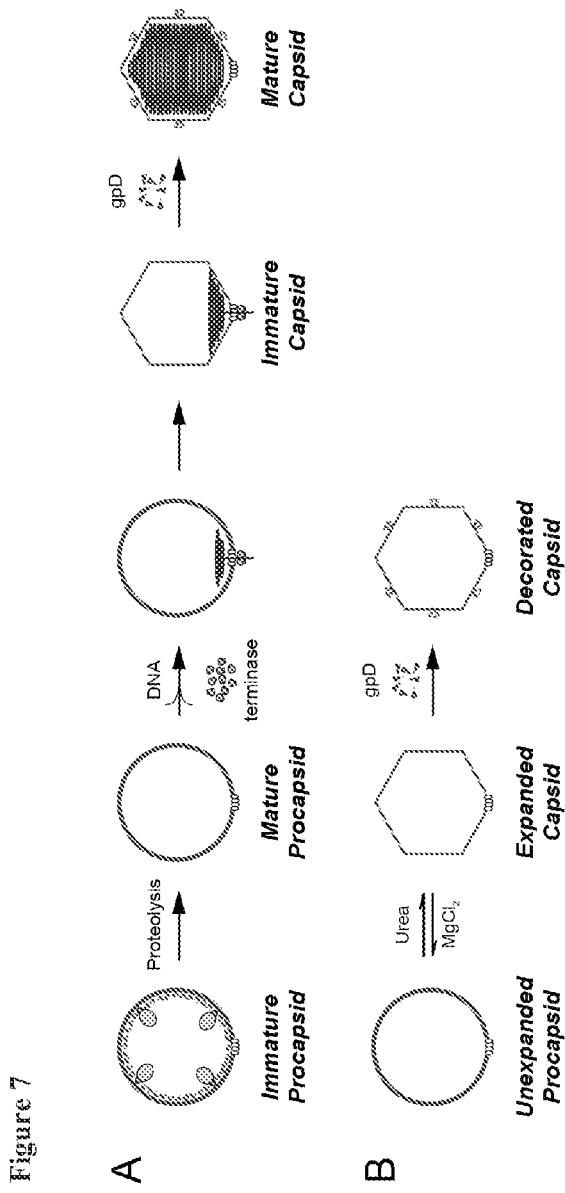
FIG. 7. Bacteriophage lambda capsid in vivo (Panel A) and in vitro (Panel B) assembly. At full saturation, 420 copies of gpD decorate the capsid surface, which is composed of 415 copies of the major capsid protein (gpE). Details described in example 2.

To confirm that the gpD proteins have in fact added to the capsid shell, the capsids were separated from unreacted material using centrifugal filters and the protein content of the decorated shells was examined by SDS-PAGE; the data clearly indicate that both proteins stably add to the capsid (FIG. 9C). Importantly, the surface density of both gpD-WT and gpD-GFP can be tuned by adjusting the ratio of these two proteins included in the reaction mixture. In the presence of gpD-WT alone, the ratio of major capsid protein (gpE) to gpD-WT in the decorated particles is ~1:1, as anticipated for a fully decorated shell capsid (FIG. 7, Table 4). As the amount of gpD-GFP is increased in the reaction mixture, the density of the modified protein on the decorated particles increases to an average surface density of ~77% (FIG. 8C; Table 4). Particle decoration does not appear to be linear, suggesting that gpD-WT outcompetes gpD-GFP for addition to the capsid surface (data not shown). This is not surprising given that the GFP domain (26.9 kDa) adds significant bulk to the small gpD polypeptide (11.4 kDa), which likely interferes with the assembly of the trimeric spikes at the capsid surface (see FIG. 8A).

TABLE 4

Decoration of Lambda Capsids by gpD Variants

| Variant | Surface Density (% relative to gpD) |
| --- | --- |
| gpD-WT | 100 |
| gpD(S42C) | 90 ± 16 |
| gpD(S42C::sMannose) | 82 ± 12 |
| $H_6$-gpD-GFP | 77 ± 14 |

Construction of gpD-Vectors for Diverse Phage Display Applications. The lambda gpD protein has been used in a variety of phage display applications {Beghetto, 2011 #688}. To date, the gpD fusion constructs have appended peptides to either the N-terminus or C-terminus of the protein and decorated phages have been assembled in vivo from the induction of the modified lambda lysogens. While useful, this approach has several limitations. First, display in vivo restricts potential ligands to those that do not affect the development of viable viral particles. It is quite likely that many desired ligands will in fact adversely affect the yield of infectious virus. Second, the current phage display systems require construction of modified lambda genomes and induction of lambda lysogens in vivo to afford the modified particle. This approach is laborious and is ultimately controlled by the whims of the E. coli cell, which does not allow facile manipulation shell decoration density. We reasoned that the in vitro gpD-decoration procedure described above could be adapted for the display of any peptide/protein on the capsid surface and at defined surface densities. Towards this end we constructed a vector that possesses a multi-cloning site immediately downstream from the D gene (gpD-MCS, FIG. 8B), which allows facile expression of C-terminal tagged gpD-fusion proteins that can be used to decorate the lambda capsid in vitro, as described for gpD-GFP above. We also constructed an analogous vector that allows facile generation of N-terminal tagged fusion proteins (MCS-gpD). These vectors allow rapid and efficient expression of gpD-fusion proteins that can be used to decorate the lambda capsid in vitro with total control of surface display density.

A third major limitation to all current phage display platforms including lambda is that the systems are limited to proteinaceous tags. To address this limitation, we next constructed vectors that express gpD containing a unique cysteine residue either at the N-terminus (Cys-gpD-$H_6$) or the C-terminus ($H_6$-gpD-Cys) of the protein (FIG. 8B). The purified proteins provide scaffolds that can be site-specifically modified with a variety of ligands, not limited to peptides, using simple maleimide chemistry. This is discussed further below.

A final limitation of current phage display systems centers on the location of the N- and C-termini of gpD bound to the capsid surface. GpD is a monomer in solution but adds to the 140 three-fold axes of the icosahedral shell as a trimeric spike (FIGS. 7, 8A). The N-terminus of each subunit directly interacts with the capsid shell to provide stabilizing contacts required for shell integrity {Lander, 2008 #351}, while the C-termini exit the gpD trimer spike proximate to the shell surface (FIG. 8A) {Lander, 2008 #351}. In both cases, appending bulky ligands could easily hinder gpD trimer assembly and interfere with its ability to stabilize the DNA-filled shell. Indeed, this was observed with phage decorated with various GFP variants in vivo {Alvarez, 2007 #680; Zeng, 2011 #681; Nicastro et al., 2013} and is consistent with the incomplete decoration observed with gpD-GFP in vitro (see FIG. 9A).

The crystal structure of the gpD trimer spike reveals that Ser42 is positioned at the apex of the spike in all three subunits (FIG. 8A). Modification of this residue would place the desired tag projecting away from the capsid surface and into solution for optimal display, and with minimal insult to gpD spike assembly and shell integrity. We therefore constructed vectors (with and without N-terminal histidine tags) that that express gpD in which Ser42 has been changed to Cys42 ($H_6$-gpD(S42C) and gpD(S42C), respectively; FIG. 8B). Importantly, there are no other cysteine residues in the native protein and this provides a unique site for reaction with maleimide-based tags.

Chemical Synthesis of gpD(S42C::sMannose). Cysteine-modified gpD constructs provide proteins that can be efficiently and specifically modified using maleimide chemistry. To demonstrate the utility of this approach, we synthesized 6'-maleimidohexanamido-polyethyleneglycol mannoside (sMannose) as described in Materials and Methods. This was used to chemically modify gpD(S42C) to afford the gpD(S42C::sMannose) glycoprotein, which was purified to homogeneity.

Figure 10:
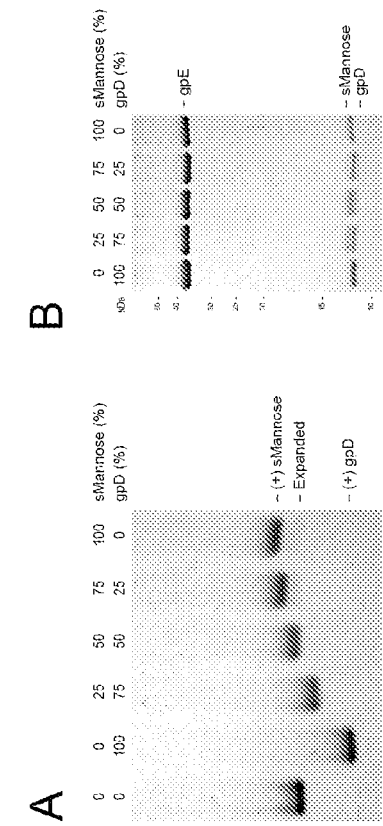
FIG. 10. Expanded capsids can be decorated with varying ratios of gpD and gpD(S42C::sMannose) (sMannose). Panel A. Decorated capsids were separated from excess gpD and sMannose on an agarose gel and stained with Coomassie. Panel B. Decorated capsids were separated from unincorporated gpD and sMannose by buffer exchange using Amicon Ultra-0.5 centrifugation filters and the protein content of the particles were analyzed by SDS-PAGE.

We next examined capsid decoration by gpD(S42C::sMannose). As anticipated, gpD-WT adds to the expanded capsids to afford a unique band of higher mobility in the agarose gel compared to unexpanded (undecorated) procapsids (FIG. 10A). Increasing the fraction of gpD(S42C::sMannose) included in the reaction mixture results in gradual retardation of capsid migration in the gel, consistent with progressive decoration by the gpD glycoprotein. To confirm this presumption, the capsids were separated from unreacted material and the protein content of the decorated capsids analyzed by SDS-PAGE. Unlike gpD-GFP, the density of gpD(S42C::sMannose) on the decorated particles increases in a linear fashion (data not shown) and to a higher average surface density of ~82% (FIG. 10B, Table 4).

Figure 11:
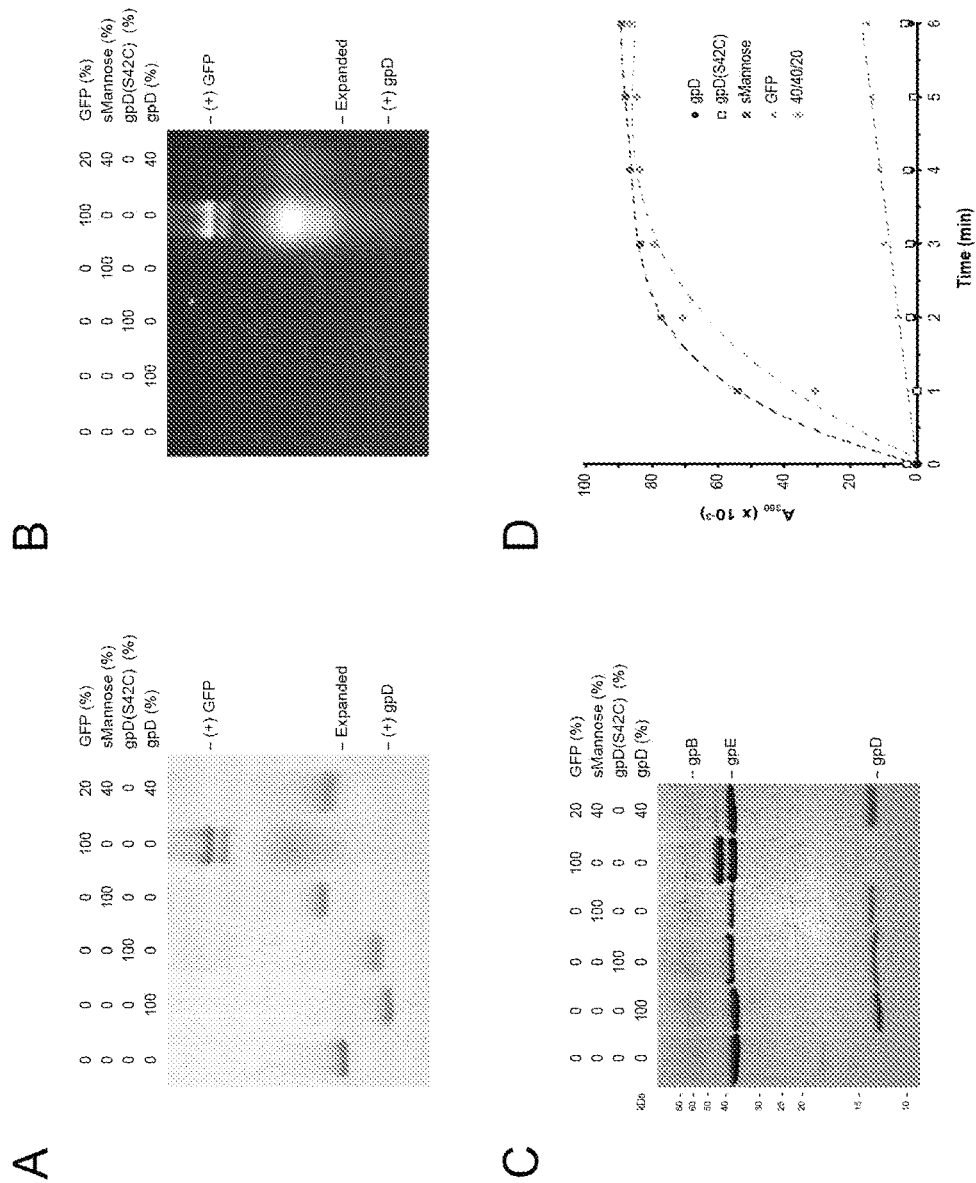
FIG. 11. Lambda Capsids Can be Decorated with Multiple Ligands in a Defined Ratio. Panel A. Expanded capsids can be decorated with varying ratios of gpD(S42C), sMannose, and gpD-GFP. Decorated capsids were separated from excess gpD and modified gpD on an agarose gel and stained with Coomassie. The migration of the decorated capsids on an agarose gel was unique for each variant. Panel C. When illuminated by UV light, GFP-decorated capsids fluoresce. Panel C. Decorated capsids were separated from unincorporated gpD, sMannose and gpD-GFP by buffer exchange using Amicon Ultra-0.5 centrifugation filters and the particles were analyzed by SDS-PAGE. Panel D. To assess the ability of decorated capsids to bind to Concanavalin A (Con A), a mannose-specific lectin, agglutination assays were performed. Only those decorated with sMannose bound specifically to Con A.

The Lambda Capsid can be Decorated with Multiple Tags in a Defined Composition. As demonstrated above, modified gpD constructs can be used to decorate the lambda capsid with a large protein (GFP) and with a mannose glycoprotein. Here we demonstrate that the shell can be decorated with multiple ligands simultaneously. Lambda capsids were incubated with gpD-WT, gpD(S42C::sMannose), and gpD-GFP alone or in combination. The reaction mixture was analyzed by agarose gel assay, which clearly demonstrates that the proteins, alone and in combination, add to the capsid shell to afford decorated particles with a unique mobility in the gel (FIGS. 11A, 11B). Analysis of the isolated, decorated shells by SDS-PAGE demonstrates that (i) each construct efficiently adds to the shell and that (ii) all three proteins can add to the capsid when simultaneously present in the reaction mixture (FIG. 11C). Within this context, we note that gpD-WT and the gpD(S42C::sMannose) glycoprotein migrate closely in SDS-PAGE. In order to confirm the presence of both proteins on the decorated capsid surface, we utilized an agglutination assay. In this assay, the presence of mannose is detected by agglutination of the particles by with Concanavalin (ConA). As expected, neither gpD-WT nor gpD-S42C decorated capsids exhibit a positive agglutination response, while gpD-GFP decorated capsids exhibit a weak (non-specific) agglutination response (FIG. 5D). In contrast, capsids decorated with gpD(S42C::sMannose) show a strong response indicating (i) mannose is present on the capsid surface and (ii) it is efficiently displayed for interaction with ConA.

Figure 12:
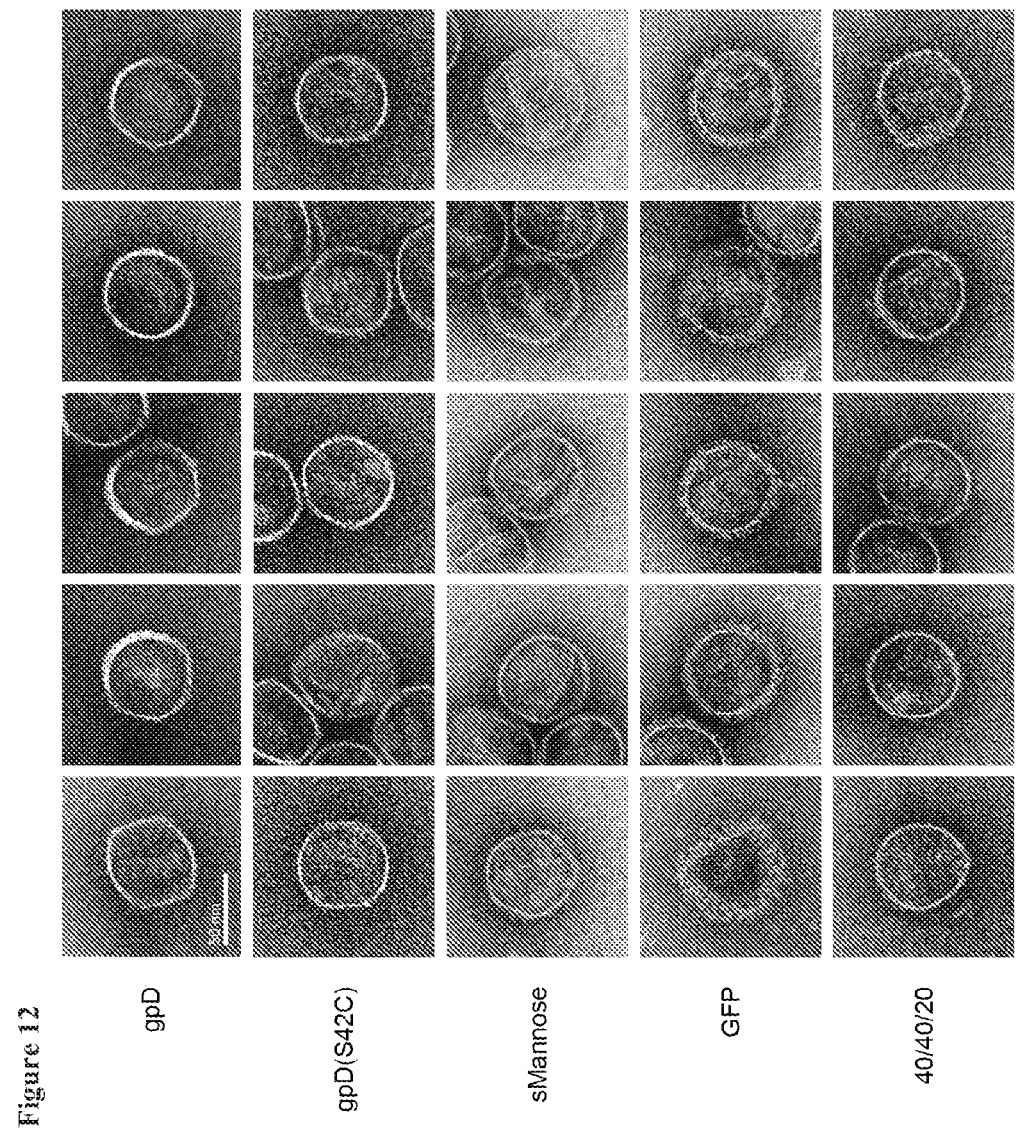
FIG. 12. Electron micrographs of decorated capsids. Details described in example 2. Scale bar, 50 nm.
Figure 13:
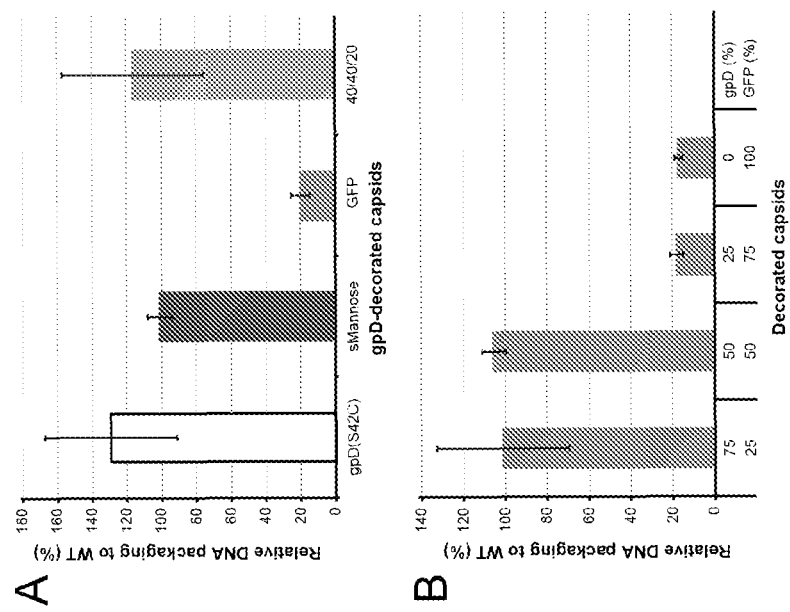
FIG. 13. Capsids decorated with modified gpD retain DNA packaging activity. Panel A. Capsids fully decorated with sMannose are fully competent, but those decorated with 100% gpD-GFP are compromised when full-length lambda is used as the packaging substrate. Panel B. Capsids decorated with up to 50% gpD-GFP are fully competent for packaging.

Structural Characterization of the Decorated Lambda Capsids. A major advantage of utilizing viral capsids as display platforms is that under ideal conditions they can display the tags in a symmetric and defined manner. In the case of the gpD constructs discussed here, tags of known composition can be appended to the display protein in a site-specific manner, which can then be presented as trimers at the three-fold icosahedral axes of the capsid shell. While it is clear that our modified gpD constructs efficiently bind to the lambda capsid, confirmation that the shells remain intact for optimal display of the tags is important. We therefore utilized electron microscopy to examine the decorated shells as described in Materials and Methods. Capsids decorated with gpD-WT are composed of an intact icosahedral shell with thinned walls and significant angular facets (FIG. 12), as observed with an infectious lambda virus {Dokland, 1993 #414; Lander, 2008 #351}. The gpD(S42C) decorated capsids are similar in morphology, consistent with the conservative mutation in the protein and their near-native gel migration in the agarose gel (FIG. 11A). Capsids decorated with the gpD(S42C::sMannose) glycoprotein similarly display a thin and angularized shell, though perhaps not as faceted as wild-type decorated shells (FIG. 12). The gpD-GFP decorated shells also possess the thin wall phenotype and similarly appear less faceted than wild type. In addition, the shells have an extra density on the exterior shell surface, which we presume reflects the presence of the large GFP domain appended to the capsid surface (FIG. 12). Decorated capsids isolated from reaction mixtures containing gpD-WT, gpD(S42C::sMannose), and gpD-GFP in a 40:40:20 ratio also possess extra staining density at the capsid shell, though not as prominent as those fully-decorated with gpD-GFP; this is consistent with the lower surface density of gpD-GFP on these particles (FIG. 11A).

Functional Characterization of the Decorated Lambda Capsids. Procapsids serve as receptacles for the viral genome, and gpD is required to provide structural integrity to the DNA-filled shell (FIG. 7) {Yang, 2008 #}. In the absence of gpD, the capsid cannot withstand the intense pressures generated by the packaged DNA (>50 atmospheres) and the shell fractures, rendering the DNA accessible to DNase digestion {Yang, 2008 #1}. Here we utilize an in vitro DNA packaging assay to determine if capsids decorated with modified gpD proteins are functionally active in capsid shell stabilization.

The genome packaging reaction was performed as described in Materials and Methods using capsids decorated with either gpD-WT, gpD(S42C), gpD(S42C::sMannose), or gpD-GFP. As shown in FIG. 7A, gpD(S42C) and the gpD(S42C::sMannose) glycoprotein are as efficient as wild-type gpD in the DNA packaging reaction. In contrast, capsids decorated with $H_6$-gpD-GFP are seriously compromised when the surface density of the protein exceeds 50% (FIG. 7B). Thus, while the GFP-modified protein can fully decorate the expanded shell (Table 4), it does not necessarily impart the requisite structural integrity required to retain a fully-packaged genome. This is consistent with the observation that infectious lambda virus decorated with gpD-GFP variants are less stable compared to wild-type virus in vivo (Alvarez et al., 2006, Nicastro et al., 2013).

Discussion

Decoration of the lambda capsid is a powerful tool in the development of nanoparticles for theragnostic applications. Its relative ease aids in the modification of the capsid, allowing the display of tags in a defined and tunable manner. We have developed an in vitro decoration system in which lambda capsids are decorated with non-proteinaceous ligand conjugated to gpD. Validation of the system was first confirmed using the modified gpD fusion protein, gpD-GFP.

Lambda capsids can be decorated in vitro with gpD-GFP. Characterization of the gpD-GFP in vitro decorated capsids is consistent with the gpD-EYFP and gpD-GFP in vivo decorated viruses (Alvarez et al., 2008; Nicastro et al., 2013). The added bulk of GFP affects the stability of both the in vivo and in vivo decorated capsids. Because the C-terminus of gpD lies near the capsid surface (Chang et al., 2004; Lander et al., 2008), gpD-GFP may interfere with the addition of the gpD trimers to the capsid surface, hence, the two distinct populations of gpD-GFP decorated capsids visualized by agarose gel analysis when only gpD-GFP is present. Representation of the gpD-GFP decorated capsids on SDS-PAGE is an average of the two populations. The exact coverage for each population is unknown, but we surmise that one population has a higher surface density than the other. Despite this, gpD-GFP is ineffective in stabilizing capsids to the same extent as the other gpD variants. The added bulk of GFP to the C-terminus of gpD most likely interferes with the ability of gpD to stabilize the capsid. The apical gpD residue 42 is an ideal candidate for conjugation.

The advent of gpD(S42C) (and similar gpD functional mutants) and the capacity of the system to be tunable circumvents the issues of capsid stability. Modification of the apical residue S42C does not decrease capsid stability to the same extent as modifications to either the N- or C-termini of gpD Addition of gpD(S42C::sMannose) to the capsid, although not as complete as gpD-WT, does provide sufficient capsid stability. This suggests that full coverage of the capsid shell by gpD may not be a strict requirement for packing competency. About 80% coverage appears to be the minimum required assuming that the modification tag does not interfere with structural stability of the capsid, as the case with gpD-GFP but not gpD(S42C::sMannose). Added bulk to the structurally compact gpD-WT at the apical residue 42 may lower efficiency of trimer formation depending on the size of the conjugant. This may be avoided with the initial addition of gpD-WT at a partial complement. Although how the gpD variants are participating in trimer formation is unclear, gpD-WT stabilizes the capsid structure by limiting the saturation of the modified gpD variant and its potential hazard of capsid instability either within in each trimer or between trimers.

The range of capsid decoration is limited by the initial concentrations of the gpD variants thereby allowing tunability. Capsids decorated with gpD-WT and gpD-GFP appear as diffuse bands on agarose gels compared to capsids decorated with a single variant (FIGS. 9A, 11A), suggesting that the gpD-WT is masking the partiality of gpD-GFP. Capsids decorated with gpD-WT and gpD(S42C::sMannose) appear as discrete bands with increasing concentrations of gpD (S42C::sMannose) (FIG. 10A). Although the size disparity between the two variants is minimal by comparison, the structural difference between gpD-WT and gpD(S42C::sMannose) is at an apical residue, not at a region involved in capsid stability like gpD-GFP. Decoration of the capsid by gpD(S42C::sMannose) is most likely more homogenous compared to that by gpD-GFP. Capsids decorated with all three gpD variants appear as a diffuse band on agarose gel (FIG. 11A), implicating gpD-GFP as the factor causing heterogeneity in capsid decoration. Because gpD-GFP is initially limited, its role in decoration is depressed but not suppressed. Our system's tunability is advantageous, allowing the inclusion of proteinaceous and non-proteinaceous ligands that would otherwise be disadvantageous to capsid stability.

One potential downstream application of the in vitro decorated capsids would be their involvement in vitro assembled viruses. We have previously developed an assay for assembling via lambda viruses in vitro (Gaussier et al., 2006). Genetically modified DNA can be packaged into in vitro decorated capsids. The attachment of tails to the mature capsid prevents exit of the packaged DNA as well as produces a carrier for DNA which can be targeted to a specific cell type, for example, via a non-proteinaceous modification conjugated to gpD. We have utilized our in vitro capsid assembly system to decorate lambda capsids with proteinaceous and non-proteinaceous modification. The ability to tune the decoration of lambda capsids in vitro obviates possible capsid instability of bulky modifications but not limiting what can be added to the capsid surface. This expands the utility of the capsid display system.

REFERENCES FOR EXAMPLE 2

1. Alvarez, L. J., Thomen, P., Makushok, T., and Chatenay, D. (2007) Propagation of Fluorescent Viruses in Growing Plaques., *Biotechnol. Bioeng.* 96, 615-621.
2. Nicastro, J., Sheldon, K., El-zarkout, F. A., Sokolenko, S., Aucoin, M. G., and Slavcev, R. (2013) Construction and Analysis of a Genetically Tuneable Lytic Phage Display System, *App. Microbiol. Biotechnol.*
3. Yang, Q., and Catalano, C. E. (2003) Biochemical characterization of bacteriophage lambda genome packaging in vitro, *Virology* 305, 276-287.

4. Gaussier, H., Yang, Q., and Catalano, C. E. (2006) Building a virus from scratch: assembly of an infectious virus using purified components in a rigorously defined biochemical assay system, *J Mol Biol* 357, 1154-1166.
5. Medina, E., Nakatani, E., Kruse, S., and Catalano, C. E. (2012) Thermodynamic Characterization of Viral Procapsid Expansion into a Functional Capsid Shell, *J. Mol. Biol*. 418, 167-180.
6. Beghetto, E., and Gargano, N. (2011) Lambda Display: A Powerful Tool for Antigen Discovery, *Molecules* 16, 3089-3105.
7. Lander, G. C., Evilevitch, A., Jeembaeva, M., Potter, C. S., Carragher, B., and Johnson, J. E. (2008) Bacteriophage Lambda Stabilization by Auxiliary Protein gpD: Timing, Location, and Mechanism of Attachment Determined by Cryo-EM, *Structure* 16, 1399-1406.
8. Zeng. L., and Golding, I. (2011) Following Cell-fate in *E. coli* After Infection by Phage Lambda, *Journal of Visualized Experiments* 56, 3363.
9. Dokland, T., and Murialdo, H. (1993) Structural Transitions During Maturation of Bacteriophage Lambda Capsids, *J. Mol. Biol*. 233, 682-694.
10. Yang, Q., Maluf, N. K., and Catalano, C. E. (2008) Packaging of a Unit-Length Viral Genome: The Role of Nucleotides and the gpD Decoration Protein in Stable Nucleocapsid Assembly in Bacteriophage Lambda, *Journal of Molecular Biology* 383, 1037-1048.

We claim:

1. A theragnostic particle, comprising a plurality of engineered decoration proteins bound to an outer surface of decoration competent viral particle shell, wherein the engineered decoration proteins comprise gpDS42C (SEQ ID NO: 10) linked to one or more compounds not naturally occurring on a wild type viral capsid, and wherein the one or more compounds have at least one feature selected from the group consisting of:
   (a) the one or more compounds are non-proteinaceous compounds;
   (b) the one or more compounds are present on the theragnostic particle in a defined ratio relative to the engineered decoration protein;
   (c) the one or more compounds comprise two or more different compounds, wherein the two or more different compounds are present on the theragnostic particle in a defined ratio relative to each other; and
   (d) the one or more compounds are linked to the engineered decoration protein at a site on the engineered decoration protein other than the N-terminus or the C-terminus, wherein the decoration competent viral particle shell comprises a bacteriophage lambda viral particle shell.

2. The theragnostic particle of claim 1, wherein the one or more compounds are non-proteinaceous compounds.

3. The theragnostic particle of claim 1 wherein the one or more compounds are present on the theragnostic particle in a defined ratio relative to the engineered decoration protein.

4. The theragnostic particle of claim 1, wherein the one or more compounds comprise two or more different compounds, wherein the two or more different compounds are present on the theragnostic particle in a defined ratio relative to each other.

5. The theragnostic particle of claim 1, wherein the one or more compounds are linked to the engineered decoration protein at a site on the engineered decoration protein other than the N-terminus or the C-terminus.

6. The theragnostic particle of claim 1, wherein the engineered decoration proteins comprise engineered decoration proteins linked to one or more compounds that have at least one feature selected from the group consisting of (b), (c), and (d) according to claim 1, wherein the compounds are selected from the group consisting of nucleic acids, lipids, carbohydrates, polypeptides, polymers, organic molecules, inorganic molecules, and combinations thereof.

7. The theragnostic particle of claim 1, wherein the engineered decoration proteins comprise engineered decoration proteins linked to one or more non-proteinaceous compounds selected from the group consisting of nucleic acids, lipids, carbohydrates, polymers, organic molecules, inorganic, and combinations thereof.

8. The theragnostic particle of claim 1, wherein the one or more compounds have at least one feature selected from the group consisting of (b), (c), and (d) according to claim 1, and wherein the compounds are selected from the group consisting of therapeutic compounds, diagnostic compounds, adjuvants, antigens, antibodies, and combinations thereof.

9. The theragnostic particle of claim 1, wherein the one or more compounds linked to the decoration proteins comprise two or more different compounds.

10. The theragnostic particle of claim 1, wherein the bacteriophage lambda particle shell is an expanded bacteriophage lambda particle shell.

11. A pharmaceutical composition, comprising:
    (a) the theragnostic particle of claim 1; and
    (b) a pharmaceutically acceptable carrier.

12. An isolated recombinant protein comprising the amino acid sequence of SEQ ID NO: 10 (gpD(S42C)).

13. The isolated recombinant protein of claim 12, further comprising one or more compounds linked to the recombinant protein via the cysteine at position 42.

14. An isolated nucleic acid encoding the recombinant protein of claim 12.

15. A recombinant expression vector comprising the isolated nucleic acid of claim 14.

16. The theragnostic particle of claim 1, wherein the one or more compounds comprise mannose.

17. The theragnostic particle of claim 1, wherein the one or more compounds are non-proteinaceous compounds, and wherein the one or more compounds are selected from the group consisting of therapeutic compounds, diagnostic compounds, adjuvants, and combinations thereof.

* * * * *

```
SEQUENCE LISTING

<160> NUMBER OF SEQ ID NOS: 36

<210> SEQ ID NO 1
<211> LENGTH: 533
<212> TYPE: PRT
<213> ORGANISM: enterobacteria phage lambda

<400> SEQUENCE: 1

Met Lys Thr Pro Thr Ile Pro Thr Leu Leu Gly Pro Asp Gly Met Thr
1               5                   10                  15

Ser Leu Arg Glu Tyr Ala Gly Tyr His Gly Gly Ser Gly Phe Gly
            20                  25                  30

Gly Gln Leu Arg Ser Trp Asn Pro Pro Ser Glu Ser Val Asp Ala Ala
        35                  40                  45

Leu Leu Pro Asn Phe Thr Arg Gly Asn Ala Arg Ala Asp Asp Leu Val
    50                  55                  60

Arg Asn Asn Gly Tyr Ala Ala Asn Ala Ile Gln Leu His Gln Asp His
65                  70                  75                  80

Ile Val Gly Ser Phe Phe Arg Leu Ser His Arg Pro Ser Trp Arg Tyr
                85                  90                  95

Leu Gly Ile Gly Glu Glu Glu Ala Arg Ala Phe Ser Arg Glu Val Glu
            100                 105                 110

Ala Ala Trp Lys Glu Phe Ala Glu Asp Cys Cys Cys Ile Asp Val
        115                 120                 125

Glu Arg Lys Arg Thr Phe Thr Met Met Ile Arg Glu Gly Val Ala Met
130                 135                 140

His Ala Phe Asn Gly Glu Leu Phe Val Gln Ala Thr Trp Asp Thr Ser
145                 150                 155                 160

Ser Ser Arg Leu Phe Arg Thr Gln Phe Arg Met Val Ser Pro Lys Arg
                165                 170                 175

Ile Ser Asn Pro Asn Asn Thr Gly Asp Ser Arg Asn Cys Arg Ala Gly
            180                 185                 190

Val Gln Ile Asn Asp Ser Gly Ala Ala Leu Gly Tyr Tyr Val Ser Glu
        195                 200                 205

Asp Gly Tyr Pro Gly Trp Met Pro Gln Lys Trp Thr Trp Ile Pro Arg
    210                 215                 220

Glu Leu Pro Gly Gly Arg Ala Ser Phe Ile His Val Phe Glu Pro Val
225                 230                 235                 240

Glu Asp Gly Gln Thr Arg Gly Ala Asn Val Phe Tyr Ser Val Met Glu
                245                 250                 255

Gln Met Lys Met Leu Asp Thr Leu Gln Asn Thr Gln Leu Gln Ser Ala
            260                 265                 270
```

```
Ile Val Lys Ala Met Tyr Ala Ala Thr Ile Glu Ser Glu Leu Asp Thr
            275                 280                 285

Gln Ser Ala Met Asp Phe Ile Leu Gly Ala Asn Ser Gln Glu Gln Arg
        290                 295                 300

Glu Arg Leu Thr Gly Trp Ile Gly Glu Ile Ala Ala Tyr Tyr Ala Ala
305                 310                 315                 320

Ala Pro Val Arg Leu Gly Ala Lys Val Pro His Leu Met Pro Gly
                325                 330                 335

Asp Ser Leu Asn Leu Gln Thr Ala Gln Asp Thr Asp Asn Gly Tyr Ser
            340                 345                 350

Val Phe Glu Gln Ser Leu Leu Arg Tyr Ile Ala Ala Gly Leu Gly Val
        355                 360                 365

Ser Tyr Glu Gln Leu Ser Arg Asn Tyr Ala Gln Met Ser Tyr Ser Thr
    370                 375                 380

Ala Arg Ala Ser Ala Asn Glu Ser Trp Ala Tyr Phe Met Gly Arg Arg
385                 390                 395                 400

Lys Phe Val Ala Ser Arg Gln Ala Ser Gln Met Phe Leu Cys Trp Leu
                405                 410                 415

Glu Glu Ala Ile Val Arg Arg Val Val Thr Leu Pro Ser Lys Ala Arg
            420                 425                 430

Phe Ser Phe Gln Glu Ala Arg Ser Ala Trp Gly Asn Cys Asp Trp Ile
        435                 440                 445

Gly Ser Gly Arg Met Ala Ile Asp Gly Leu Lys Glu Val Gln Glu Ala
450                 455                 460

Val Met Leu Ile Glu Ala Gly Leu Ser Thr Tyr Glu Lys Glu Cys Ala
465                 470                 475                 480

Lys Arg Gly Asp Asp Tyr Gln Glu Ile Phe Ala Gln Val Arg Glu
                485                 490                 495

Thr Met Glu Arg Arg Ala Ala Gly Leu Lys Pro Pro Ala Trp Ala Ala
            500                 505                 510

Ala Ala Phe Glu Ser Gly Leu Arg Gln Ser Thr Glu Glu Lys Ser
        515                 520                 525

Asp Ser Arg Ala Ala
    530

<210> SEQ ID NO 2
<211> LENGTH: 341
<212> TYPE: PRT
<213> ORGANISM: enterobacteria phage lambda

<400> SEQUENCE: 2

Met Ser Met Tyr Thr Thr Ala Gln Leu Leu Ala Ala Asn Glu Gln Lys
1               5                   10                  15

Phe Lys Phe Asp Pro Leu Phe Leu Arg Leu Phe Phe Arg Glu Ser Tyr
                20                  25                  30

Pro Phe Thr Thr Glu Lys Val Tyr Leu Ser Gln Ile Pro Gly Leu Val
            35                  40                  45

Asn Met Ala Leu Tyr Val Ser Pro Ile Val Ser Gly Glu Val Ile Arg
        50                  55                  60

Ser Arg Gly Gly Ser Thr Ser Glu Phe Thr Pro Gly Tyr Val Lys Pro
65                  70                  75                  80

Lys His Glu Val Asn Pro Gln Met Thr Leu Arg Arg Leu Pro Asp Glu
                85                  90                  95

Asp Pro Gln Asn Leu Ala Asp Pro Ala Tyr Arg Arg Arg Ile Ile
                100                 105                 110
```

```
Met Gln Asn Met Arg Asp Glu Glu Leu Ala Ile Ala Gln Val Glu
            115                 120                 125
Met Gln Ala Val Ser Ala Val Leu Lys Gly Lys Tyr Thr Met Thr Gly
130                 135                 140
Glu Ala Phe Asp Pro Val Glu Val Asp Met Gly Arg Ser Glu Asn
145                 150                 155                 160
Asn Ile Thr Gln Ser Gly Gly Thr Glu Trp Ser Lys Arg Asp Lys Ser
                165                 170                 175
Thr Tyr Asp Pro Thr Asp Ile Glu Ala Tyr Ala Leu Asn Ala Ser
                180                 185                 190
Gly Val Val Asn Ile Ile Val Phe Asp Pro Lys Gly Trp Ala Leu Phe
                195                 200                 205
Arg Ser Phe Lys Ala Val Lys Glu Lys Leu Asp Thr Arg Arg Gly Ser
                210                 215                 220
Asn Ser Glu Leu Glu Thr Ala Val Lys Asp Leu Gly Lys Ala Val Ser
225                 230                 235                 240
Tyr Lys Gly Met Tyr Gly Asp Val Ala Ile Val Val Tyr Ser Gly Gln
                245                 250                 255
Tyr Val Glu Asn Gly Val Lys Lys Asn Phe Leu Pro Asn Thr Met
                260                 265                 270
Val Leu Gly Asn Thr Gln Ala Arg Gly Leu Arg Thr Tyr Gly Cys Ile
                275                 280                 285
Gln Asp Ala Asp Ala Gln Arg Glu Gly Ile Asn Ala Ser Ala Arg Tyr
                290                 295                 300
Pro Lys Asn Trp Val Thr Thr Gly Asp Pro Ala Arg Glu Phe Thr Met
305                 310                 315                 320
Ile Gln Ser Ala Pro Leu Met Leu Leu Ala Asp Pro Asp Glu Phe Val
                325                 330                 335
Ser Val Gln Leu Ala
            340

<210> SEQ ID NO 3
<211> LENGTH: 439
<212> TYPE: PRT
<213> ORGANISM: enterobacteria phage lambda

<400> SEQUENCE: 3

Met Thr Ala Glu Leu Arg Asn Leu Pro His Ile Ala Ser Met Ala Phe
1               5                   10                  15
Asn Glu Pro Leu Met Leu Glu Pro Ala Tyr Ala Arg Val Phe Phe Cys
                20                  25                  30
Ala Leu Ala Gly Gln Leu Gly Ile Ser Ser Leu Thr Asp Ala Val Ser
            35                  40                  45
Gly Asp Ser Leu Thr Ala Gln Glu Ala Leu Ala Thr Leu Ala Leu Ser
        50                  55                  60
Gly Asp Asp Gly Pro Arg Gln Ala Arg Ser Tyr Gln Val Met Asn
65                  70                  75                  80
Gly Ile Ala Val Leu Pro Val Ser Gly Thr Leu Val Ser Arg Thr Arg
                85                  90                  95
Ala Leu Gln Pro Tyr Ser Gly Met Thr Gly Tyr Asn Gly Ile Ile Ala
                100                 105                 110
Arg Leu Gln Gln Ala Ala Ser Asp Pro Met Val Asp Gly Ile Leu Leu
            115                 120                 125
Asp Met Asp Thr Pro Gly Gly Met Val Ala Gly Ala Phe Asp Cys Ala
```

```
            130                 135                 140
Asp Ile Ile Ala Arg Val Arg Asp Ile Lys Pro Val Trp Ala Leu Ala
145                 150                 155                 160

Asn Asp Met Asn Cys Ser Ala Gly Gln Leu Leu Ala Ser Ala Ala Ser
                165                 170                 175

Arg Arg Leu Val Thr Gln Thr Ala Arg Thr Gly Ser Ile Gly Val Met
            180                 185                 190

Met Ala His Ser Asn Tyr Gly Ala Ala Leu Glu Lys Gln Gly Val Glu
        195                 200                 205

Ile Thr Leu Ile Tyr Ser Gly Ser His Lys Val Asp Gly Asn Pro Tyr
210                 215                 220

Ser His Leu Pro Asp Asp Val Arg Glu Thr Leu Gln Ser Arg Met Asp
225                 230                 235                 240

Ala Thr Arg Gln Met Phe Ala Gln Lys Val Ser Ala Tyr Thr Gly Leu
                245                 250                 255

Ser Val Gln Val Val Leu Asp Thr Glu Ala Ala Val Tyr Ser Gly Gln
            260                 265                 270

Glu Ala Ile Asp Ala Gly Leu Ala Asp Glu Leu Val Asn Ser Thr Asp
        275                 280                 285

Ala Ile Thr Val Met Arg Asp Ala Leu Asp Ala Arg Lys Ser Arg Leu
290                 295                 300

Ser Gly Gly Arg Met Thr Lys Glu Thr Gln Ser Thr Thr Val Ser Ala
305                 310                 315                 320

Thr Ala Ser Gln Ala Asp Val Thr Asp Val Val Pro Ala Thr Glu Gly
                325                 330                 335

Glu Asn Ala Ser Ala Ala Gln Pro Asp Val Asn Ala Gln Ile Thr Ala
            340                 345                 350

Ala Val Ala Ala Glu Asn Ser Arg Ile Met Gly Ile Leu Asn Cys Glu
        355                 360                 365

Glu Ala His Gly Arg Glu Glu Gln Ala Arg Val Leu Ala Glu Thr Pro
370                 375                 380

Gly Met Thr Val Lys Thr Ala Arg Arg Ile Leu Ala Ala Pro Gln
385                 390                 395                 400

Ser Ala Gln Ala Arg Ser Asp Thr Ala Leu Asp Arg Leu Met Gln Gly
                405                 410                 415

Ala Pro Ala Pro Leu Ala Ala Gly Asn Pro Ala Ser Asp Ala Val Asn
            420                 425                 430

Asp Leu Leu Asn Thr Pro Val
        435

<210> SEQ ID NO 4
<211> LENGTH: 110
<212> TYPE: PRT
<213> ORGANISM: Enterobacteria phage lambda
<220> FEATURE:
<221> NAME/KEY: MISC_FEATURE
<222> LOCATION: (1)..(1)
<223> OTHER INFORMATION: Met is optionally absent

<400> SEQUENCE: 4

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45
```

-continued

Ala Trp Asp Gly Thr Thr Asp Gly Ala Ala Val Gly Ile Leu Ala Val
            50                  55                  60

Ala Ala Asp Gln Thr Ser Thr Thr Leu Thr Phe Tyr Lys Ser Gly Thr
 65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val
            100                 105                 110

<210> SEQ ID NO 5
<211> LENGTH: 376
<212> TYPE: PRT
<213> ORGANISM: Enterobacteria phage T4

<400> SEQUENCE: 5

Met Thr Phe Thr Val Asp Ile Thr Pro Lys Thr Pro Thr Gly Val Ile
 1               5                  10                  15

Asp Glu Thr Lys Gln Phe Thr Ala Thr Pro Ser Gly Gln Thr Gly Gly
                20                  25                  30

Gly Thr Ile Thr Tyr Ala Trp Ser Val Asp Asn Val Pro Gln Asp Gly
            35                  40                  45

Ala Glu Ala Thr Phe Ser Tyr Val Leu Lys Gly Pro Ala Gly Gln Lys
 50                  55                  60

Thr Ile Lys Val Val Ala Thr Asn Thr Leu Ser Glu Gly Gly Pro Glu
 65                  70                  75                  80

Thr Ala Glu Ala Thr Thr Thr Ile Thr Val Lys Asn Lys Thr Gln Thr
                85                  90                  95

Thr Thr Leu Ala Val Thr Pro Ala Ser Pro Ala Ala Gly Val Ile Gly
            100                 105                 110

Thr Pro Val Gln Phe Thr Ala Ala Leu Ala Ser Gln Pro Asp Gly Ala
            115                 120                 125

Ser Ala Thr Tyr Gln Trp Tyr Val Asp Asp Ser Gln Val Gly Gly Glu
            130                 135                 140

Thr Asn Ser Thr Phe Ser Tyr Thr Pro Thr Thr Ser Gly Val Lys Arg
145                 150                 155                 160

Ile Lys Cys Val Ala Gln Val Thr Ala Thr Asp Tyr Asp Ala Leu Ser
                165                 170                 175

Val Thr Ser Asn Glu Val Ser Leu Thr Val Asn Lys Lys Thr Met Asn
            180                 185                 190

Pro Gln Val Thr Leu Thr Pro Pro Ser Ile Asn Val Gln Gln Asp Ala
            195                 200                 205

Ser Ala Thr Phe Thr Ala Asn Val Thr Gly Ala Pro Glu Glu Ala Gln
            210                 215                 220

Ile Thr Tyr Ser Trp Lys Lys Asp Ser Ser Pro Val Glu Gly Ser Thr
225                 230                 235                 240

Asn Val Tyr Thr Val Asp Thr Ser Ser Val Gly Ser Gln Thr Ile Glu
                245                 250                 255

Val Thr Ala Thr Val Thr Ala Ala Asp Tyr Asn Pro Val Thr Val Thr
            260                 265                 270

Lys Thr Gly Asn Val Thr Val Thr Ala Lys Val Ala Pro Glu Pro Glu
            275                 280                 285

Gly Glu Leu Pro Tyr Val His Pro Leu Pro His Arg Ser Ser Ala Tyr
            290                 295                 300

Ile Trp Cys Gly Trp Trp Val Met Asp Glu Ile Gln Lys Met Thr Glu

```
                305                 310                 315                 320
Glu Gly Lys Asp Trp Lys Thr Asp Asp Pro Asp Ser Lys Tyr Tyr Leu
                325                 330                 335

His Arg Tyr Thr Leu Gln Lys Met Met Lys Asp Tyr Pro Glu Val Asp
                340                 345                 350

Val Gln Glu Ser Arg Asn Gly Tyr Ile Ile His Lys Thr Ala Leu Glu
                355                 360                 365

Thr Gly Ile Ile Tyr Thr Tyr Pro
        370                 375

<210> SEQ ID NO 6
<211> LENGTH: 80
<212> TYPE: PRT
<213> ORGANISM: Enterobacteria phage T4

<400> SEQUENCE: 6

Met Ala Ser Thr Arg Gly Tyr Val Asn Ile Lys Thr Phe Glu Gln Lys
1               5                   10                  15

Leu Asp Gly Asn Lys Lys Ile Glu Gly Lys Glu Ile Ser Val Ala Phe
                20                  25                  30

Pro Leu Tyr Ser Asp Val His Lys Ile Ser Gly Ala His Tyr Gln Thr
            35                  40                  45

Phe Pro Ser Glu Lys Ala Ala Tyr Ser Thr Val Tyr Glu Glu Asn Gln
        50                  55                  60

Arg Thr Glu Trp Ile Ala Ala Asn Glu Asp Leu Trp Lys Val Thr Gly
65                  70                  75                  80

<210> SEQ ID NO 7
<211> LENGTH: 115
<212> TYPE: PRT
<213> ORGANISM: Enterobacteria phage P21

<400> SEQUENCE: 7

Met Val Thr Lys Thr Ile Thr Glu Gln Arg Ala Glu Val Arg Ile Phe
1               5                   10                  15

Ala Gly Asn Asp Pro Ala His Thr Ala Thr Gly Ser Ser Gly Ile Ser
                20                  25                  30

Ser Pro Thr Pro Ala Leu Thr Pro Leu Met Leu Asp Glu Ala Thr Gly
            35                  40                  45

Lys Leu Val Val Trp Asp Gly Gln Lys Ala Gly Ser Ala Val Gly Ile
        50                  55                  60

Leu Val Leu Pro Leu Glu Gly Thr Glu Thr Ala Leu Thr Tyr Tyr Lys
65                  70                  75                  80

Ser Gly Thr Phe Ala Thr Glu Ala Ile His Trp Pro Glu Ser Val Asp
                85                  90                  95

Glu His Lys Lys Ala Asn Ala Phe Ala Gly Ser Ala Leu Ser His Ala
                100                 105                 110

Ala Leu Pro
        115

<210> SEQ ID NO 8
<211> LENGTH: 134
<212> TYPE: PRT
<213> ORGANISM: Enterobacteria phage L

<400> SEQUENCE: 8

Met Ala Asn Pro Asn Phe Thr Pro Ser Trp Pro Leu Tyr Lys Asp Ala
1               5                   10                  15
```

Asp Gly Val Tyr Val Ser Ala Leu Pro Ile Lys Ala Ile Lys Tyr Ala
            20                  25                  30

Asn Asp Gly Ser Ala Asn Ala Glu Phe Asp Gly Pro Tyr Ala Asp Gln
        35                  40                  45

Tyr Met Ser Ala Gln Thr Val Ala Val Phe Lys Pro Glu Val Gly Gly
    50                  55                  60

Tyr Leu Phe Arg Ser Gln Tyr Gly Glu Leu Leu Tyr Met Ser Lys Thr
65                  70                  75                  80

Ala Phe Glu Ala Asn Tyr Thr Ser Ala Ser Gly Ser Val Ala Asn Ala
                85                  90                  95

Glu Thr Ala Asp Lys Leu Ser Thr Ala Arg Thr Ile Thr Leu Thr Gly
            100                 105                 110

Ala Val Thr Gly Ser Ala Ser Phe Asp Gly Ser Ala Asn Val Thr Ile
            115                 120                 125

Glu Thr Thr Ser Gly Ser
            130

<210> SEQ ID NO 9
<211> LENGTH: 190
<212> TYPE: PRT
<213> ORGANISM: Enterobacteria phage P4

<400> SEQUENCE: 9

Met Glu Ser Thr Ala Leu Gln Gln Ala Phe Asp Thr Cys Gln Asn Asn
1               5                   10                  15

Lys Ala Ala Trp Leu Gln Arg Lys Asn Glu Leu Ala Ala Ala Glu Gln
            20                  25                  30

Glu Tyr Leu Arg Leu Leu Ser Gly Glu Gly Arg Asn Val Ser Arg Leu
        35                  40                  45

Asp Glu Leu Arg Asn Ile Ile Glu Val Arg Lys Trp Gln Val Asn Gln
    50                  55                  60

Ala Ala Gly Arg Tyr Ile Arg Ser His Glu Ala Val Gln His Ile Ser
65                  70                  75                  80

Ile Arg Asp Arg Leu Asn Asp Phe Met Gln Gln His Gly Thr Ala Leu
                85                  90                  95

Ala Ala Ala Leu Ala Pro Glu Leu Met Gly Tyr Ser Glu Leu Thr Ala
            100                 105                 110

Ile Ala Arg Asn Cys Ala Ile Gln Arg Ala Thr Asp Ala Leu Arg Glu
            115                 120                 125

Ala Leu Leu Ser Trp Leu Ala Lys Gly Glu Lys Ile Asn Tyr Ser Ala
        130                 135                 140

Gln Asp Ser Asp Ile Leu Thr Thr Ile Gly Phe Arg Pro Asp Val Ala
145                 150                 155                 160

Ser Val Asp Asp Ser Arg Glu Lys Phe Thr Pro Ala Gln Asn Met Ile
                165                 170                 175

Phe Ser Arg Lys Ser Ala Gln Leu Ala Ser Arg Gln Ser Val
            180                 185                 190

<210> SEQ ID NO 10
<211> LENGTH: 110
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)

<223> OTHER INFORMATION: Met is optionally absent.

<400> SEQUENCE: 10

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Cys Ser Arg Lys Leu Val
        35                  40                  45

Ala Trp Asp Gly Thr Thr Asp Gly Ala Ala Val Gly Ile Leu Ala Val
50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val
            100                 105                 110

<210> SEQ ID NO 11
<211> LENGTH: 27
<212> TYPE: DNA
<213> ORGANISM: Artificial Sequence
<220> FEATURE:
<223> OTHER INFORMATION: Synthetic

<400> SEQUENCE: 11
cgagcaaaga aacctgaacc cattacc                                           27

<210> SEQ ID NO 12
<211> LENGTH: 27
<212> TYPE: DNA
<213> ORGANISM: Artificial Sequence
<220> FEATURE:
<223> OTHER INFORMATION: Synthetic

<400> SEQUENCE: 12
ggtaatgggt tcaggtttct ttgctcg                                           27

<210> SEQ ID NO 13
<211> LENGTH: 36
<212> TYPE: DNA
<213> ORGANISM: Artificial Sequence
<220> FEATURE:
<223> OTHER INFORMATION: Synthetic

<400> SEQUENCE: 13
gctgatgctg gacacctgaa gccgtaagct ggttgc                                 36

<210> SEQ ID NO 14
<211> LENGTH: 36
<212> TYPE: DNA
<213> ORGANISM: Artificial Sequence
<220> FEATURE:
<223> OTHER INFORMATION: Synthetic

<400> SEQUENCE: 14
gcaaccagct tacggcttca ggtgtccagc atcagc                                 36

<210> SEQ ID NO 15
<211> LENGTH: 38
<212> TYPE: DNA
<213> ORGANISM: Artificial Sequence
<220> FEATURE:

<223> OTHER INFORMATION: Synthetic

<400> SEQUENCE: 15
ccgctgatgc tggacacctg cagccgtaag ctggttgc                                   38

<210> SEQ ID NO 16
<211> LENGTH: 38
<212> TYPE: DNA
<213> ORGANISM: Artificial Sequence
<220> FEATURE:
<223> OTHER INFORMATION: Synthetic

<400> SEQUENCE: 16
gcaaccagct tacggctgca ggtgtccagc atcagcgg                                   38

<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
gtgtaaggga tgcatatgac gagc                                                  24

<210> SEQ ID NO 18
<211> LENGTH: 40
<212> TYPE: DNA
<213> ORGANISM: Artificial Sequence
<220> FEATURE:
<223> OTHER INFORMATION: Synthetic

<400> SEQUENCE: 18
cacaccagtg taacatatgg gatccacgag caaagaaacc                                 40

<210> SEQ ID NO 19
<211> LENGTH: 27
<212> TYPE: DNA
<213> ORGANISM: Artificial Sequence
<220> FEATURE:
<223> OTHER INFORMATION: Synthetic

<400> SEQUENCE: 19
gtgatgaagg ggatccttaa acgatgc                                               27

<210> SEQ ID NO 20
<211> LENGTH: 52
<212> TYPE: DNA
<213> ORGANISM: Artificial Sequence
<220> FEATURE:
<223> OTHER INFORMATION: Synthetic

<400> SEQUENCE: 20
cgatttgctg aaccatatgc accatcacca ccatcacacg agcaaagaaa cc                   52

<210> SEQ ID NO 21
<211> LENGTH: 48
<212> TYPE: DNA
<213> ORGANISM: Artificial Sequence
<220> FEATURE:
<223> OTHER INFORMATION: Synthetic

<400> SEQUENCE: 21
gccgcacagg gatcctttta gtgatgatgg tgatgatgaa cgatgctg                        48

<210> SEQ ID NO 22
<211> LENGTH: 60
<212> TYPE: DNA
<213> ORGANISM: Artificial Sequence
<220> FEATURE:
<223> OTHER INFORMATION: Synthetic

<400> SEQUENCE: 22
gccgttaacg atcatatgtg cggatcaggg tcagggagtg gtagcacgag caaagaaacc    60

<210> SEQ ID NO 23
<211> LENGTH: 65
<212> TYPE: DNA
<213> ORGANISM: Artificial Sequence
<220> FEATURE:
<223> OTHER INFORMATION: Synthetic

<400> SEQUENCE: 23
cccgtaaaaa aagcctcgag ttagcaactt cctgatccag agccagatcc aacgatgctg    60
attgc    65

<210> SEQ ID NO 24
<211> LENGTH: 46
<212> TYPE: DNA
<213> ORGANISM: Artificial Sequence
<220> FEATURE:
<223> OTHER INFORMATION: Synthetic

<400> SEQUENCE: 24
gctgaacaca ccagctagcg gggggactgc gacgagcaaa gaaacc    46

<210> SEQ ID NO 25
<211> LENGTH: 45
<212> TYPE: DNA
<213> ORGANISM: Artificial Sequence
<220> FEATURE:
<223> OTHER INFORMATION: Synthetic

<400> SEQUENCE: 25
ggcggccttt aggctagcac ctccaagtcc aacgatgctg attgc    45

<210> SEQ ID NO 26
<211> LENGTH: 66
<212> TYPE: DNA
<213> ORGANISM: Artificial Sequence
<220> FEATURE:
<223> OTHER INFORMATION: Synthetic

<400> SEQUENCE: 26
cccgtaaaaa ccatggcagt gccgccgctt cctcctccag agccaagtcc aacgatgctg    60
attgcc    66

<210> SEQ ID NO 27
<211> LENGTH: 119
<212> TYPE: PRT
<213> ORGANISM: Artificial Sequence
<220> FEATURE:
<223> OTHER INFORMATION: Synthetic

<400> SEQUENCE: 27

Met Thr Ser Lys Glu Thr Phe Thr His Tyr Gln Pro Gln Gly Asn Ser
1               5                   10                  15

Asp Pro Ala His Thr Ala Thr Pro Gly Gly Leu Ser Ala Lys Ala
            20                  25                  30

```
Pro Ala Met Thr Pro Leu Met Leu Asp Thr Ser Ser Arg Lys Leu Val
            35                  40                  45

Ala Trp Asp Gly Thr Thr Asp Gly Ala Ala Val Gly Ile Leu Ala Val
 50                  55                  60

Ala Ala Asp Gln Thr Ser Thr Thr Leu Thr Phe Tyr Lys Ser Gly Thr
 65                  70                  75                  80

Phe Arg Tyr Glu Asp Val Leu Trp Pro Glu Ala Ala Ser Asp Glu Thr
                 85                  90                  95

Lys Lys Arg Thr Ala Phe Ala Gly Thr Ala Ile Ser Ile Val Gly Ser
            100                 105                 110

Gly Ser Gly Ser Gly Ser Cys
            115

<210> SEQ ID NO 28
<211> LENGTH: 119
<212> TYPE: PRT
<213> ORGANISM: Artificial Sequence
<220> FEATURE:
<223> OTHER INFORMATION: Synthetic

<400> SEQUENCE: 28

Cys Gly Ser Gly Ser Gly Ser Gly Ser Met Thr Ser Lys Glu Thr Phe
 1               5                  10                  15

Thr His Tyr Gln Pro Gln Gly Asn Ser Asp Pro Ala His Thr Ala Thr
             20                  25                  30

Ala Pro Gly Gly Leu Ser Ala Lys Ala Pro Ala Met Thr Pro Leu Met
            35                  40                  45

Leu Asp Thr Ser Ser Arg Lys Leu Val Ala Trp Asp Gly Thr Thr Asp
 50                  55                  60

Gly Ala Ala Val Gly Ile Leu Ala Val Ala Ala Asp Gln Thr Ser Thr
 65                  70                  75                  80

Thr Leu Thr Phe Tyr Lys Ser Gly Thr Phe Arg Tyr Glu Asp Val Leu
                 85                  90                  95

Trp Pro Glu Ala Ala Ser Asp Glu Thr Lys Lys Arg Thr Ala Phe Ala
            100                 105                 110

Gly Thr Ala Ile Ser Ile Val
            115

<210> SEQ ID NO 29
<211> LENGTH: 116
<212> TYPE: PRT
<213> ORGANISM: Artificial Sequence
<220> FEATURE:
<223> OTHER INFORMATION: Synthetic

<400> SEQUENCE: 29

Met Thr Ser Lys Glu Thr Phe Thr His Tyr Gln Pro Gln Gly Asn Ser
 1               5                  10                  15

Asp Pro Ala His Thr Ala Thr Ala Pro Gly Gly Leu Ser Ala Lys Ala
             20                  25                  30

Pro Ala Met Thr Pro Leu Met Leu Asp Thr Ser Ser Arg Lys Leu Val
            35                  40                  45

Ala Trp Asp Gly Thr Thr Asp Gly Ala Ala Val Gly Ile Leu Ala Val
 50                  55                  60

Ala Ala Asp Gln Thr Ser Thr Thr Leu Thr Phe Tyr Lys Ser Gly Thr
 65                  70                  75                  80

Phe Arg Tyr Glu Asp Val Leu Trp Pro Glu Ala Ala Ser Asp Glu Thr
                 85                  90                  95
```

Lys Lys Arg Thr Ala Phe Ala Gly Thr Ala Ile Ser Ile Val Gly Leu
            100                 105                 110

Gly Gly Ala Ser
        115

<210> SEQ ID NO 30
<211> LENGTH: 114
<212> TYPE: PRT
<213> ORGANISM: Artificial Sequence
<220> FEATURE:
<223> OTHER INFORMATION: Synthetic

<400> SEQUENCE: 30

Ala Ser Gly Gly Met Thr Ser Lys Glu Thr Phe Thr His Tyr Gln Pro
1               5                   10                  15

Gln Gly Asn Ser Asp Pro Ala His Thr Ala Thr Ala Pro Gly Gly Leu
            20                  25                  30

Ser Ala Lys Ala Pro Ala Met Thr Pro Leu Met Leu Asp Thr Ser Ser
        35                  40                  45

Arg Lys Leu Val Ala Trp Asp Gly Thr Thr Asp Gly Ala Ala Val Gly
    50                  55                  60

Ile Leu Ala Val Ala Ala Asp Gln Thr Ser Thr Thr Leu Thr Phe Tyr
65                  70                  75                  80

Lys Ser Gly Thr Phe Arg Tyr Glu Asp Val Leu Trp Pro Glu Ala Ala
                85                  90                  95

Ser Asp Glu Thr Lys Lys Arg Thr Ala Phe Ala Gly Thr Ala Ile Ser
            100                 105                 110

Ile Val

<210> SEQ ID NO 31
<211> LENGTH: 116
<212> TYPE: PRT
<213> ORGANISM: Artificial Sequence
<220> FEATURE:
<223> OTHER INFORMATION: Synthetic

<400> SEQUENCE: 31

His His His His His His Met Thr Ser Lys Glu Thr Phe Thr His Tyr
1               5                   10                  15

Gln Pro Gln Gly Asn Ser Asp Pro Ala His Thr Ala Thr Ala Pro Gly
            20                  25                  30

Gly Leu Ser Ala Lys Ala Pro Ala Met Thr Pro Leu Met Leu Asp Thr
        35                  40                  45

Ser Ser Arg Lys Leu Val Ala Trp Asp Gly Thr Thr Asp Gly Ala Ala
    50                  55                  60

Val Gly Ile Leu Ala Val Ala Ala Asp Gln Thr Ser Thr Thr Leu Thr
65                  70                  75                  80

Phe Tyr Lys Ser Gly Thr Phe Arg Tyr Glu Asp Val Leu Trp Pro Glu
                85                  90                  95

Ala Ala Ser Asp Glu Thr Lys Lys Arg Thr Ala Phe Ala Gly Thr Ala
            100                 105                 110

Ile Ser Ile Val
        115

<210> SEQ ID NO 32
<211> LENGTH: 116
<212> TYPE: PRT
<213> ORGANISM: Artificial Sequence

```
<220> FEATURE:
<223> OTHER INFORMATION: Synthetic

<400> SEQUENCE: 32

His His His His His His Met Thr Ser Lys Glu Thr Phe Thr His Tyr
1               5                   10                  15

Gln Pro Gln Gly Asn Ser Asp Pro Ala His Thr Ala Thr Ala Pro Gly
            20                  25                  30

Gly Leu Ser Ala Lys Ala Pro Ala Met Thr Pro Leu Met Leu Asp Thr
        35                  40                  45

Cys Ser Arg Lys Leu Val Ala Trp Asp Gly Thr Thr Asp Gly Ala Ala
    50                  55                  60

Val Gly Ile Leu Ala Val Ala Ala Asp Gln Thr Ser Thr Thr Leu Thr
65                  70                  75                  80

Phe Tyr Lys Ser Gly Thr Phe Arg Tyr Glu Asp Val Leu Trp Pro Glu
                85                  90                  95

Ala Ala Ser Asp Glu Thr Lys Lys Arg Thr Ala Phe Ala Gly Thr Ala
            100                 105                 110

Ile Ser Ile Val
        115

<210> SEQ ID NO 33
<211> LENGTH: 125
<212> TYPE: PRT
<213> ORGANISM: Artificial Sequence
<220> FEATURE:
<223> OTHER INFORMATION: Synthetic

<400> SEQUENCE: 33

His His His His His His Met Thr Ser Lys Glu Thr Phe Thr His Tyr
1               5                   10                  15

Gln Pro Gln Gly Asn Ser Asp Pro Ala His Thr Ala Thr Ala Pro Gly
            20                  25                  30

Gly Leu Ser Ala Lys Ala Pro Ala Met Thr Pro Leu Met Leu Asp Thr
        35                  40                  45

Ser Ser Arg Lys Leu Val Ala Trp Asp Gly Thr Thr Asp Gly Ala Ala
    50                  55                  60

Val Gly Ile Leu Ala Val Ala Ala Asp Gln Thr Ser Thr Thr Leu Thr
65                  70                  75                  80

Phe Tyr Lys Ser Gly Thr Phe Arg Tyr Glu Asp Val Leu Trp Pro Glu
                85                  90                  95

Ala Ala Ser Asp Glu Thr Lys Lys Arg Thr Ala Phe Ala Gly Thr Ala
            100                 105                 110

Ile Ser Ile Val Gly Ser Gly Ser Gly Ser Cys
        115                 120                 125

<210> SEQ ID NO 34
<211> LENGTH: 125
<212> TYPE: PRT
<213> ORGANISM: Artificial Sequence
<220> FEATURE:
<223> OTHER INFORMATION: Synthetic

<400> SEQUENCE: 34

Cys Gly Ser Gly Ser Gly Ser Gly Met Thr Ser Lys Glu Thr Phe
1               5                   10                  15

Thr His Tyr Gln Pro Gln Gly Asn Ser Asp Pro Ala His Thr Ala Thr
            20                  25                  30
```

Ala Pro Gly Gly Leu Ser Ala Lys Ala Pro Ala Met Thr Pro Leu Met
       35                  40                  45

Leu Asp Thr Ser Ser Arg Lys Leu Val Ala Trp Asp Gly Thr Thr Asp
 50                  55                  60

Gly Ala Ala Val Gly Ile Leu Ala Val Ala Ala Asp Gln Thr Ser Thr
 65                  70                  75                  80

Thr Leu Thr Phe Tyr Lys Ser Gly Thr Phe Arg Tyr Glu Asp Val Leu
                 85                  90                  95

Trp Pro Glu Ala Ala Ser Asp Glu Thr Lys Lys Arg Thr Ala Phe Ala
            100                 105                 110

Gly Thr Ala Ile Ser Ile Val His His His His His
        115                 120                 125

<210> SEQ ID NO 35
<211> LENGTH: 128
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (128)..(128)
<223> OTHER INFORMATION: N-terminal GFP

<400> SEQUENCE: 35

His His His His His His Met Thr Ser Lys Glu Thr Phe Thr His Tyr
 1               5                  10                  15

Gln Pro Gln Gly Asn Ser Asp Pro Ala His Thr Ala Thr Ala Pro Gly
            20                  25                  30

Gly Leu Ser Ala Lys Ala Pro Ala Met Thr Pro Leu Met Leu Asp Thr
        35                  40                  45

Ser Ser Arg Lys Leu Val Ala Trp Asp Gly Thr Thr Asp Gly Ala Ala
 50                  55                  60

Val Gly Ile Leu Ala Val Ala Ala Asp Gln Thr Ser Thr Thr Leu Thr
 65                  70                  75                  80

Phe Tyr Lys Ser Gly Thr Phe Arg Tyr Glu Asp Val Leu Trp Pro Glu
                 85                  90                  95

Ala Ala Ser Asp Glu Thr Lys Lys Arg Thr Ala Phe Ala Gly Thr Ala
            100                 105                 110

Ile Ser Ile Val Gly Leu Gly Ser Gly Gly Ser Gly Gly Thr Ala
        115                 120                 125

<210> SEQ ID NO 36
<211> LENGTH: 131
<212> TYPE: PRT
<213> ORGANISM: Artificial Sequence
<220> FEATURE:
<223> OTHER INFORMATION: Synthetic

<400> SEQUENCE: 36

Met Thr Lys Glu Thr Gln Ser Thr Thr Val Ser Ala Thr Ala Ser Gln
 1               5                  10                  15

Ala Asp Val Thr Asp Val Val Pro Ala Thr Glu Gly Glu Asn Ala Ser
            20                  25                  30

Ala Ala Gln Pro Asp Val Asn Ala Gln Ile Thr Ala Ala Val Ala Ala
        35                  40                  45

Glu Asn Ser Arg Ile Met Gly Ile Leu Asn Cys Glu Glu Ala His Gly
 50                  55                  60

```
Arg Glu Glu Gln Ala Arg Val Leu Ala Glu Thr Pro Gly Met Thr Val
 65              70                  75                  80

Lys Thr Ala Arg Arg Ile Leu Ala Ala Ala Pro Gln Ser Ala Gln Ala
                 85                  90                  95

Arg Ser Asp Thr Ala Leu Asp Arg Leu Met Gln Gly Ala Pro Ala Pro
             100                 105             110

Leu Ala Ala Gly Asn Pro Ala Ser Asp Ala Val Asn Asp Leu Leu Asn
         115                 120                 125

Thr Pro Val
     130
```